US010023875B2

(12) United States Patent
Schultheiss et al.

(10) Patent No.: US 10,023,875 B2
(45) Date of Patent: Jul. 17, 2018

(54) FUNGAL RESISTANT PLANTS EXPRESSING HCP5

(71) Applicant: BASF Plant Science Company GmbH, Ludwigshafen (DE)

(72) Inventors: Holger Schultheiss, Boehl-Iggelheim (DE); Ralf Flachmann, Limburgerhof (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 59 days.

(21) Appl. No.: 14/418,659

(22) PCT Filed: Jul. 30, 2013

(86) PCT No.: PCT/IB2013/056244
§ 371 (c)(1),
(2) Date: Jan. 30, 2015

(87) PCT Pub. No.: WO2014/024090
PCT Pub. Date: Feb. 13, 2014

(65) Prior Publication Data

US 2016/0040182 A1 Feb. 11, 2016

Related U.S. Application Data

(60) Provisional application No. 61/681,162, filed on Aug. 9, 2012.

(30) Foreign Application Priority Data

Aug. 9, 2012 (EP) .................................... 12179862

(51) Int. Cl.
*C12N 15/82* (2006.01)
*C07K 14/415* (2006.01)

(52) U.S. Cl.
CPC ........ *C12N 15/8282* (2013.01); *C07K 14/415* (2013.01)

(58) Field of Classification Search
None
See application file for complete search history.

(56) References Cited

U.S. PATENT DOCUMENTS

| | | | | |
|---|---|---|---|---|
| 7,294,760 | B2 * | 11/2007 | Ruezinsky | C12N 15/8234 435/320.1 |
| 2006/0150283 | A1 | 7/2006 | Alexandrov et al. | |
| 2007/0214517 | A1 * | 9/2007 | Alexandrov | C07K 14/415 800/278 |
| 2010/0132069 | A1 | 5/2010 | Lahaye et al. | |
| 2011/0107457 | A1 | 5/2011 | Frank et al. | |
| 2011/0172934 | A1 | 7/2011 | Frei et al. | |
| 2011/0252501 | A1 | 10/2011 | Abad et al. | |
| 2013/0219555 | A9 | 8/2013 | Lahaye et al. | |

FOREIGN PATENT DOCUMENTS

| | | | |
|---|---|---|---|
| CN | 101874115 | A | 10/2010 |
| CN | 102257144 | A | 11/2011 |
| WO | WO-2010023111 | A1 | 3/2010 |
| WO | WO-2010/037714 | A1 | 4/2010 |
| WO | WO-2012/023099 | A1 | 2/2012 |
| WO | WO-2012/023111 | A1 | 2/2012 |
| WO | WO-2012/172498 | A1 | 12/2012 |
| WO | WO-2013/001435 | A1 | 1/2013 |
| WO | WO-2013/092275 | A2 | 6/2013 |
| WO | WO-2013/093738 | A1 | 6/2013 |
| WO | WO-2013/149801 | A1 | 10/2013 |
| WO | WO-2013/149804 | A1 | 10/2013 |
| WO | WO-2013/152917 | A1 | 10/2013 |

OTHER PUBLICATIONS

Genbank accession # AB018117, bases 41499-43898, Feb. 2004.*
Guo et al, 2004, Proc. Natl. Acad. Sci. USA 101: 9205-9210.*
Glowacki et al, 2011, Cell. Mol. Biol. Lett. 16:1-24.*
European Search Report for Application No. EP 12 17 9862 dated Dec. 5, 2012.
GenBank Accession No. NP_199539, "disease resistance protein-like [*Arabidopsis thaliana*]" dated Aug. 13, 2001.
Grant et al., Targeted activation tagging of the *Arabidopsis* NBS-LRR gene, ADR1, conveys resistance to virulent pathogens, *Mol. Plant Microbe Interact.* 16(8): 669-80 (2003).
Heath, Cellular interactions between biotrophic fungal pathogens and host or nonhost plants, *Can. J. Plant Pathol.* 24: 259-64 (2002).
International Search Report for Application No. PCT/IB2013/056244 dated Feb. 6, 2014.
Mayank et al., Plant disease resistance genes: Current status and future directions, *Physiol. Mol. Plant Path.*78: 51-65 (2012).
Neu et al., Cytological and molecular analysis of the Hordeum vulgare-Puccinia triticina nonhost interaction, *Mol. Plant Microbe Interact.* 16(7): 626-33 (2003).
Rytter et al., "Additional alternative hosts of *Phakopsora pachyrhizi*, causal agent of soybean rust", *Plant Dis.* 68(9): 818-9 (1984).
Sinclair et al., (eds.) Proceedings of the soybean rust workshop, Urbana, IL: National Soybean Research Laboratory, 1: 1-11 (1995).
Uniprot Accession No. Q9LVT1, "Putative disease resistance protein At5g47280" dated Oct. 1, 2000.
Van Der Biezen et al., "The NB-ARC domain: a novel signaling motif shared by plant resistance gene products and regulators of cell death in animals", *Curr. Biol.* 8(7): R226-7 (1998).
Van Ooijen et al., "Structure-function analysis of the NB-ARC domain of plant disease resistance proteins", *J. Exp. Bot.*, 59(6): 1383-97 (2008).

* cited by examiner

*Primary Examiner* — Anne Kubelik
(74) *Attorney, Agent, or Firm* — Marshall, Gerstein & Borun LLP

(57) ABSTRACT

The present invention relates to a method of increasing resistance against fungal pathogens of the order Pucciniales, preferably the family Phacopsoraceae, in plants and/or plant cells. This is achieved by increasing the expression of an HCP5 protein or fragment thereof in a plant, plant part and/or plant cell in comparison to wild type plants, wild type plant parts and/or wild type plant cells. Furthermore, the invention relates to transgenic plants, plant parts, and/or plant cells having an increased resistance against fungal pathogens, in particular, pathogens of the order Pucciniales, preferably the family Phacopsoraceae, and to recombinant expression vectors comprising a sequence that is identical or homologous to a sequence encoding an HCP5 protein.

14 Claims, 11 Drawing Sheets

Figure 3:

```
   1 ATGCTTTTTA ATTTGAACGA TGAGGCAAGA ATTATTGGGA TCTCAGGGAT
  51 GATCGGTTCA GGGAAAACCA TTCTTGCCAA GGAGCTTGCG CGGGACGAGG
 101 AGGTCCGAGG TAATCAGTTT TGCCCTTTGT TATGTCTGAA ACTATCCATT
 151 GTTAATATGC TTGGGCCATC TTTGAAGTCT TTTGAGCAGT TTATGTTGTT
 201 GCTCAGTGGC ATGTTTACTG GTTTATTTGG ATGATCATGC ATTTATCTCT
 251 GTATGTTCCA TTGTGTCATG TTCATCTCCG GTGAACTGTT GATGAGTCGT
 301 ATAGTTGAGT TCTTGATATT AGAATCTGTT AAGAGTCGGA GAGACTGTTC
 351 CTTTGATGCT AAAAAAGCTT TAATACAGGC CATTTTGCGA ACCGAGTTTT
 401 GTTTCTGACT GTGTCACAAT CTCCCAATCT TGAGGAGCTG AGATCCCTTA
 451 TACGGGATTT TCTTACTGGT CATGAGGCTG GCTTTGGTAC CGCTCTTCCG
 501 GAATCCGTTG GTCATACACG GAAGCTAGTG ATCCTTGATG ATGTTAGGAC
 551 AAGGGAATCT CTAGACCAGC TGATGTTCAA TATTCCTGGA ACCACAACGC
 601 TTGTGGTCTC ACAGTCTAAA CTCGTAGATC CTAGAACCAC CTATGATGTA
 651 GAGTTATTAA ATGAACATGA CGCAACATCT CTGTTCTGTC TCTCTGCTTT
 701 CAACCAGAAA TCAGTTCCTT CAGGGTTCAG CAAAAGTTTG GTCAAGCAGG
 751 TAATGGGTCT GCTACAAGTG TTACATGCAT AGTAGTAATA TTCTTTGTAC
 801 TTTCAGTACT CATCTTGACT CTATTTGTTA GGTTGTTGGG GAGTCTAAAG
 851 GTCTACCTTT GTCTCTGAAA GTCCTTGGCG CTTCATTAAA CGATCGACCT
 901 GAAACATATT GGGCAATTGC AGTGGAGAGG TTATCAAGAG GTGAACCTGT
 951 TGATGAAACT CATGAGAGTA AAGTGTTTGC TCAAATCGAA GCAACTCTAG
1001 AAAATCTCGA TCCAAAAACC AAAGAGTGTT TCTTGGATAT GGGTGCTTTC
1051 CCTGAAGGCA AGAAAATCCC TGTTGATGTT CTCATCAACA TGTTGGTCAA
1101 GATACATGAT CTTGAGGACG CAGCCGCCTT TGATGTTCTT GTTGATCTAG
1151 CAAATAGGAA TCTTCTTACT CTCGTGAAAG ATCCAACGTA CGGTTATAGA
1201 ACTCTTTATG TTCTCATCTC TTGTAGCCAC TTTTATAATT TTAACCATTC
1251 TTAACTAATT TACCGTGGAT AATGTTGCAG GTTTGTCGCT ATGGGCACTA
1301 GCTACTATGA TATATTCGTG ACGCAGCACG ATGTTTTAAG AGATGTAGCA
1351 CTTCATCTTA CCAATCGTGG AAAAGTAAGT AGAAGAGACC GCTTATTGAT
1401 GCCAAAAAGA GAGACCATGC TTCCCAGCGA ATGGGAGAGG AGCAATGATG
1451 AGCCATACAA TGCACGAGTG GTTTCCATTC ACACAGGCAA GAATTTGTTA
1501 TGCAACGATC TTCTAATGAA TTAATTCGGT TCGTCACTAG AATCATAAGG
1551 TATTAATATG GATTTCTTTA CAGGAGAAAT GACTGAGATG GACTGGTTTG
1601 ACATGGATTT CCCCAAGGCA GAAGTTCTGA TAGTAAACTT CTCTTCAGAC
1651 AACTATGTAT TGCCTCCTTT CATTGCTAAG ATGGGAATGC TTAGGGTGTT
1701 CGTGATTATA AACAACGGTA CCTCTCCAGC GCATCTACAT GACTTCCCCA
1751 TCCCTACCAG TTTGACCAAT CTAAGGAGTC TCTGGCTTGA GAGGGTTCAT
1801 GTCCCTGAAC TCTCTAGCAG TATGATACCC TTGAAAAACC TCCACAAGCT
1851 ATATCTGATT ATTTGCAAGA TCAATAACAG TTTTGATCAG ACAGCCATAG
1901 ACATTGCCCA AATCTTCCCA AAATTGACTG ATATCACAAT AGATTATTGC
1951 GATGATCTTG CGGAACTACC TTCGACCATC TGTGGAATAA CCTCTCTCAA
2001 CTCCATCAGC ATAACAAATT GTCCCAACAT CAAGGAGTTA CCGAAGAATA
2051 TAAGTAAGCT ACAAGCCCTT CAACTTTTGA GGCTATACGC TTGCCCAGAG
2101 CTAAAATCTC TGCCTGTGGA AATCTGTGAA TTGCCAAGAC TAGTGTATGT
2151 CGACATCTCT CACTGTCTCA GCCTAAGTTC TCTTCCGGAA AAGATAGGAA
2201 ATGTAAGGAC ACTTGAGAAA ATCGACATGA GAGAATGTAG CTTATCGAGC
2251 ATACCAAGTT CCGCAGTTTC ATTGACTTCC CTATGCTATG TAACATGCTA
2301 TAGAGAGGCT TTGTGGATGT GGAAAGAGGT TGAGAAGGCA GTTCCCGGAC
2351 TTCGTATTGA AGCTACTGAA AAATGGTTCA ACATGACTTG GCCCGACGAG
2401 TAG
```

Figure 4:

```
   1 ATGCTTTTTA ATTTGAACGA TGAGGCAAGA ATTATTGGGA TCTCAGGGAT
  51 GATCGGTTCA GGGAAAACCA TTCTTGCCAA GGAGCTTGCG CGGGACGAGG
 101 AGGTCCGAGG CCATTTTGCG AACCGAGTTT TGTTTCTGAC TGTGTCACAA
 151 TCTCCCAATC TTGAGGAGCT GAGATCCCTT ATACGGGATT TTCTTACTGG
 201 TCATGAGGCT GGCTTTGGTA CCGCTCTTCC GGAATCCGTT GGTCATACAC
 251 GGAAGCTAGT GATCCTTGAT GATGTTAGGA CAAGGGAATC TCTAGACCAG
 301 CTGATGTTCA ATATTCCTGG AACCACAACG CTTGTGGTCT CACAGTCTAA
 351 ACTCGTAGAT CCTAGAACCA CCTATGATGT AGAGTTATTA AATGAACATG
 401 ACGCAACATC TCTGTTCTGT CTCTCTGCTT TCAACCAGAA ATCAGTTCCT
 451 TCAGGGTTCA GCAAAAGTTT GGTCAAGCAG GTTGTTGGGG AGTCTAAAGG
 501 TCTACCTTTG TCTCTGAAAG TCCTTGGCGC TTCATTAAAC GATCGACCTG
 551 AAACATATTG GGCAATTGCA GTGGAGAGGT TATCAAGAGG TGAACCTGTT
 601 GATGAAACTC ATGAGAGTAA AGTGTTTGCT CAAATCGAAG CAACTCTAGA
 651 AAATCTCGAT CCAAAAACCA AAGAGTGTTT CTTGGATATG GGTGCTTTCC
 701 CTGAAGGCAA GAAAATCCCT GTTGATGTTC TCATCAACAT GTTGGTCAAG
 751 ATACATGATC TTGAGGACGC AGCCGCCTTT GATGTTCTTG TTGATCTAGC
 801 AAATAGGAAT CTTCTTACTC TCGTGAAAGA TCCAACGTTT GTCGCTATGG
 851 GCACTAGCTA CTATGATATA TTCGTGACGC AGCACGATGT TTTAAGAGAT
 901 GTAGCACTTC ATCTTACCAA TCGTGGAAAA GTAAGTAGAA GAGACCGCTT
 951 ATTGATGCCA AAAAGAGAGA CCATGCTTCC CAGCGAATGG GAGAGGAGCA
1001 ATGATGAGCC ATACAATGCA CGAGTGGTTT CCATTCACAC AGGAGAAATG
1051 ACTGAGATGG ACTGGTTTGA CATGGATTTC CCCAAGGCAG AAGTTCTGAT
1101 AGTAAACTTC TCTTCAGACA ACTATGTATT GCCTCCTTTC ATTGCTAAGA
1151 TGGGAATGCT TAGGGTGTTC GTGATTATAA ACAACGGTAC CTCTCCAGCG
1201 CATCTACATG ACTTCCCCAT CCCTACCAGT TTGACCAATC TAAGGAGTCT
1251 CTGGCTTGAG AGGGTTCATG TCCCTGAACT CTCTAGCAGT ATGATACCCT
1301 TGAAAAACCT CCACAAGCTA TATCTGATTA TTTGCAAGAT CAATAACAGT
1351 TTTGATCAGA CAGCCATAGA CATTGCCCAA ATCTTCCCAA AATTGACTGA
1401 TATCACAATA GATTATTGCG ATGATCTTGC GGAACTACCT TCGACCATCT
1451 GTGGAATAAC CTCTCTCAAC TCCATCAGCA TAACAAATTG TCCCAACATC
1501 AAGGAGTTAC CGAAGAATAT AAGTAAGCTA CAAGCCCTTC AACTTTTGAG
1551 GCTATACGCT TGCCCAGAGC TAAAATCTCT GCCTGTGGAA ATCTGTGAAT
1601 TGCCAAGACT AGTGTATGTC GACATCTCTC ACTGTCTCAG CCTAAGTTCT
1651 CTTCCGGAAA AGATAGGAAA TGTAAGGACA CTTGAGAAAA TCGACATGAG
1701 AGAATGTAGC TTATCGAGCA TACCAAGTTC CGCAGTTTCA TTGACTTCCC
1751 TATGCTATGT AACATGCTAT AGAGAGGCTT TGTGGATGTG GAAAGAGGTT
1801 GAGAAGGCAG TTCCCGGACT TCGTATTGAA GCTACTGAAA AATGGTTCAA
1851 CATGACTTGG CCCGACGAGT AG
```

Figure 5:

```
MLFNLNDEARIIGISGMIGSGKTILAKELARDEEVRGHFANRVLFLTVSQ  50
SPNLEELRSLIRDFLTGHEAGFGTALPESVGHTRKLVILDDVRTRESLDQ 100
LMFNIPGTTTLVVSQSKLVDPRTTYDVELLNEHDATSLFCLSAFNQKSVP 150
SGFSKSLVKQVVGESKGLPLSLKVLGASLNDRPETYWAIAVERLSRGEPV 200
DETHESKVFAQIEATLENLDPKTKECFLDMGAFPEGKKIPVDVLINMLVK 250
IHDLEDAAAFDVLVDLANRNLLTLVKDPTFVAMGTSYYDIFVTQHDVLRD 300
VALHLTNRGKVSRRDRLLMPKRETMLPSEWERSNDEPYNARVVSIHTGEM 350
TEMDWFDMDFPKAEVLIVNFSSDNYVLPPFIAKMGMLRVFVIINNGTSPA 400
HLHDFPIPTSLTNLRSLWLERVHVPELSSSMIPLKNLHKLYLIICKINNS 450
FDQTAIDIAQIFPKLTDITIDYCDDLAELPSTICGITSLNSISITNCPNI 500
KELPKNISKLQALQLLRLYACPELKSLPVEICELPRLVYVDISHCLSLSS 550
LPEKIGNVRTLEKIDMRECSLSSIPSSAVSLTSLCYVTCYREALWMWKEV 600
EKAVPGLRIEATEKWFNMTWPDE*
```

Figure 6:

```
   1 ACAAACTCTC ATTCATTAAA CTAGTGACTA AAGTTTACTT TGCTCACAAA
  51 AGAGTTGATT TAAACGTTTT CACAAACACC ATCCGGACGT AAAATGTGTA
 101 ATGGAACATA CATAGAGACC AAATAATTAT AAATTTATAA TAGATAATGC
 151 TTCTATGTAT ATGTATGTTT GTATGTAAGA TTACGTCATC TCAGGTGAAC
 201 TATTGTTGAG TTTTTGATAT TGAACACTGG TTAAAAGTCA TTGAGACTGT
 251 GTCTCTGATG CTAGAAAGTC CTTCATTTGA TGCTAAAAAG ACTTTGGGAT
 301 CCGAGTTTTG TTTCTGACTG TGTCATATTT TCTGACTTTG GGAACTGGAT
 351 TTAGGCAAGA GGAAGGTGAA GGAGATGCTT TTTAATTTGA ACGATGAGGC
 401 AAGAATTATT GGGATCTCAG GGATGATCGG TTCAGGGAAA ACCATTCTTG
 451 CCAAGGAGCT TGCGCGGGAC GAGGAGGTCC GAGGTAATCA GTTTTGCCCT
 501 TTGTTATGTC TGAAACTATC CATTGTTAAT ATGCTTGGGC CATCTTTGAA
 551 GTCTTTTGAG CAGTTTATGT TGTTGCTCAG TGGCATGTTT ACTGGTTTAT
 601 TTGGATGATC ATGCATTTAT CTCTGTATGT TCCATTGTGT CATGTTCATC
 651 TCCGGTGAAC TGTTGATGAG TCGTATAGTT GAGTTCTTGA TATTAGAATC
 701 TGTTAAGAGT CGGAGAGACT GTTCCTTTGA TGCTAAAAAA GCTTTAATAC
 751 AGGCCATTTT GCGAACCGAG TTTTGTTTCT GACTGTGTCA CAATCTCCCA
 801 ATCTTGAGGA GCTGAGATCC CTTATACGGG ATTTTCTTAC TGGTCATGAG
 851 GCTGGCTTTG GTACCGCTCT TCCGGAATCC GTTGGTCATA CACGGAAGCT
 901 AGTGATCCTT GATGATGTTA GGACAAGGGA ATCTCTAGAC CAGCTGATGT
 951 TCAATATTCC TGGAACCACA ACGCTTGTGG TCTCACAGTC TAAACTCGTA
1001 GATCCTAGAA CCACCTATGA TGTAGAGTTA TTAAATGAAC ATGACGCAAC
1051 ATCTCTGTTC TGTCTCTCTG CTTTCAACCA GAAATCAGTT CCTTCAGGGT
1101 TCAGCAAAAG TTTGGTCAAG CAGGTAATGG GTCTGCTACA AGTGTTACAT
1151 GCATAGTAGT AATATTCTTT GTACTTTCAG TACTCATCTT GACTCTATTT
1201 GTTAGGTTGT TGGGGAGTCT AAAGGTCTAC CTTTGTCTCT GAAAGTCCTT
1251 GGCGCTTCAT TAAACGATCG ACCTGAAACA TATTGGGCAA TTGCAGTGGA
1301 GAGGTTATCA AGAGGTGAAC CTGTTGATGA AACTCATGAG AGTAAAGTGT
1351 TTGCTCAAAT CGAAGCAACT CTAGAAAATC TCGATCCAAA AACCAAAGAG
1401 TGTTTCTTGG ATATGGGTGC TTTCCCTGAA GGCAAGAAAA TCCCTGTTGA
1451 TGTTCTCATC AACATGTTGG TCAAGATACA TGATCTTGAG GACGCAGCCG
1501 CCTTTGATGT TCTTGTTGAT CTAGCAAATA GGAATCTTCT TACTCTCGTG
1551 AAAGATCCAA CGTACGGTTA TAGAACTCTT TATGTTCTCA TCTCTTGTAG
1601 CCACTTTTAT AATTTTAACC ATTCTTAACT AATTTACCGT GGATAATGTT
1651 GCAGGTTTGT CGCTATGGGC ACTAGCTACT ATGATATATT CGTGACGCAG
1701 CACGATGTTT TAAGAGATGT AGCACTTCAT CTTACCAATC GTGGAAAAGT
1751 AAGTAGAAGA GACCGCTTAT TGATGCCAAA AAGAGAGACC ATGCTTCCCA
1801 GCGAATGGGA GAGGAGCAAT GATGAGCCAT ACAATGCACG AGTGGTTTCC
1851 ATTCACACAG GCAAGAATTT GTTATGCAAC GATCTTCTAA TGAATTAATT
1901 CGGTTCGTCA CTAGAATCAT AAGGTATTAA TATGGATTTC TTTACAGGAG
1951 AAATGACTGA GATGGACTGG TTTGACATGG ATTTCCCCAA GGCAGAAGTT
2001 CTGATAGTAA ACTTCTCTTC AGACAACTAT GTATTGCCTC CTTTCATTGC
2051 TAAGATGGGA ATGCTTAGGG TGTTCGTGAT TATAAACAAC GGTACCTCTC
2101 CAGCGCATCT ACATGACTTC CCCATCCCTA CCAGTTTGAC CAATCTAAGG
2151 AGTCTCTGGC TTGAGAGGGT TCATGTCCCT GAACTCTCTA GCAGTATGAT
2201 ACCCTTGAAA AACCTCCACA AGCTATATCT GATTATTTGC AAGATCAATA
2251 ACAGTTTTGA TCAGACAGCC ATAGACATTG CCCAAATCTT CCCAAAATTG
2301 ACTGATATCA CAATAGATTA TTGCGATGAT CTTGCGGAAC TACCTTCGAC
2351 CATCTGTGGA ATAACCTCTC TCAACTCCAT CAGCATAACA AATTGTCCCA
2401 ACATCAAGGA GTTACCGAAG AATATAAGTA AGCTACAAGC CCTTCAACTT
2451 TTGAGGCTAT ACGCTTGCCC AGAGCTAAAA TCTCTGCCTG TGGAAATCTG
2501 TGAATTGCCA AGACTAGTGT ATGTCGACAT CTCTCACTGT CTCAGCCTAA
2551 GTTCTCTTCC GGAAAAGATA GGAAATGTAA GGACACTTGA GAAAATCGAC
2601 ATGAGAGAAT GTAGCTTATC GAGCATACCA AGTTCCGCAG TTTCATTGAC
2651 TTCCCTATGC TATGTAACAT GCTATAGAGA GGCTTTGTGG ATGTGGAAAG
2701 AGGTTGAGAA GGCAGTTCCC GGACTTCGTA TTGAAGCTAC TGAAAAATGG
```

Figure 6 - continued:

```
2751 TTCAACATGA CTTGGCCCGA CGAGTAGTAG GTTCTTAATT CTCCCTCCGA
2801 GCTTTTGAAA ATGCATGTTG TATTATTATT TATTAACTCG ATTAGGACCC
2851 CTGTATGATA TACGATTTTA TTAATACATG TTTTGCTCTT ATAACGTCAA
2901 TATATAAATT ATATGTTGAT TTTAAGTATT AAAAGTTTCT ATTTGGAATC
2951 TCAAAGATAT GTTTTTAAAG ATTCACTTAT AAGTAATAAC AAACAAACAA
3001 AAACTATTTA GCTTAATGGT AAAAAGCATG AGTCTATATA GAGAAGGGTT
3051 CATAATTTAA AATTAGTTTG AATGTTGTTT GTTATTAAGT GAGATACATT
3101 TTAAAATAAT TTAGTGAGAT AAA
```

Figure 7 - continued:

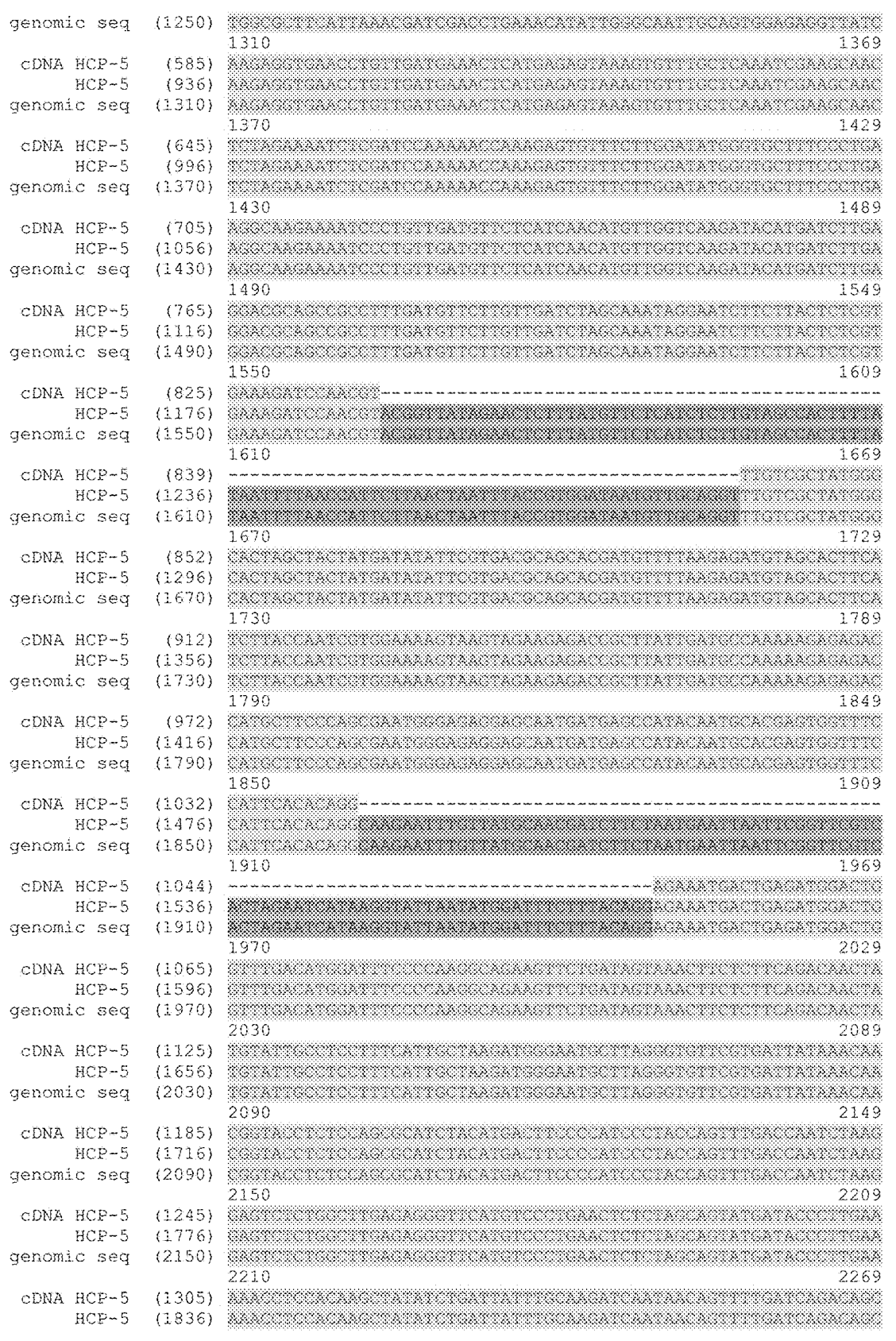

```
genomic seq  (1250) TGGCGCTTCATTAAACGATCGACCTGAAACATATTGGCAATTGCAGTGGAGAGGTTATC
                    1310                                                    1369
  cDNA HCP-5  (585) AAGAGGTGAACCTGTTGATGAAACTCATGAGAGTAAAGTGTTTGCTCAAATCGAAGCAAC
       HCP-5  (936) AAGAGGTGAACCTGTTGATGAAACTCATGAGAGTAAAGTGTTTGCTCAAATCGAAGCAAC
genomic seq  (1310) AAGAGGTGAACCTGTTGATGAAACTCATGAGAGTAAAGTGTTTGCTCAAATCGAAGCAAC
                    1370                                                    1429
  cDNA HCP-5  (645) TCTAGAAAATCTCGATCCAAAAACCAAAGAGTGTTTCTTGGATATGGGTGCTTTCCCTGA
       HCP-5  (996) TCTAGAAAATCTCGATCCAAAAACCAAAGAGTGTTTCTTGGATATGGGTGCTTTCCCTGA
genomic seq  (1370) TCTAGAAAATCTCGATCCAAAAACCAAAGAGTGTTTCTTGGATATGGGTGCTTTCCCTGA
                    1430                                                    1489
  cDNA HCP-5  (705) AGGCAAGAAAATCCCTGTTGATGTTCTCATCAACATGTTGGTCAAGATACATGATCTTGA
       HCP-5 (1056) AGGCAAGAAAATCCCTGTTGATGTTCTCATCAACATGTTGGTCAAGATACATGATCTTGA
genomic seq  (1430) AGGCAAGAAAATCCCTGTTGATGTTCTCATCAACATGTTGGTCAAGATACATGATCTTGA
                    1490                                                    1549
  cDNA HCP-5  (765) GGACGCAGCCGCCTTTGATGTTCTTGTTGATCTAGCAAATAGCAATCTTCTTACTCTCGT
       HCP-5 (1116) GGACGCAGCCGCCTTTGATGTTCTTGTTGATCTAGCAAATAGCAATCTTCTTACTCTCGT
genomic seq  (1490) GGACGCAGCCGCCTTTGATGTTCTTGTTGATCTAGCAAATAGCAATCTTCTTACTCTCGT
                    1550                                                    1609
  cDNA HCP-5  (825) GAAAGATCCAACGT----------------------------------------------
       HCP-5 (1176) GAAAGATCCAACGTACGTTATAGAACTCTTTATGTTCTAATCTCTTGTAGCAACACTTTA
genomic seq  (1550) GAAAGATCCAACGTACGTTATAGAACTCTTTATGTTCTAATCTCTTGTAGCAACACTTTA
                    1610                                                    1669
  cDNA HCP-5  (839) ------------------------------------------------TTGTCGCTATGG
       HCP-5 (1236) TAATTTTAACCATTCTTAACTAATTTACCTTTTGATAATGTTGCAGGTTTGTCGCTATGG
genomic seq  (1610) TAATTTTAACCATTCTTAACTAATTTACCTTTTGATAATGTTGCAGGTTTGTCGCTATGG
                    1670                                                    1729
  cDNA HCP-5  (852) CACTAGCTACTATGATATATTCGTGACGCAGCACGATGTTTTAAGAGATGTAGCACTTCA
       HCP-5 (1296) CACTAGCTACTATGATATATTCGTGACGCAGCACGATGTTTTAAGAGATGTAGCACTTCA
genomic seq  (1670) CACTAGCTACTATGATATATTCGTGACGCAGCACGATGTTTTAAGAGATGTAGCACTTCA
                    1730                                                    1789
  cDNA HCP-5  (912) TCTTACCAATCGTGGAAAAGTAACTAGAAGAGACCGCTTATTGATGCCAAAAAGAGAGAC
       HCP-5 (1356) TCTTACCAATCGTGGAAAAGTAACTAGAAGAGACCGCTTATTGATGCCAAAAAGAGAGAC
genomic seq  (1730) TCTTACCAATCGTGGAAAAGTAACTAGAAGAGACCGCTTATTGATGCCAAAAAGAGAGAC
                    1790                                                    1849
  cDNA HCP-5  (972) CATGCTTCCCAGCGAATGGAGAGGAGCAATGATGAGCCATACAATGCACCAGTGGTTTTC
       HCP-5 (1416) CATGCTTCCCAGCGAATGGAGAGGAGCAATGATGAGCCATACAATGCACCAGTGGTTTTC
genomic seq  (1790) CATGCTTCCCAGCGAATGGAGAGGAGCAATGATGAGCCATACAATGCACCAGTGGTTTTC
                    1850                                                    1909
  cDNA HCP-5 (1032) CATTCACACAGG------------------------------------------------
       HCP-5 (1476) CATTCACACAGGCAAGAATTTGCTTACCAACCATCTTCTAATGAATTAATTGGCTTCGTG
genomic seq  (1850) CATTCACACAGGCAAGAATTTGCTTACCAACCATCTTCTAATGAATTAATTGGCTTCGTG
                    1910                                                    1969
  cDNA HCP-5 (1044) ---------------------------------------ACAAATGACTGACATGGACTG
       HCP-5 (1536) ACTACGATCATAACGTATTAATATGGATTTCTTTATAGGACAAATGACTGACATGGACTG
genomic seq  (1910) ACTACGATCATAACGTATTAATATGGATTTCTTTATAGGACAAATGACTGACATGGACTG
                    1970                                                    2029
  cDNA HCP-5 (1065) GTTTGACATGGATTTCCCCAAGGCAGAAGTTCTCATAGTAAACTTCTCTTCAGACAACTA
       HCP-5 (1596) GTTTGACATGGATTTCCCCAAGGCAGAAGTTCTCATAGTAAACTTCTCTTCAGACAACTA
genomic seq  (1970) GTTTGACATGGATTTCCCCAAGGCAGAAGTTCTCATAGTAAACTTCTCTTCAGACAACTA
                    2030                                                    2089
  cDNA HCP-5 (1125) TGTATTGCCTCCTTTCATTGCTAAGATGGGAATGCTTAGGGTGTTCGTGATTATAAACAA
       HCP-5 (1656) TGTATTGCCTCCTTTCATTGCTAAGATGGGAATGCTTAGGGTGTTCGTGATTATAAACAA
genomic seq  (2030) TGTATTGCCTCCTTTCATTGCTAAGATGGGAATGCTTAGGGTGTTCGTGATTATAAACAA
                    2090                                                    2149
  cDNA HCP-5 (1185) CCGTACCTCTCCAGCCCATCTACATGACTTCCCCATCCCTACCAGTTTGACCAATCTAAC
       HCP-5 (1716) CCGTACCTCTCCAGCCCATCTACATGACTTCCCCATCCCTACCAGTTTGACCAATCTAAC
genomic seq  (2090) CCGTACCTCTCCAGCCCATCTACATGACTTCCCCATCCCTACCAGTTTGACCAATCTAAC
                    2150                                                    2209
  cDNA HCP-5 (1245) GAGTCTCTGGCTTGAGAGGGTTCATGTCCCTGAACTCTTAGCACTATGATACCCCTTGAA
       HCP-5 (1776) GAGTCTCTGGCTTGAGAGGGTTCATGTCCCTGAACTCTTAGCACTATGATACCCCTTGAA
genomic seq  (2150) GAGTCTCTGGCTTGAGAGGGTTCATGTCCCTGAACTCTTAGCACTATGATACCCCTTGAA
                    2210                                                    2269
  cDNA HCP-5 (1305) AAACCTCCACAAGCTATATCTGATTATTTGCAAGATCAATAACAGTTTTGATCAGACAGC
       HCP-5 (1836) AAACCTCCACAAGCTATATCTGATTATTTGCAAGATCAATAACAGTTTTGATCAGACAGC
```

Figure 7 - continued:

```
genomic seq  (2210) AAACCTCCACAAGCTATATCTGATTATTTCCAAGATCAATAACAGTTTTGATCAGACACC
                    2270                                                     2329
  cDNA HCP-5 (1365) CATAGACATTGCCCAAATCTTCCCAAAATTGACTGATATCACAATAGATTATTGCCATCA
       HCP-5 (1896) CATAGACATTGCCCAAATCTTCCCAAAATTGACTGATATCACAATAGATTATTGCCATCA
genomic seq  (2270) CATAGACATTGCCCAAATCTTCCCAAAATTGACTGATATCACAATAGATTATTGCCATCA
                    2330                                                     2389
  cDNA HCP-5 (1425) TCTTGCGGAACTACCTTCGACCATCTGTGGAATAACCTCTCTCAACTCCATCAGCATAAC
       HCP-5 (1956) TCTTGCGGAACTACCTTCGACCATCTGTGGAATAACCTCTCTCAACTCCATCAGCATAAC
genomic seq  (2330) TCTTGCGGAACTACCTTCGACCATCTGTGGAATAACCTCTCTCAACTCCATCAGCATAAC
                    2390                                                     2449
  cDNA HCP-5 (1485) AAATTGTCCCAACATCAAGGAGTTACCGAAGAATATAAGTAAGCTACAAGCCCTTCAACT
       HCP-5 (2016) AAATTGTCCCAACATCAAGGAGTTACCGAAGAATATAAGTAAGCTACAAGCCCTTCAACT
genomic seq  (2390) AAATTGTCCCAACATCAAGGAGTTACCGAAGAATATAAGTAAGCTACAAGCCCTTCAACT
                    2450                                                     2509
  cDNA HCP-5 (1545) TTTGAGGCTATACGCTTGCCCAGAGCTAAAATCTCTGCCTGTGGAAATCTGTGAATTGCC
       HCP-5 (2076) TTTGAGGCTATACGCTTGCCCAGAGCTAAAATCTCTGCCTGTGGAAATCTGTGAATTGCC
genomic seq  (2450) TTTGAGGCTATACGCTTGCCCAGAGCTAAAATCTCTGCCTGTGGAAATCTGTGAATTGCC
                    2510                                                     2569
  cDNA HCP-5 (1605) AAGACTAGTGTATGTCGACATCTCTCACTGTCTCAGCCTAAGTTCTCTTCCCGAAAAGAT
       HCP-5 (2136) AAGACTAGTGTATGTCGACATCTCTCACTGTCTCAGCCTAAGTTCTCTTCCCGAAAAGAT
genomic seq  (2510) AAGACTAGTGTATGTCGACATCTCTCACTGTCTCAGCCTAAGTTCTCTTCCCGAAAAGAT
                    2570                                                     2629
  cDNA HCP-5 (1665) AGGAAATGTAAGGACACTTGAGAAAATCGACATGAGAGAATGTAGCTTATCGAGCATACC
       HCP-5 (2196) AGGAAATGTAAGGACACTTGAGAAAATCGACATGAGAGAATGTAGCTTATCGAGCATACC
genomic seq  (2570) AGGAAATGTAAGGACACTTGAGAAAATCGACATGAGAGAATGTAGCTTATCGAGCATACC
                    2630                                                     2689
  cDNA HCP-5 (1725) AAGTTCCGCAGTTTCATTGACTTCCCTATGCTATGTAACATGCTATAGAGAGGCTTTGTG
       HCP-5 (2256) AAGTTCCGCAGTTTCATTGACTTCCCTATGCTATGTAACATGCTATAGAGAGGCTTTGTG
genomic seq  (2630) AAGTTCCGCAGTTTCATTGACTTCCCTATGCTATGTAACATGCTATAGAGAGGCTTTGTG
                    2690                                                     2749
  cDNA HCP-5 (1785) GATGTGGAAAGAGGTTGAGAAGGCACTTCCCGGACTTCGTATTGAAGCTACTGAAAAATG
       HCP-5 (2316) GATGTGGAAAGAGGTTGAGAAGGCACTTCCCGGACTTCGTATTGAAGCTACTGAAAAATG
genomic seq  (2690) GATGTGGAAAGAGGTTGAGAAGGCACTTCCCGGACTTCGTATTGAAGCTACTGAAAAATG
                    2750                                             2800
  cDNA HCP-5 (1845) GTTCAACATGACTTGGCCCGACGAGTAG-----------------------
       HCP-5 (2376) GTTCAACATGACTTGGCCCGACGAGTAG-----------------------
genomic seq  (2750) GTTCAACATGACTTGGCCCGACGAGTAGTAGGTTCTTAATTCTCCCTCCGA
```

Figure 8:

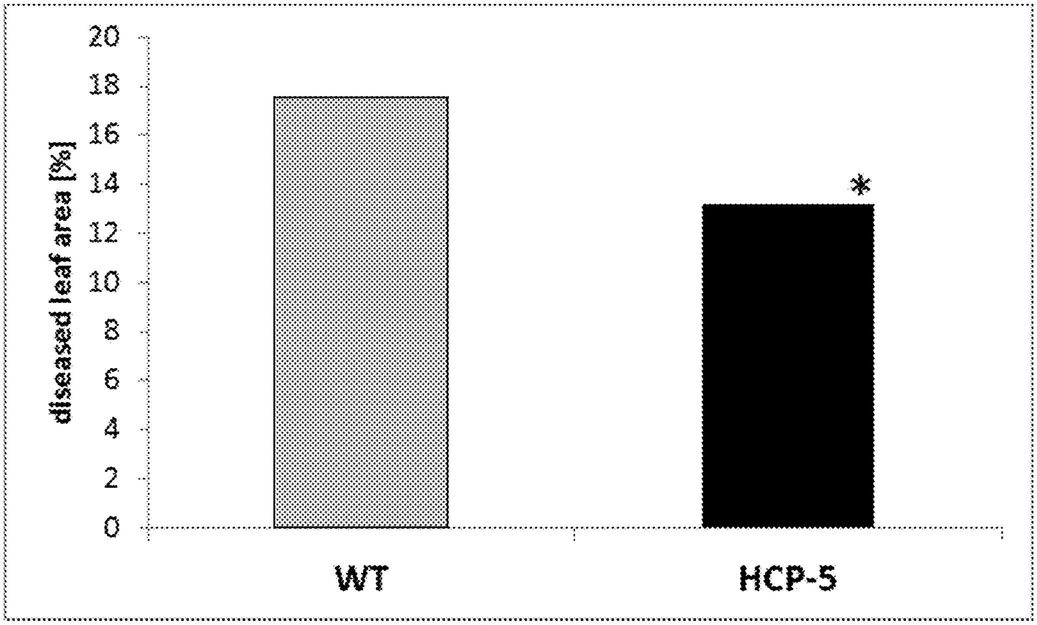

Figure 9:

| SEQ ID NO: | Description of the sequence |
|---|---|
| 1 | Nucleotide sequence HCP5 splice variant 1; Arabidopsis thaliana |
| 2 | Nucleotide sequence HCP5 splice variant 2; Arabidopsis thaliana |
| 3 | Amino acid sequence of HCP5; Arabidopsis thaliana |
| 4 | Nucleotide sequence HCP5 genomic sequence; Arabidopsis thaliana |
| 5 | Nucleotide sequence HCP5 genomic sequence; truncated as used in Figure 3; Arabidopsis thaliana |
| 6 | HCP5 forward primer |
| 7 | HCP5 reverse primer |
| 8 | Forward reamplification primer |
| 9 | Reverse reamplification primer |
| 10 | Nucleotide sequence HCP5; variant of splice variant 1; Arabidopsis thaliana |
| 11 | Nucleotide sequence of HCP5 large exon; Arabidopsis thaliana |
| 12 | Amino acid sequence of HCP5 large exon; Arabidopsis thaliana |
| 13 | Nucleotide sequence HCP5, variant 1 |
| 14 | Nucleotide sequence HCP5, variant 2 |
| 15 | Nucleotide sequence HCP5, variant 3 |
| 16 | Nucleotide sequence HCP5, variant 4 |

FIGURE 9 – continued:

| SEQ ID NO: | Description of the sequence |
|---|---|
| 17 | Nucleotide sequence HCP5, variant 5 |
| 18 | Nucleotide sequence HCP5, variant 6 |
| 19 | Nucleotide sequence HCP5, variant 7 |
| 20 | Nucleotide sequence HCP5, variant 8 |
| 21 | Amino acid sequence HCP5, variant 8 |
| 22 | Nucleotide sequence HCP5, variant 9 |
| 23 | Amino acid sequence HCP5, variant 9 |
| 24 | Nucleotide sequence HCP5, variant 10 |
| 25 | Amino acid sequence HCP5, variant 10 |
| 26 | Nucleotide sequence HCP5, variant 11 |
| 27 | Amino acid sequence HCP5, variant 11 |
| 28 | Nucleotide sequence HCP5, variant 12 |
| 29 | Amino acid sequence HCP5, variant 12 |
| 30 | Nucleotide sequence HCP5, variant 13 |
| 31 | Amino acid sequence HCP5, variant 13 |
| 32 | Nucleotide sequence HCP5, variant 14 |
| 33 | Amino acid sequence HCP5, variant 14 |
| 34 | Nucleotide sequence HCP5, variant 15 |
| 35 | Amino acid sequence HCP5, variant 15 |

SEQUENCE LISTING

```
<160> NUMBER OF SEQ ID NOS: 35

<210> SEQ ID NO 1
<211> LENGTH: 2403
<212> TYPE: DNA
<213> ORGANISM: Arabidopsis thaliana
<220> FEATURE:
<221> NAME/KEY: source
<222> LOCATION: 1..2403
<223> OTHER INFORMATION: /organism="Arabidopsis thaliana"
      /mol_type="unassigned DNA"

<400> SEQUENCE: 1

atgcttttta atttgaacga tgaggcaaga attattggga tctcagggat gatcggttca      60

gggaaaacca ttcttgccaa ggagcttgcg cgggacgagg aggtccgagg taatcagttt     120

tgccctttgt tatgtctgaa actatccatt gttaatatgc ttgggccatc tttgaagtct     180
```

-continued

```
tttgagcagt ttatgttgtt gctcagtggc atgtttactg gtttatttgg atgatcatgc    240
atttatctct gtatgttcca ttgtgtcatg ttcatctccg gtgaactgtt gatgagtcgt    300
atagttgagt tcttgatatt agaatctgtt aagagtcgga gagactgttc ctttgatgct    360
aaaaaagctt taatacaggc cattttgcga accgagtttt gtttctgact gtgtcacaat    420
ctcccaatct tgaggagctg agatccctta tacgggattt tcttactggt catgaggctg    480
gctttggtac cgctcttccg gaatccgttg gtcatacacg gaagctagtg atccttgatg    540
atgttaggac aagggaatct ctagaccagc tgatgttcaa tattcctgga accacaacgc    600
ttgtggtctc acagtctaaa ctcgtagatc ctagaaccac ctatgatgta gagttattaa    660
atgaacatga cgcaacatct ctgttctgtc tctctgcttt caaccagaaa tcagttcctt    720
cagggttcag caaaagtttg gtcaagcagg taatgggtct gctacaagtg ttacatgcat    780
agtagtaata ttctttgtac tttcagtact catcttgact ctatttgtta ggttgttggg    840
gagtctaaag gtctaccttt gtctctgaaa gtccttggcg cttcattaaa cgatcgacct    900
gaaacatatt gggcaattgc agtggagagg ttatcaagag gtgaacctgt tgatgaaact    960
catgagagta aagtgtttgc tcaaatcgaa gcaactctag aaaatctcga tccaaaaacc   1020
aaagagtgtt tcttggatat gggtgctttc cctgaaggca agaaaatccc tgttgatgtt   1080
ctcatcaaca tgttggtcaa gatacatgat cttgaggacg cagccgcctt tgatgttctt   1140
gttgatctag caaataggaa tcttcttact ctcgtgaaag atccaacgta cggttataga   1200
actctttatg ttctcatctc ttgtagccac ttttataatt ttaaccattc ttaactaatt   1260
taccgtggat aatgttgcag gtttgtcgct atgggcacta gctactatga tatattcgtg   1320
acgcagcacg atgttttaag agatgtagca cttcatctta ccaatcgtgg aaaagtaagt   1380
agaagagacc gcttattgat gccaaaaaga gagaccatgc ttcccagcga atgggagagg   1440
agcaatgatg agccatacaa tgcacgagtg gtttccattc acacaggcaa gaatttgtta   1500
tgcaacgatc ttctaatgaa ttaattcggt tcgtcactag aatcataagg tattaatatg   1560
gatttcttta caggagaaat gactgagatg gactggtttg acatggattt ccccaaggca   1620
gaagttctga tagtaaactt ctcttcagac aactatgtat tgcctccttt cattgctaag   1680
atgggaatgc ttagggtgtt cgtgattata aacaacggta cctctccagc gcatctacat   1740
gacttcccca tccctaccag tttgaccaat ctaaggagtc tctggcttga gagggttcat   1800
gtccctgaac tctctagcag tatgataccc ttgaaaaacc tccacaagct atatctgatt   1860
atttgcaaga tcaataacag ttttgatcag acagccatag acattgccca aatcttccca   1920
aaattgactg atatcacaat agattattgc gatgatcttg cggaactacc ttcgaccatc   1980
tgtggaataa cctctctcaa ctccatcagc ataacaaatt gtcccaacat caaggagtta   2040
ccgaagaata taagtaagct acaagccctt caacttttga ggctatacgc ttgcccagag   2100
ctaaaatctc tgcctgtgga aatctgtgaa ttgccaagac tagtgtatgt cgacatctct   2160
cactgtctca gcctaagttc tcttccggaa aagataggaa atgtaaggac acttgagaaa   2220
atcgacatga gagaatgtag cttatcgagc ataccaagtt ccgcagtttc attgacttcc   2280
ctatgctatg taacatgcta tagagaggct ttgtggatgt ggaaagaggt tgagaaggca   2340
gttcccggac ttcgtattga agctactgaa aaatggttca acatgacttg gcccgacgag   2400
tag                                                                 2403
```

<210> SEQ ID NO 2
<211> LENGTH: 1872

```
<212> TYPE: DNA
<213> ORGANISM: Arabidopsis thaliana
<220> FEATURE:
<221> NAME/KEY: source
<222> LOCATION: 1..1872
<223> OTHER INFORMATION: /organism="Arabidopsis thaliana"
      /mol_type="unassigned DNA"

<400> SEQUENCE: 2

atgcttttta atttgaacga tgaggcaaga attattggga tctcagggat gatcggttca     60

gggaaaacca ttcttgccaa ggagcttgcg cgggacgagg aggtccgagg ccattttgcg    120

aaccgagttt tgtttctgac tgtgtcacaa tctcccaatc ttgaggagct gagatccctt    180

atacgggatt ttcttactgg tcatgaggct ggctttggta ccgctcttcc ggaatccgtt    240

ggtcatacac ggaagctagt gatccttgat gatgttagga caagggaatc tctagaccag    300

ctgatgttca atattcctgg aaccacaacg cttgtggtct cacagtctaa actcgtagat    360

cctagaacca cctatgatgt agagttatta aatgaacatg acgcaacatc tctgttctgt    420

ctctctgctt tcaaccagaa atcagttcct tcagggttca gcaaaagttt ggtcaagcag    480

gttgttgggg agtctaaagg tctacctttg tctctgaaag tccttggcgc ttcattaaac    540

gatcgacctg aaacatattg ggcaattgca gtggagaggt tatcaagagg tgaacctgtt    600

gatgaaactc atgagagtaa agtgtttgct caaatcgaag caactctaga aaatctcgat    660

ccaaaaacca aagagtgttt cttggatatg ggtgctttcc ctgaaggcaa gaaaatccct    720

gttgatgttc tcatcaacat gttggtcaag atacatgatc ttgaggacgc agccgccttt    780

gatgttcttg ttgatctagc aaataggaat cttcttactc tcgtgaaaga tccaacgttt    840

gtcgctatgg gcactagcta ctatgatata ttcgtgacgc agcacgatgt tttaagagat    900

gtagcacttc atcttaccaa tcgtggaaaa gtaagtagaa gagaccgctt attgatgcca    960

aaaagagaga ccatgcttcc cagcgaatgg gagaggagca atgatgagcc atacaatgca   1020

cgagtggttt ccattcacac aggagaaatg actgagatgg actggtttga catggatttc   1080

cccaaggcag aagttctgat agtaaacttc tcttcagaca actatgtatt gcctcctttc   1140

attgctaaga tgggaatgct tagggtgttc gtgattataa acaacggtac ctctccagcg   1200

catctacatg acttccccat ccctaccagt ttgaccaatc taaggagtct ctggcttgag   1260

agggttcatg tccctgaact ctctagcagt atgatacccct tgaaaaacct ccacaagcta   1320

tatctgatta tttgcaagat caataacagt tttgatcaga cagccataga cattgcccaa   1380

atcttcccaa aattgactga tatcacaata gattattgcg atgatcttgc ggaactacct   1440

tcgaccatct gtggaataac ctctctcaac tccatcagca taacaaattg tcccaacatc   1500

aaggagttac cgaagaatat aagtaagcta caagcccttc aacttttgag gctatacgct   1560

tgcccagagc taaaatctct gcctgtggaa atctgtgaat tgccaagact agtgtatgtc   1620

gacatctctc actgtctcag cctaagttct cttccggaaa agataggaaa tgtaaggaca   1680

cttgagaaaa tcgacatgag agaatgtagc ttatcgagca taccaagttc cgcagtttca   1740

ttgacttccc tatgctatgt aacatgctat agagaggctt tgtggatgtg gaaagaggtt   1800

gagaaggcag ttcccggact tcgtattgaa gctactgaaa aatggttcaa catgacttgg   1860

cccgacgagt ag                                                        1872


<210> SEQ ID NO 3
<211> LENGTH: 623
<212> TYPE: PRT
<213> ORGANISM: Arabidopsis thaliana
```

<400> SEQUENCE: 3

Met Leu Phe Asn Leu Asn Asp Glu Ala Arg Ile Ile Gly Ile Ser Gly
1 5 10 15

Met Ile Gly Ser Gly Lys Thr Ile Leu Ala Lys Glu Leu Ala Arg Asp
20 25 30

Glu Glu Val Arg Gly His Phe Ala Asn Arg Val Leu Phe Leu Thr Val
35 40 45

Ser Gln Ser Pro Asn Leu Glu Glu Leu Arg Ser Leu Ile Arg Asp Phe
50 55 60

Leu Thr Gly His Glu Ala Gly Phe Gly Thr Ala Leu Pro Glu Ser Val
65 70 75 80

Gly His Thr Arg Lys Leu Val Ile Leu Asp Asp Val Arg Thr Arg Glu
85 90 95

Ser Leu Asp Gln Leu Met Phe Asn Ile Pro Gly Thr Thr Thr Leu Val
100 105 110

Val Ser Gln Ser Lys Leu Val Asp Pro Arg Thr Thr Tyr Asp Val Glu
115 120 125

Leu Leu Asn Glu His Asp Ala Thr Ser Leu Phe Cys Leu Ser Ala Phe
130 135 140

Asn Gln Lys Ser Val Pro Ser Gly Phe Ser Lys Ser Leu Val Lys Gln
145 150 155 160

Val Val Gly Glu Ser Lys Gly Leu Pro Leu Ser Leu Lys Val Leu Gly
165 170 175

Ala Ser Leu Asn Asp Arg Pro Glu Thr Tyr Trp Ala Ile Ala Val Glu
180 185 190

Arg Leu Ser Arg Gly Glu Pro Val Asp Glu Thr His Glu Ser Lys Val
195 200 205

Phe Ala Gln Ile Glu Ala Thr Leu Glu Asn Leu Asp Pro Lys Thr Lys
210 215 220

Glu Cys Phe Leu Asp Met Gly Ala Phe Pro Glu Gly Lys Lys Ile Pro
225 230 235 240

Val Asp Val Leu Ile Asn Met Leu Val Lys Ile His Asp Leu Glu Asp
245 250 255

Ala Ala Ala Phe Asp Val Leu Val Asp Leu Ala Asn Arg Asn Leu Leu
260 265 270

Thr Leu Val Lys Asp Pro Thr Phe Val Ala Met Gly Thr Ser Tyr Tyr
275 280 285

Asp Ile Phe Val Thr Gln His Asp Val Leu Arg Asp Val Ala Leu His
290 295 300

Leu Thr Asn Arg Gly Lys Val Ser Arg Arg Asp Arg Leu Leu Met Pro
305 310 315 320

Lys Arg Glu Thr Met Leu Pro Ser Glu Trp Glu Arg Ser Asn Asp Glu
325 330 335

Pro Tyr Asn Ala Arg Val Val Ser Ile His Thr Gly Glu Met Thr Glu
340 345 350

Met Asp Trp Phe Asp Met Asp Phe Pro Lys Ala Glu Val Leu Ile Val
355 360 365

Asn Phe Ser Ser Asp Asn Tyr Val Leu Pro Pro Phe Ile Ala Lys Met
370 375 380

Gly Met Leu Arg Val Phe Val Ile Ile Asn Asn Gly Thr Ser Pro Ala
385 390 395 400

His Leu His Asp Phe Pro Ile Pro Thr Ser Leu Thr Asn Leu Arg Ser

```
                405                 410                 415

Leu Trp Leu Glu Arg Val His Val Pro Glu Leu Ser Ser Ser Met Ile
            420                 425                 430

Pro Leu Lys Asn Leu His Lys Leu Tyr Leu Ile Ile Cys Lys Ile Asn
        435                 440                 445

Asn Ser Phe Asp Gln Thr Ala Ile Asp Ile Ala Gln Ile Phe Pro Lys
    450                 455                 460

Leu Thr Asp Ile Thr Ile Asp Tyr Cys Asp Asp Leu Ala Glu Leu Pro
465                 470                 475                 480

Ser Thr Ile Cys Gly Ile Thr Ser Leu Asn Ser Ile Ser Ile Thr Asn
                485                 490                 495

Cys Pro Asn Ile Lys Glu Leu Pro Lys Asn Ile Ser Lys Leu Gln Ala
            500                 505                 510

Leu Gln Leu Leu Arg Leu Tyr Ala Cys Pro Glu Leu Lys Ser Leu Pro
        515                 520                 525

Val Glu Ile Cys Glu Leu Pro Arg Leu Val Tyr Val Asp Ile Ser His
    530                 535                 540

Cys Leu Ser Leu Ser Ser Leu Pro Glu Lys Ile Gly Asn Val Arg Thr
545                 550                 555                 560

Leu Glu Lys Ile Asp Met Arg Glu Cys Ser Leu Ser Ser Ile Pro Ser
                565                 570                 575

Ser Ala Val Ser Leu Thr Ser Leu Cys Tyr Val Thr Cys Tyr Arg Glu
            580                 585                 590

Ala Leu Trp Met Trp Lys Glu Val Glu Lys Ala Val Pro Gly Leu Arg
        595                 600                 605

Ile Glu Ala Thr Glu Lys Trp Phe Asn Met Thr Trp Pro Asp Glu
    610                 615                 620
```

<210> SEQ ID NO 4
<211> LENGTH: 3123
<212> TYPE: DNA
<213> ORGANISM: Arabidopsis thaliana
<220> FEATURE:
<221> NAME/KEY: source
<222> LOCATION: 1..3123
<223> OTHER INFORMATION: /organism="Arabidopsis thaliana"
/mol_type="unassigned DNA"

<400> SEQUENCE: 4

```
acaaactctc attcattaaa ctagtgacta aagtttactt tgctcacaaa agagttgatt     60

taaacgtttt cacaaacacc atccggacgt aaaatgtgta atggaacata catagagacc    120

aaataattat aaatttataa tagataatgc ttctatgtat atgtatgttt gtatgtaaga    180

ttacgtcatc tcaggtgaac tattgttgag tttttgatat tgaacactgg ttaaaagtca    240

ttgagactgt gtctctgatg ctagaaagtc cttcatttga tgctaaaaag actttgggat    300

ccgagttttg tttctgactg tgtcatattt tctgactttg ggaactggat ttaggcaaga    360

ggaaggtgaa ggagatgctt tttaatttga acgatgaggc aagaattatt gggatctcag    420

ggatgatcgg ttcagggaaa accattcttg ccaaggagct tgcgcgggac gaggaggtcc    480

gaggtaatca gttttgccct ttgttatgtc tgaaactatc cattgttaat atgcttgggc    540

catctttgaa gtcttttgag cagtttatgt tgttgctcag tggcatgttt actggtttat    600

ttggatgatc atgcatttat ctctgtatgt tccattgtgt catgttcatc tccggtgaac    660

tgttgatgag tcgtatagtt gagttcttga tattagaatc tgttaagagt cggagagact    720

gttcctttga tgctaaaaaa gctttaatac aggccatttt gcgaaccgag ttttgtttct    780
```

-continued

```
gactgtgtca caatctccca atcttgagga gctgagatcc cttatacggg atttcttac     840
tggtcatgag gctggctttg gtaccgctct tccggaatcc gttggtcata cacggaagct    900
agtgatcctt gatgatgtta ggacaaggga atctctagac cagctgatgt tcaatattcc    960
tggaaccaca acgcttgtgg tctcacagtc taaactcgta gatcctagaa ccacctatga   1020
tgtagagtta ttaaatgaac atgacgcaac atctctgttc tgtctctctg ctttcaacca   1080
gaaatcagtt ccttcagggt tcagcaaaag tttggtcaag caggtaatgg gtctgctaca   1140
agtgttacat gcatagtagt aatattcttt gtactttcag tactcatctt gactctattt   1200
gttaggttgt tggggagtct aaaggtctac ctttgtctct gaaagtcctt ggcgcttcat   1260
taaacgatcg acctgaaaca tattgggcaa ttgcagtgga gaggttatca agaggtgaac   1320
ctgttgatga aactcatgag agtaaagtgt ttgctcaaat cgaagcaact ctagaaaatc   1380
tcgatccaaa aaccaaagag tgtttcttgg atatgggtgc tttccctgaa ggcaagaaaa   1440
tccctgttga tgttctcatc aacatgttgg tcaagataca tgatcttgag gacgcagccg   1500
cctttgatgt tcttgttgat ctagcaaata ggaatcttct tactctcgtg aaagatccaa   1560
cgtacggtta tagaactctt tatgttctca tctcttgtag ccacttttat aattttaacc   1620
attcttaact aatttaccgt ggataatgtt gcaggtttgt cgctatgggc actagctact   1680
atgatatatt cgtgacgcag cacgatgttt taagagatgt agcacttcat cttaccaatc   1740
gtggaaaagt aagtagaaga gaccgcttat tgatgccaaa aagagagacc atgcttccca   1800
gcgaatggga gaggagcaat gatgagccat acaatgcacg agtggtttcc attcacacag   1860
gcaagaattt gttatgcaac gatcttctaa tgaattaatt cggttcgtca ctagaatcat   1920
aaggtattaa tatggatttc tttacaggag aaatgactga gatggactgg tttgacatgg   1980
atttccccaa ggcagaagtt ctgatagtaa acttctcttc agacaactat gtattgcctc   2040
ctttcattgc taagatggga atgcttaggg tgttcgtgat tataaacaac ggtacctctc   2100
cagcgcatct acatgacttc cccatcccta ccagtttgac caatctaagg agtctctggc   2160
ttgagagggt tcatgtccct gaactctcta gcagtatgat acccttgaaa aacctccaca   2220
agctatatct gattatttgc aagatcaata acagttttga tcagacagcc atagacattg   2280
cccaaatctt cccaaaattg actgatatca caatagatta ttgcgatgat cttgcggaac   2340
taccttcgac catctgtgga ataacctctc tcaactccat cagcataaca aattgtccca   2400
acatcaagga gttaccgaag aatataagta agctacaagc ccttcaactt ttgaggctat   2460
acgcttgccc agagctaaaa tctctgcctg tggaaatctg tgaattgcca agactagtgt   2520
atgtcgacat ctctcactgt ctcagcctaa gttctcttcc ggaaaagata ggaaatgtaa   2580
ggacacttga gaaaatcgac atgagagaat gtagcttatc gagcatacca agttccgcag   2640
tttcattgac ttccctatgc tatgtaacat gctatagaga ggctttgtgg atgtggaaag   2700
aggttgagaa ggcagttccc ggacttcgta ttgaagctac tgaaaaatgg ttcaacatga   2760
cttggcccga cgagtagtag gttcttaatt ctccctccga gcttttgaaa atgcatgttg   2820
tattattatt tattaactcg attaggaccc ctgtatgata tacgatttta ttaatacatg   2880
ttttgctctt ataacgtcaa tatataaatt atatgttgat tttaagtatt aaaagtttct   2940
atttggaatc tcaaagatat gtttttaaag attcacttat aagtaataac aaacaaacaa   3000
aaactattta gcttaatggt aaaaagcatg agtctatata gagaagggtt cataatttaa   3060
aattagtttg aatgttgttt gttattaagt gagatacatt ttaaaataat ttagtgagat   3120
```

aaa 3123

<210> SEQ ID NO 5
<211> LENGTH: 2451
<212> TYPE: DNA
<213> ORGANISM: Arabidopsis thaliana
<220> FEATURE:
<221> NAME/KEY: source
<222> LOCATION: 1..2451
<223> OTHER INFORMATION: /organism="Arabidopsis thaliana"
/mol_type="unassigned DNA"

<400> SEQUENCE: 5
tttaggcaag aggaaggtga aggagatgct ttttaatttg aacgatgagg caagaattat 60
tgggatctca gggatgatcg gttcagggaa aaccattctt gccaaggagc ttgcgcggga 120
cgaggaggtc cgaggtaatc agttttgccc tttgttatgt ctgaaactat ccattgttaa 180
tatgcttggg ccatctttga agtcttttga gcagtttatg ttgttgctca gtggcatgtt 240
tactggttta tttggatgat catgcattta tctctgtatg ttccattgtg tcatgttcat 300
ctccggtgaa ctgttgatga gtcgtatagt tgagttcttg atattagaat ctgttaagag 360
tcggagagac tgttcctttg atgctaaaaa agctttaata caggccattt tgcgaaccga 420
gttttgtttc tgactgtgtc acaatctccc aatcttgagg agctgagatc ccttatacgg 480
gattttctta ctggtcatga ggctggcttt ggtaccgctc ttccggaatc cgttggtcat 540
acacggaagc tagtgatcct tgatgatgtt aggacaaggg aatctctaga ccagctgatg 600
ttcaatattc ctggaaccac aacgcttgtg gtctcacagt ctaaactcgt agatcctaga 660
accacctatg atgtagagtt attaaatgaa catgacgcaa catctctgtt ctgtctctct 720
gctttcaacc agaaatcagt tccttcaggg ttcagcaaaa gtttggtcaa gcaggtaatg 780
ggtctgctac aagtgttaca tgcatagtag taatattctt tgtactttca gtactcatct 840
tgactctatt tgttaggttg ttggggagtc taaaggtcta cctttgtctc tgaaagtcct 900
tggcgcttca ttaaacgatc gacctgaaac atattgggca attgcagtgg agaggttatc 960
aagaggtgaa cctgttgatg aaactcatga gagtaaagtg tttgctcaaa tcgaagcaac 1020
tctagaaaat ctcgatccaa aaaccaaaga gtgtttcttg gatatgggtg ctttccctga 1080
aggcaagaaa atccctgttg atgttctcat caacatgttg gtcaagatac atgatcttga 1140
ggacgcagcc gcctttgatg ttcttgttga tctagcaaat aggaatcttc ttactctcgt 1200
gaaagatcca acgtacggtt atagaactct ttatgttctc atctcttgta gccactttta 1260
taattttaac cattcttaac taatttaccg tggataatgt tgcaggtttg tcgctatggg 1320
cactagctac tatgatatat tcgtgacgca gcacgatgtt ttaagagatg tagcacttca 1380
tcttaccaat cgtggaaaag taagtagaag agaccgctta ttgatgccaa aaagagagac 1440
catgcttccc agcgaatggg agaggagcaa tgatgagcca tacaatgcac gagtggtttc 1500
cattcacaca ggcaagaatt tgttatgcaa cgatcttcta atgaattaat tcggttcgtc 1560
actagaatca taaggtatta atatggattt ctttacagga gaaatgactg agatggactg 1620
gtttgacatg gatttcccca aggcagaagt tctgatagta aacttctctt cagacaacta 1680
tgtattgcct cctttcattg ctaagatggg aatgcttagg gtgttcgtga ttataaacaa 1740
cggtacctct ccagcgcatc tacatgactt ccccatccct accagtttga ccaatctaag 1800
gagtctctgg cttgagaggg ttcatgtccc tgaactctct agcagtatga tacccttgaa 1860
aaacctccac aagctatatc tgattatttg caagatcaat aacagttttg atcagacagc 1920
catagacatt gcccaaatct tcccaaaatt gactgatatc acaatagatt attgcgatga 1980
tcttgcggaa ctaccttcga ccatctgtgg aataacctct ctcaactcca tcagcataac 2040
aaattgtccc aacatcaagg agttaccgaa gaatataagt aagctacaag cccttcaact 2100
tttgaggcta tacgcttgcc cagagctaaa atctctgcct gtggaaatct gtgaattgcc 2160
aagactagtg tatgtcgaca tctctcactg tctcagccta agttctcttc cggaaaagat 2220
aggaaatgta aggacacttg agaaaatcga catgagagaa tgtagcttat cgagcatacc 2280
aagttccgca gtttcattga cttccctatg ctatgtaaca tgctatagag aggctttgtg 2340
gatgtggaaa gaggttgaga aggcagttcc cggacttcgt attgaagcta ctgaaaaatg 2400
gttcaacatg acttggcccg acgagtagta ggttcttaat tctccctccg a 2451

<210> SEQ ID NO 6
<211> LENGTH: 21
<212> TYPE: DNA
<213> ORGANISM: Artificial sequence
<220> FEATURE:
<221> NAME/KEY: source
<222> LOCATION: 1..21
<223> OTHER INFORMATION: /organism="Artificial sequence"
/note="HCP5 forward primer"
/mol_type="unassigned DNA"

<400> SEQUENCE: 6
ctggatttag gcaagaggaa g 21

<210> SEQ ID NO 7
<211> LENGTH: 21
<212> TYPE: DNA
<213> ORGANISM: Artificial sequence
<220> FEATURE:
<221> NAME/KEY: source
<222> LOCATION: 1..21
<223> OTHER INFORMATION: /organism="Artificial sequence"
/note="HCP5 reverse primer"
/mol_type="unassigned DNA"

<400> SEQUENCE: 7
gctcggaggg agaattaaga a 21

<210> SEQ ID NO 8
<211> LENGTH: 32
<212> TYPE: DNA
<213> ORGANISM: Artificial sequence
<220> FEATURE:
<221> NAME/KEY: source
<222> LOCATION: 1..32
<223> OTHER INFORMATION: /organism="Artificial sequence"
/note="Forward reamplification primer"
/mol_type="unassigned DNA"

<400> SEQUENCE: 8
tacccgggat gctttttaat ttgaacgatg ag 32

<210> SEQ ID NO 9
<211> LENGTH: 26
<212> TYPE: DNA
<213> ORGANISM: Artificial sequence
<220> FEATURE:
<221> NAME/KEY: source
<222> LOCATION: 1..26
<223> OTHER INFORMATION: /organism="Artificial sequence"
/note="Revese reamplification primer"
/mol_type="unassigned DNA"

<400> SEQUENCE: 9

-continued aaccgcggct actcgtcggg ccaagt 26

<210> SEQ ID NO 10
<211> LENGTH: 2403
<212> TYPE: DNA
<213> ORGANISM: Arabidopsis thaliana
<220> FEATURE:
<221> NAME/KEY: source
<222> LOCATION: 1..2403
<223> OTHER INFORMATION: /organism="Arabidopsis thaliana"
/mol_type="unassigned DNA"

<400> SEQUENCE: 10
atgcttttta atttgaacga tgaggcaaga attattggga tctcagggat gatcggttca 60
gggaaaacca ttcttgccaa ggagcttgcg cgggacgagg aggtccgagg taatcagttt 120
tgccctttgt tatgtctgaa actatccatt gttaatatgc ttgggccatc tttgaagtct 180
tttgagcagt ttatgttgtt gctcagtggc atgtttactg gtttatttgg atgatcatgc 240
atttatctct gtatgttcca ttgtgtcatg ttcatctccg gtgaactgtt gatgagtcgt 300
atagttgagt tcttgatatt agaatctgtt aagagtcgga gagactgttc ctttgatgct 360
aaaaaagctt taatacaggc cattttgcga accgagtttt gtttctgact gtgtcacaat 420
ctcccaatct tgaggagctg agatccctta tacgggattt tcttactggt catgaggctg 480
gctttggtac cgctcttccg gaatccgttg gtcacacacg gaagctagtg atccttgatg 540
atgttaggac aagggaatct ctagaccagc tgatgttcaa tattcctgga accacaacgc 600
ttgtggtctc acagtctaaa ctcgtagatc ctagaaccac ctatgatgta gagttattaa 660
acgaacacga cgcaacatct ctgttctgtc tctctgcttt caaccagaaa tcagttcctt 720
cagggttcag caaaagtttg gtcaagcagg taatgggtct gctacaagtg ttacatgcat 780
agtagtaata ttctttgtac tttcagtact catcttgact ctatttgtta ggttgttggg 840
gagtctaaag gtctaccttt gtctctgaaa gtccttggcg cttcattaaa cgatcgacct 900
gaaacatatt gggcaattgc agtggagagg ttatcaagag gtgaacctgt tgatgaaact 960
catgagagta aagtgtttgc tcaaatcgaa gcaactctag aaaatctcga tccaaaaacc 1020
aaagagtgtt tcttggatat gggtgctttc cctgaaggca agaaaatccc tgttgatgtt 1080
ctgatcaata tgttggtcaa gatacacgat cttgaggacg cagccgcctt tgatgttctt 1140
gttgatctag caaataggaa tcttcttact ctcgtgaaag atccaacgta cggttataga 1200
actctttatg ttctcatctc ttgtagccac ttttataatt ttaaccattc ttaactaatt 1260
taccgtggat aatgttgcag gtttgtcgct atgggcacta gctactatga tatattcgtg 1320
acgcagcacg atgttttaag agatgtagca cttcatctta ccaatcgtgg aaaagtaagt 1380
agaagagacc gcttattgat gccaaaaaga gagaccatgc ttcccagcga atgggagagg 1440
agcaatgatg agccgtacaa tgcacgagtg gtttcgattc acacaggcaa gaatttgtta 1500
tgcaacgatc ttctaatgaa ttaattcggt tcgtcactag aatcataagg tattaatatg 1560
gatttcttta caggagaaat gactgagatg gactggtttg acatggattt ccccaaggca 1620
gaagttctga tagtaaactt ctcttcagac aactatgtat tgcctccttt cattgctaag 1680
atgggaatgc ttagggtgtt cgtgattata aacaacggta cctctccagc gcatctacat 1740
gacttcccga tccctaccag tttgaccaat ctaaggagtc tctggcttga gagggttcat 1800
gtccctgaac tctctagcag tatgataccc ttgaaaaacc tccacaagct atatctgatt 1860
atttgcaaga tcaataacag ttttgatcag acagccatag acattgccca aatcttccca 1920

```
aaattgactg atatcacaat agattattgc gatgatcttg cggaactacc ttcgaccatc   1980

tgtggaataa cctctctcaa ctccatcagc ataacaaatt gtcccaacat caaggagtta   2040

ccgaagaata taagtaagct acaagccctt caacttttga ggctatacgc ttgcccagag   2100

ctaaaatctc tgcctgtgga aatctgtgaa ttgccaagac tagtgtatgt cgacatctct   2160

cactgtctca gcctaagttc tcttccggaa aagataggaa atgtaaggac acttgagaaa   2220

atcgacatga gagaatgtag cttatcgagt ataccaagtt ccgcagtttc tttgacttcc   2280

ctatgctatg taacttgcta tagagaggct ttgtggatgt ggaaagaggt tgagaaggca   2340

gttcccggac ttcgtattga agctactgaa aaatggttca acatgacttg gcccgacgag   2400

tag                                                                 2403
```

<210> SEQ ID NO 11
<211> LENGTH: 829
<212> TYPE: DNA
<213> ORGANISM: Arabidopsis
<220> FEATURE:
<221> NAME/KEY: source
<222> LOCATION: 1..829
<223> OTHER INFORMATION: /organism="Arabidopsis"
/mol_type="unassigned DNA"

<400> SEQUENCE: 11

```
agaaatgact gagatggact ggtttgacat ggatttcccc aaggcagaag ttctgatagt     60

aaacttctct tcagacaact atgtattgcc tcctttcatt gctaagatgg gaatgcttag    120

ggtgttcgtg attataaaca acggtacctc tccagcgcat ctacatgact tccccatccc    180

taccagtttg accaatctaa ggagtctctg gcttgagagg gttcatgtcc ctgaactctc    240

tagcagtatg atacccttga aaaacctcca caagctatat ctgattattt gcaagatcaa    300

taacagtttt gatcagacag ccatagacat tgcccaaatc ttcccaaaat tgactgatat    360

cacaatagat tattgcgatg atcttgcgga actaccttcg accatctgtg gaataacctc    420

tctcaactcc atcagcataa caaattgtcc caacatcaag gagttaccga agaatataag    480

taagctacaa gcccttcaac ttttgaggct atacgcttgc ccagagctaa aatctctgcc    540

tgtggaaatc tgtgaattgc caagactagt gtatgtcgac atctctcact gtctcagcct    600

aagttctctt ccggaaaaga taggaaatgt aaggacactt gagaaaatcg acatgagaga    660

atgtagctta tcgagcatac caagttccgc agtttcattg acttccctat gctatgtaac    720

atgctataga gaggctttgt ggatgtggaa agaggttgag aaggcagttc ccggacttcg    780

tattgaagct actgaaaaat ggttcaacat gacttggccc gacgagtag                829
```

<210> SEQ ID NO 12
<211> LENGTH: 275
<212> TYPE: PRT
<213> ORGANISM: Arabidopsis thaliana

<400> SEQUENCE: 12

```
Glu Met Thr Glu Met Asp Trp Phe Asp Met Asp Phe Pro Lys Ala Glu
1               5                   10                  15

Val Leu Ile Val Asn Phe Ser Ser Asp Asn Tyr Val Leu Pro Pro Phe
            20                  25                  30

Ile Ala Lys Met Gly Met Leu Arg Val Phe Val Ile Ile Asn Asn Gly
        35                  40                  45

Thr Ser Pro Ala His Leu His Asp Phe Pro Ile Pro Thr Ser Leu Thr
    50                  55                  60
```

```
Asn Leu Arg Ser Leu Trp Leu Glu Arg Val His Val Pro Glu Leu Ser
65                  70                  75                  80

Ser Ser Met Ile Pro Leu Lys Asn Leu His Lys Leu Tyr Leu Ile Ile
                85                  90                  95

Cys Lys Ile Asn Asn Ser Phe Asp Gln Thr Ala Ile Asp Ile Ala Gln
            100                 105                 110

Ile Phe Pro Lys Leu Thr Asp Ile Thr Ile Asp Tyr Cys Asp Asp Leu
        115                 120                 125

Ala Glu Leu Pro Ser Thr Ile Cys Gly Ile Thr Ser Leu Asn Ser Ile
    130                 135                 140

Ser Ile Thr Asn Cys Pro Asn Ile Lys Glu Leu Pro Lys Asn Ile Ser
145                 150                 155                 160

Lys Leu Gln Ala Leu Gln Leu Leu Arg Leu Tyr Ala Cys Pro Glu Leu
                165                 170                 175

Lys Ser Leu Pro Val Glu Ile Cys Glu Leu Pro Arg Leu Val Tyr Val
            180                 185                 190

Asp Ile Ser His Cys Leu Ser Leu Ser Ser Leu Pro Glu Lys Ile Gly
        195                 200                 205

Asn Val Arg Thr Leu Glu Lys Ile Asp Met Arg Glu Cys Ser Leu Ser
    210                 215                 220

Ser Ile Pro Ser Ser Ala Val Ser Leu Thr Ser Leu Cys Tyr Val Thr
225                 230                 235                 240

Cys Tyr Arg Glu Ala Leu Trp Met Trp Lys Glu Val Glu Lys Ala Val
                245                 250                 255

Pro Gly Leu Arg Ile Glu Ala Thr Glu Lys Trp Phe Asn Met Thr Trp
            260                 265                 270

Pro Asp Glu
        275
```

<210> SEQ ID NO 13
<211> LENGTH: 2403
<212> TYPE: DNA
<213> ORGANISM: Artificial Sequence
<220> FEATURE:
<221> NAME/KEY: source
<222> LOCATION: 1..2403
<223> OTHER INFORMATION: /organism="Artificial Sequence"
/note="Nucleotide sequence HCP5, variant 1"
/mol_type="unassigned DNA"

<400> SEQUENCE: 13

```
atgctattca acatgaatga cgaagctcgg atcatcggca ttagcggaat gattgggtct     60

ggaaagacta tactcgcgaa agaattggca agagatgaag aagtgcgagg taatcagttt    120

tgccctttgt tatgtctgaa actatccatt gttaatatgc ttgggccatc tttgaagtct    180

tttgagcagt ttatgttgtt gctcagtggc atgtttactg gtttatttgg atgatcatgc    240

atttatctct gtatgttcca ttgtgtcatg ttcatctccg gtgaactgtt gatgagtcgt    300

atagttgagt tcttgatatt agaatctgtt aagagtcgga gagactgttc ctttgatgct    360

aaaaaagctt taatacaggc cattttgcgc acagaattct gcttttagat gtgccataac    420

ttgcctatta tgcgcagtta ggacccgctg tatggcatat ttttgatggt gatgcgcatg    480

gcgatggtgc ccttatttag aaaccctatg gttacccatg gctcgtagtg atcgatgatg    540

atgttgggcc agggaaacct atgaacttcg taatgctcga tctttatgga gcctcagaga    600

atgtggtccc attcgctcaa tagctaaatt ttagagccgc caatgatgta gagctactga    660
```

```
actaatacta cacagcacct ttgctcagta agtatgctaa gcacacgtaa ccaatttctc    720

caagggagtg ccaaggtatg gagtagtagg taatgggtct gctacaagtg ttacatgcat    780

agtagtaata ttctttgtac tttcagtact catcttgact ctatttgtta ggttgtggga    840

gaaagcaagg gccttccgat gagcatgaag gttctgggtg cctccctcaa tgacaggccc    900

gagacctact gggccatcgc tgtcgaacgg ctttctcgcg gcgagcccgt cgacgagacg    960

cacgaatcga aggtcttcgc acagatagag gctaccttag agaaccttga ccccaagaca   1020

aaggaatgct ttatggacat gggcgcattt cccgagggta aaaagatacc ggtcgacgtc   1080

atgattaaca tgatggttaa aattcatgac ttggaagatg cggctgcgtt cgacgtgcta   1140

gtggacttag cgaaccgcaa cctcttaacg ctggtaaagg acccaacgta cggttataga   1200

actctttatg ttctcatctc ttgtagccac ttttataatt ttaaccattc ttaactaatt   1260

taccgtggat aatgttgcag gtttgtggcg atggggacct cgtattacga catctttgtt   1320

actcaacatg acgtcctccg cgacgtcgcc ctacacctga cgaaccgggg taaggtttct   1380

cgtcgcgatc ggctaatgat gccgaagagg gaaacaatgt tgccttccga gtgggaacga   1440

agtaacgacg aaccctataa cgcccgcgta gtgagcatcc atacaggcaa gaatttgtta   1500

tgcaacgatc ttctaatgaa ttaattcggt tcgtcactag aatcataagg tattaatatg   1560

gatttcttta caggagagat gaccgaaatg gattggttcg atatggactt tcctaaagct   1620

gaggtgatga tcgtcaattt tagttccgat aattacgtta tgcccccctt tatagcgaaa   1680

atgggtatgc tacgagtatt tgtaataatc aataatggaa cgtcccctgc acacttgcac   1740

gattttccta taccgacgag catgacaaac cttcgttcac tatggttgga acgagtccac   1800

gttccggagc tgagttccag catgattccg atgaagaatt tacataaact ctacatgatc   1860

atctgtaaaa taaacaattc cttcgaccaa actgcaattg atatcgcaca gatttttcct   1920

aagatgacag acattaccat cgactactgt gacgacttgg cagagctccc gtctactatt   1980

tgcgggatca cgtcattgaa tagcatatcc atcactaact gcccaaatat taaagaacta   2040

cccaaaaaca tttcgaaact ccaggcacta cagctgatgc ggctgtatgc ctgtccggaa   2100

ctcaagagta tgccggttga gatttgcgag atgccccgac tggtttacgt agatatatca   2160

cattgcctat ctttatcgag tttaccagag aaaattggca acgtcagaac tttagaaaag   2220

atagatatgc gcgagtgctc tttgtcatcc atcccgagct ctgcggtgag tatgacatcg   2280

ctgtgttacg ttacatgtta cagggaagca atgtggatgt ggaaggaagt ggaaaaagcc   2340

gtaccggggc tgaggatcga ggccacggag aagtggttta atatgacgtg gccggatgaa   2400

tag                                                                 2403
```

<210> SEQ ID NO 14
<211> LENGTH: 2403
<212> TYPE: DNA
<213> ORGANISM: Artificial Sequence
<220> FEATURE:
<221> NAME/KEY: source
<222> LOCATION: 1..2403
<223> OTHER INFORMATION: /organism="Artificial Sequence"
/note="Nucleotide sequence HCP5, variant 2"
/mol_type="unassigned DNA"

<400> SEQUENCE: 14

```
atgctcttta acatgaatga cgaagcgcgt ataattggga tttcaggtat gattgggtca     60

ggaaagacta tactagcaaa ggaacttgct agagatgaag aagtgcgagg taatcagttt    120

tgccctttgt tatgtctgaa actatccatt gttaatatgc ttgggccatc tttgaagtct    180
```

tttgagcagt ttatgttgtt gctcagtggc atgtttactg gtttatttgg atgatcatgc 240
atttatctct gtatgttcca ttgtgtcatg ttcatctccg gtgaactgtt gatgagtcgt 300
atagttgagt tcttgatatt agaatctgtt aagagtcgga gagactgttc ctttgatgct 360
aaaaaagctt taatacaggc cattttgcga acggagttct gcttttagat gtgccacaac 420
ttacctatta tgcgatcgta agacccttg tatggaatat ttttaatggt gatgagaatg 480
gcgatggttc ccctgtttcg gaacccgatg gtcacacatg gctcttagta atcgatgatg 540
atgcttggcc agggaaacct ttaaacctcg taatgctcaa tatttatgga gcctcagagg 600
atgtggtcgc atagtcttaa tagttagatc ctggagcctc cgatgatgta atcatactaa 660
acaaatacta ctcagcatct ttgcagcgta agcatgttga gtactcgcaa ccaattcctc 720
caaggttcag caaaggtatg gtcctctagg taatgggtct gctacaagtg ttacatgcat 780
agtagtaata ttctttgtac tttcagtact catcttgact ctatttgtta ggttgtcggc 840
gaatcaaagg gccttccgtt gtcgatgaag gtacttgggg ccagtttaaa tgacaggccg 900
gagacctact gggccatagc cgtagaacgt ctcagcaggg gagaacccgt ggacgagacg 960
cacgaaagta aggtgttcgc ccaaatcgag gccaccctag aaaacttgga tcccaaaacg 1020
aaggaatgtt ttatggatat gggggcattt cccgagggaa agaagattcc tgttgacgtt 1080
atgataaaca tgatggtgaa aatccatgac ctggaagatg cggctgcatt cgacgtcctg 1140
gtcgatttag ctaaccggaa cttactcacc cttgttaagg atccaacgta cggttataga 1200
actctttatg ttctcatctc ttgtagccac ttttataatt ttaaccattc ttaactaatt 1260
taccgtggat aatgttgcag gtttgttgcg atgggcacgt cgtattatga catattcgtg 1320
acccagcatg acgtattgcg tgatgtagcc ttacatctca ccaaccgtgg aaaggtgtcg 1380
aggagggacc gcttgatgat gccgaagaga gaaacgatgc ttccttccga gtgggaaagg 1440
tcaaacgacg aaccgtataa cgcacgcgtt gtgagtattc atacaggcaa gaatttgtta 1500
tgcaacgatc ttctaatgaa ttaattcggt tcgtcactag aatcataagg tattaatatg 1560
gatttcttta caggagagat gaccgaaatg gattggttcg atatggattt tcccaaagcg 1620
gaggtaatga ttgtcaattt ttcgagcgat aattacgtta tgccccccatt tatcgcaaaa 1680
atgggcatgc tcagggtatt tgtaatcatt aataatggaa cgtcgccggc tcacctgcac 1740
gactttccaa ttcccacgtc catgacgaac cttagatcgt tgtggctcga acgggttcac 1800
gttccggagt tgtcgtcctc aatgatacct atgaagaatc ttcataaact ttatatgata 1860
atttgcaaaa ttaacaatag cttcgaccaa actgctatag atatcgcaca gatttttccc 1920
aaaatgacgg atattaccat tgactactgt gacgacctag cagagttacc atccacaata 1980
tgcggaatta caagcctgaa ttccatctcg atcacgaact gccctaatat aaaagaattg 2040
cccaagaaca tttccaaact tcaggctttg cagttaatgc gcttatatgc gtgtcctgaa 2100
ctcaagtcca tgcctgttga gatatgcgag atgcctaggt tggtttacgt agatatctca 2160
cattgcctct ctctatcgtc actaccagag aaaataggga atgtgaggac cttagaaaag 2220
atagatatga gagaatgcag tctcagctct ataccgagta gtgccgtctc tatgacatcg 2280
ctgtgttacg ttacctgtta cagggaagcg atgtggatgt ggaaggaagt tgaaaaagca 2340
gtaccaggcc tacgaatcga ggcaacggaa aagtggttta atatgacgtg gccggacgaa 2400
tag 2403

<210> SEQ ID NO 15

<211> LENGTH: 2403
<212> TYPE: DNA
<213> ORGANISM: Artificial Sequence
<220> FEATURE:
<221> NAME/KEY: source
<222> LOCATION: 1..2403
<223> OTHER INFORMATION: /organism="Artificial Sequence"
/note="Nucleotide sequence HCP5, variant 3"
/mol_type="unassigned DNA"

<400> SEQUENCE: 15

```
atgcttttca atatgaatga tgaggcccga ataattggta tttcaggcat gatcgggagc     60

gggaaaacaa ttctagcgaa agaactagca cgtgatgaag aggtccgagg taatcagttt    120

tgccctttgt tatgtctgaa actatccatt gttaatatgc ttgggccatc tttgaagtct    180

tttgagcagt ttatgttgtt gctcagtggc atgtttactg gtttatttgg atgatcatgc    240

atttatctct gtatgttcca ttgtgtcatg ttcatctccg gtgaactgtt gatgagtcgt    300

atagttgagt tcttgatatt agaatctgtt aagagtcgga gagactgttc ctttgatgct    360

aaaaaagctt taatacaggc cattttgaga accgagttct gtttttaact gtgccataac    420

ctccccattt tgaggtcgtg agatccactg tatgggatat ttctcatggt catgcgactg    480

gcattggtac cgctgtttcg gaaccccttg gtaactcatg gatcttagtg atcgatgatg    540

atgttaggtc agggcaatct ttaaactagc tgatgttcaa tcttcctgga accacagaga    600

atgtggtctc atagcttaaa ttcatagatt ctcgagcctc caatgatgta gagttactga    660

acgaatacga ctcaacatct ctgttctgtt tctatgctat ccacgcgaaa tcaattcctc    720

caagggtctg caaaggtttg gtcaagcagg taatgggtct gctacaagtg ttacatgcat    780

agtagtaata ttctttgtac tttcagtact catcttgact ctatttgtta ggttgttggg    840

gagagcaaag gtctacctat gagcatgaag gttcttggag cgtctctcaa cgatcggcct    900

gagacgtatt gggcgatcgc tgtagagagg ctgtcaagag gagaaccggt ggatgagact    960

cacgaatcca aggtgtttgc tcaaatagag gcaacgttag agaacttaga cccaaaaacg   1020

aaggagtgct ttatggacat gggtgcgttt cctgagggaa aaaagattcc ggtggacgtt   1080

atgatcaaca tgatggttaa aatacatgac cttgaggatg cagcggcctt cgacgttctt   1140

gtagacctgg cgaacagaaa ccttctgacg ctcgtcaagg atccaacgta cggttataga   1200

actctttatg ttctcatctc ttgtagccac ttttataatt ttaaccattc ttaactaatt   1260

taccgtggat aatgttgcag gtttgtcgcg atgggtacga gctattacga tatctttgtg   1320

acgcagcacg acgttttgag agacgtagcc ttacatttaa cgaatcgagg gaaggtatca   1380

aggagagacc gccttatgat gcccaaaaga gaaaccatgc ttccttcaga atgggaacga   1440

tcgaacgacg aaccgtacaa cgcacgagtg gtttcaatac atacaggcaa gaatttgtta   1500

tgcaacgatc ttctaatgaa ttaattcggt tcgtcactag aatcataagg tattaatatg   1560

gatttcttta caggagaaat gactgagatg gattggttcg atatggactt cccaaaggcc   1620

gaagtgatga tcgttaactt cagttccgat aactatgttt tgccaccgtt catcgctaaa   1680

atggggatgc ttcgcgtctt cgtgatcata aacaacggaa cttcgccagc tcacctacat   1740

gatttcccta ttccgaccag catgacgaat ttgagatcac tttggcttga aagagttcat   1800

gttcctgaac tcagcagcag tatgattccc ttgaaaaatc tacacaaact ttacatgatt   1860

atttgtaaaa taaataacag cttcgatcaa acggcaatcg atatcgcaca gatttttccc   1920

aagttgacag acataactat agactactgt gacgacctgg cagaactacc aagtacaatt   1980

tgcggtatca cctcgctaaa ctccatatca atcacgaact gtccgaacat taaggaactg   2040
```

-continued ccaaagaaca taagtaagct gcaggcgcta cagcttttgc gcctatatgc ttgtccagag 2100
ctgaagtcga tgcctgttga gatctgtgag atgccaaggc ttgtttacgt agacatctcg 2160
cattgcttat cactatcttc tctcccagag aaaatcggaa acgtgcgtac attagagaag 2220
atagatatga gagagtgctc cctatctagt ataccatcta gtgccgtatc catgactagc 2280
ttgtgctatg tgacgtgcta tcgcgaggcc atgtggatgt ggaaagaagt cgaaaaagca 2340
gttcctgggc ttaggataga ggctactgag aagtggttta acatgacctg gcccgacgaa 2400
tag 2403

<210> SEQ ID NO 16
<211> LENGTH: 2352
<212> TYPE: DNA
<213> ORGANISM: Artificial Sequence
<220> FEATURE:
<221> NAME/KEY: source
<222> LOCATION: 1..2352
<223> OTHER INFORMATION: /organism="Artificial Sequence"
/note="Nucleotide sequence HCP5, variant 4"
/mol_type="unassigned DNA"

<400> SEQUENCE: 16
atgctcttca atttgaacga tgaggctaga ataattggca tcagcgggat gattggatca 60
gggaaaacga tacttgccaa ggaacttgca agagacgagg aggtccgagg taatcagttt 120
tgccctttgt tatgtctgaa actatccatt gttaatatgc ttgggccatc tttgaagtct 180
tttgagcagt ttatgttgtt gctcagtggc atgtttactg gtttatttgg atgatcatgc 240
atttatctct gtatgttcca ttgtgtcatg ttcatctccg gtgaactgtt gatgagtcgt 300
atagttgagt tcttgatatt agaatctgtt aagagtcgga gagactgttc ctttgatgct 360
aaaaaagctt taatacaggc cattttgcga actgagtttt gcttttgact gtgtcataat 420
ttaccaatca tgcggtccta agatccatta tacggtattt ttttaatggt catgaggatg 480
gctatggtac ccctgttccg gaatccgatg gtcactcacg ggagctagtg aagcttgatg 540
atgctgggac aggggaatct ttagacaagc tagtgctcaa tattcctgga accccaacgc 600
ttgtggagcc attctttgaa ttcgtagatc cttgagccgc ctatgatgta gtcgtattaa 660
actaatacaa cgcagcacct ctgttcggtt tctctgctct caaccaggaa tcaatttctc 720
caagggtcag cgaaggtctg gtcatccagg taatgggtct gctacaagtg ttacatgcat 780
agtagtaata ttctttgtac tttcagtact catcttgact ctatttgtta ggttgttgga 840
gagtcaaaag gtctaccttt gtccatgaaa gtcctgggcg ctagcttaaa cgatcgacct 900
gagacctatt gggcaatagc agtggaaagg ctttcaagag gtgaacctgt tgacgaaacg 960
cacgagtcca aagtgtttgc ccagatagag gcaacgcttg aaaaccttga tccaaagacg 1020
aaggagtgtt ttttggatat gggtgctttc cccgagggta aaaagatccc cgtcgatgtt 1080
ctgatcaaca tgttggtcaa aatacatgat cttgaggacg cagccgcctt cgatgttctt 1140
gtcgatcttg caaataggaa ccttcttact ctcgtgaaag atccaacgta cggttataga 1200
actctttatg ttctcatctc ttgtagccac ttttataatt ttaaccattc ttaactaatt 1260
taccgtggat aatgttgcag gtttgtcgct atgggcacaa gctattatga cattttcgtg 1320
actcagcacg atgttttacg ggatgtggca cttcatctta ccaatcgtgg aaaggtatca 1380
cgtagagatc gcctcttgat gcccaaacgc gagacaatgc tacccagcga gtgggagaga 1440
agcaacgacg agccctataa tgctcgagtc gtttccatcc acacaggcaa gaatttgtta 1500

-continued

```
tgcaacgatc ttctaatgaa ttaattcggt tcgtcactag aatcataagg tattaatatg   1560

gatttcttta caggagagat gactgaaatg gattggtttg atatggattt ccccaaagca   1620

gaagtactga tcgtgaattt ctcttcagac aattatgtaa tgccaccatt cattgctaaa   1680

atgggaatgc ttagggtctt tgtgattata aataacggta cgtctccagc gcatctacac   1740

gacttcccga tcccgacgag tttgacaaac ctaaggagtc tctggcttga aagggttcac   1800

gtccctgaac tctcttcgtc aatgataccg atgaaaaacc ttcacaaact atacatgata   1860

atttgtaaga tcaataatag ttttgatcaa acagccatcg acattgctca aatatttcca   1920

aagttgactg atataaccat cgattactgt gacgaccttg cggagttgcc atctaccata   1980

tgtggaataa cctctctgaa ctccatcagt attacaaatt gccccaatat taaagagctc   2040

ccgaagaata tcagtaagct acaagcgcta caactcttga ggctctacgc ttgccctgaa   2100

ctaaaaagca tgcctgtaga gatatgcgag atgcccagac tggtatacgt cgatatatct   2160

cactgtctat cactaagttc cttaccggaa aaaattggca atgtacgcac acttgaaaaa   2220

atcgacatga gagaatgcag cttatcgagt atacctagct ccgcagtttc tatgacatcc   2280

ctatgctacg taacttgcta tcgagaggct atgtggatgt ggaaggaggt tgagaaggca   2340

gttcccggac tt                                                        2352


<210> SEQ ID NO 17
<211> LENGTH: 2403
<212> TYPE: DNA
<213> ORGANISM: Artificial Sequence
<220> FEATURE:
<221> NAME/KEY: source
<222> LOCATION: 1..2403
<223> OTHER INFORMATION: /organism="Artificial Sequence"
      /note="Nucleotide sequence HCP5, variant 5"
      /mol_type="unassigned DNA"

<400> SEQUENCE: 17

atgttattta acatgaacga cgaggcaaga ataattggca tctcagggat gatcggtagc     60

gggaaaacca ttcttgccaa ggagcttgcg cgcgacgagg aagtccgagg taatcagttt    120

tgccctttgt tatgtctgaa actatccatt gttaatatgc ttgggccatc tttgaagtct    180

tttgagcagt ttatgttgtt gctcagtggc atgtttactg gtttatttgg atgatcatgc    240

atttatctct gtatgttcca ttgtgtcatg ttcatctccg gtgaactgtt gatgagtcgt    300

atagttgagt tcttgatatt agaatctgtt aagagtcgga gagactgttc ctttgatgct    360

aaaaaagctt taatacaggc cattttgcgg accgaatttt gtttctgact gtgtcataac    420

ctaccaatta tgaggtcatg agatccctta tacgggatct tcctgatggt catgaggctg    480

gcattggtac cgcttttcag gaatccgttg gttacacatg gaagctaata gagtttgatg    540

atgttaggac aaggcaatct ctgaacctcg tgatgttcaa tattcatgga gccacaacgc    600

ttgtggtctc atagtctaaa ctcgtagatc ttggagcctc ctatgatgta gagctattga    660

acgaacacga cgcaacatct ctgttcagtc tctatgctat caaccagaaa ccagttcctt    720

cagggttcag caaaagtttg gtcgagcagg taatgggtct gctacaagtg ttacatgcat    780

agtagtaata ttctttgtac tttcagtact catcttgact ctatttgtta ggttgttgga    840

gagtctaaag gtctaccctt gtctctgaaa gtcctcggcg cttcattaaa cgaccgtccc    900

gaaacgtatt gggcaatagc agttgaacgc ctatcgagag gtgagccagt cgatgaaact    960

catgaaagta aagtgtttgc tcaaattgaa gcaactctag aaaatttaga tccgaaaacc   1020

aaggagtgtt ttatggatat gggtgccttt cccgagggca aaaaaatacc agtcgatgtt   1080
```

```
ctgatcaaca tgatggtgaa gatacatgac cttgaggatg cagccgcctt tgatgttctg   1140

gttgatctag ctaataggaa tctacttact ctcgtcaaag atccaacgta cggttataga   1200

actctttatg ttctcatctc ttgtagccac ttttataatt ttaaccattc ttaactaatt   1260

taccgtggat aatgttgcag gtttgttgca atggggactt cctattatga tatattcgtc   1320

acgcagcacg atgttttaag agatgtggca cttcacctta cgaatcgtgg gaaagtcagc   1380

agaagagacc ggttattgat gcctaagaga gagaccatgc ttcctagcga atgggaaagg   1440

agcaatgacg agccatataa cgcacgagtg gtaagcatcc atacaggcaa gaatttgtta   1500

tgcaacgatc ttctaatgaa ttaattcggt tcgtcactag aatcataagg tattaatatg   1560

gatttcttta caggagagat gacagagatg gattggtttg acatggattt cccgaaggct   1620

gaggttctga tagtaaattt cagctccgat aactatgtat tgcctccttt catcgctaag   1680

atgggaatgc tgcgcgtctt tgtgattata aacaacggta cctctccagc acatctacat   1740

gactttccga tccctaccag tatgaccaac ctaagaagtc tctggcttga gagggttcac   1800

gtgcccgagc tctccagtag tatgataccc ttgaagaatc ttcacaagtt atacctgatc   1860

atttgtaaaa tcaataacag tttcgatcag acagccatag atattgctca aatcttccca   1920

aagttgactg atatcacaat agattattgc gacgatcttg cggaactacc ttcgaccatc   1980

tgtggaataa cttctctcaa ttccataagc ataaccaatt gtcccaacat taaggagtta   2040

ccaaagaata tatctaagct acaagccctc cagcttatga ggctatacgc ttgcccagag   2100

ctaaaatctc tgccggtaga gatttgcgag ttgccaagac tagtctacgt cgacatctct   2160

cactgcctca gcctaagtag cctaccggag aagataggaa acgtaaggac ccttgaaaaa   2220

atcgacatgc gcgaatgtag cttatcgagt attccatcct ccgcagtttc tttgacttcc   2280

ttatgctacg ttacttgtta tagagaagct atgtggatgt ggaaagaggt tgagaaggca   2340

gtaccaggac tacgtataga agctaccgaa aagtggttca atatgacctg gccggacgaa   2400

tag                                                                 2403
```

<210> SEQ ID NO 18
<211> LENGTH: 2403
<212> TYPE: DNA
<213> ORGANISM: Artificial Sequence
<220> FEATURE:
<221> NAME/KEY: source
<222> LOCATION: 1..2403
<223> OTHER INFORMATION: /organism="Artificial Sequence"
      /note="Nucleotide sequence HCP5, variant 6"
      /mol_type="unassigned DNA"

<400> SEQUENCE: 18

```
atgctgttta acttgaacga tgaggcaaga attattggga tctcagggat gatcggctca     60

gggaaaacca ttcttgccaa ggagcttgcg cgggacgagg aggtccgagg taatcagttt    120

tgccctttgt tatgtctgaa actatccatt gttaatatgc ttgggccatc tttgaagtct    180

tttgagcagt ttatgttgtt gctcagtggc atgtttactg gtttatttgg atgatcatgc    240

atttatctct gtatgttcca ttgtgtcatg ttcatctccg gtgaactgtt gatgagtcgt    300

atagttgagt tcttgatatt agaatctgtt aagagtcgga gagactgttc ctttgatgct    360

aaaaaagctt taatacaggc cattttgcga accgagttct gtttctagct gtgtcacaat    420

ctcccaatca tgaggagctg agatccctta tacggaattt tcttactggt catgaggatg    480

gctttggttc cgctcttccg gaatccgttg gtaacgcacg gaagctagtg atccttgatg    540
```

-continued atgttaggtc aaggaaatct ctagacgtcg tgatgctcaa ttttcctgga accacaaagg 600
atgtggtcac acagtctaaa ttcgtagatc ctggaaccac ctatgatgta gagttattaa 660
acgaacacga cgcaacacct ttgctctgtc agcctgcttt caactagaaa tcagttcctt 720
cagggctcag caaaagtttg gtcaagcagg taatgggtct gctacaagtg ttacatgcat 780
agtagtaata ttctttgtac tttcagtact catcttgact ctatttgtta ggttgttggg 840
gagtctaaag gtctaccctt gtctatgaaa gttcttggag cctcactaaa cgatcgacct 900
gagacatatt gggccattgc ggtggagagg ttaagcagag gtgaacctgt tgatgaaacg 960
cacgaaagta aagtgtttgc tcaaatcgaa gcaactctag aaaatttgga tccaaaaacc 1020
aaagagtgtt tcttggatat gggtgccttc ccggaaggta agaagatccc tgtcgacgtt 1080
ctgatcaata tgttggtcaa gatacacgac cttgaggacg cagccgcctt tgatgtcctt 1140
gtcgatctcg caaatcgtaa tcttcttacg ctcgtgaaag atccaacgta cggttataga 1200
actctttatg ttctcatctc ttgtagccac ttttataatt ttaaccattc ttaactaatt 1260
taccgtggat aatgttgcag gtttgtcgct atgggcactt cttactatga catattcgta 1320
acgcagcacg atgttttacg cgatgtagca cttcatctta cgaatcgtgg aaaagttagc 1380
agaagagacc gtttattgat gccaaaaaga gagaccatgc ttcccagcga gtgggaaagg 1440
agcaatgatg agccttacaa tgcacgagtc gtttctattc acacaggcaa gaatttgtta 1500
tgcaacgatc ttctaatgaa ttaattcggt tcgtcactag aatcataagg tattaatatg 1560
gatttcttta caggagagat gactgagatg gactggttcg atatggattt ccccaaggca 1620
gaagtgctga tcgtaaattt ctcttcagac aactatgtaa tgcctccttt cattgctaag 1680
atgggaatgc ttagggtgtt tgtgattata aacaacggta cctctccagc tcatctacat 1740
gacttcccga ttccaaccag tttgacgaac ctaaggagtc tctggcttga gagggtccat 1800
gtgcctgaac tctctagcag tatgataccc ttgaaaaacc tccacaagct atacctgatt 1860
atttgcaaga ttaataacag ttttgatcag accgccatag acattgccca aatctttccg 1920
aaaatgactg atatcacgat tgactattgc gatgatcttg cggagctacc atcgaccatc 1980
tgtggtataa cttcgctcaa ctccatcagc ataacaaatt gtcccaacat caaggagctc 2040
ccgaagaata taagtaagct acaagccctg caacttatga ggctatacgc ttgtccagaa 2100
ctaaagtcta tgcctgtgga aatctgtgaa atgccaagac tagtatatgt cgacatctct 2160
cattgtctca gcctaagttc acttccggag aagataggca atgtcaggac actggaaaaa 2220
atcgacatga gagagtgtag cttatcgtcg ataccaagtt ccgcagttag catgacgtcc 2280
ctatgctacg taacttgcta tagagaggct ttgtggatgt ggaaagaggt tgagaaagca 2340
gttcccggcc ttcgcattga agctactgaa aaatggttca acatgacttg gcccgacgag 2400
tag 2403

<210> SEQ ID NO 19
<211> LENGTH: 2403
<212> TYPE: DNA
<213> ORGANISM: Artificial Sequence
<220> FEATURE:
<221> NAME/KEY: source
<222> LOCATION: 1..2403
<223> OTHER INFORMATION: /organism="Artificial Sequence"
/note="Nucleotide sequence HCP5, variant 7"
/mol_type="unassigned DNA"

<400> SEQUENCE: 19
atgctattta atttgaacga tgaggcaaga attattggga tctcaggcat gatcggttca 60

-continued

```
gggaaaacca ttctggccaa ggagcttgcg cgggacgaag aggtccgagg taatcagttt    120
tgccctttgt tatgtctgaa actatccatt gttaatatgc ttgggccatc tttgaagtct    180
tttgagcagt ttatgttgtt gctcagtggc atgtttactg gtttatttgg atgatcatgc    240
atttatctct gtatgttcca ttgtgtcatg ttcatctccg gtgaactgtt gatgagtcgt    300
atagttgagt tcttgatatt agaatctgtt aagagtcgga gagactgttc ctttgatgct    360
aaaaaagctt taatacaggc cattttgaga accgagtttt gtttctgact gtgtcataat    420
ctccctatct tgaggagctg agatccctta tacgggattt tcttactggt catgaggctg    480
gctttggtac cgctcttccg gaatccattg gtgacacatg gaagctagtg atccatgatg    540
atgttaggac aagggaatct ctagaccagc tgatgttcaa tattcctgga accacaacgc    600
ttgtggtctc acagtctgaa ctcgtagatc ctagagccac ctatgatgta gagttattaa    660
actaatacga cgcaacatct ctgttctgtc tctctgttat caacccggaa ccagttcctt    720
cagggatccg caaaagtttg gtcaagcagg taatgggtct gctacaagtg ttacatgcat    780
agtagtaata ttctttgtac tttcagtact catcttgact ctatttgtta ggttgttggg    840
gagtctaaag gtctaccttt gtctatgaaa gtccttgggg cgtcattaaa cgatcgacct    900
gaaacgtatt gggcaattgc agtggagagg ttatcaagag gtgagcctgt tgatgaaact    960
catgagagta aagtgtttgc tcaaatcgaa gcaaccctag aaaatctcga tccaaaaacc   1020
aaagagtgct tcatggatat gggtgctttc cctgaaggta agaaaatccc tgttgatgtt   1080
ctgatcaata tgttggtcaa aatccacgat cttgaggacg cagctgcctt tgatgttctt   1140
gttgatctag caaataggaa tcttcttact ctcgtgaaag atccaacgta cggttataga   1200
actctttatg ttctcatctc ttgtagccac ttttataatt ttaaccattc ttaactaatt   1260
taccgtggat aatgttgcag gtttgtagct atgggaacta gctactatga catatttgtg   1320
acccagcacg atgttttaag agatgtagca cttcacctta ccaatcgtgg aaaagtatcc   1380
agaagagacc gcttattgat gccaaaaaga gagaccatgc ttcccagcga atgggagcga   1440
agcaatgatg agccgtataa tgcgcgagtg gtttcgattc atacaggcaa gaatttgtta   1500
tgcaacgatc ttctaatgaa ttaattcggt tcgtcactag aatcataagg tattaatatg   1560
gatttcttta caggagaaat gactgagatg gactggtttg acatggattt ccccaaggca   1620
gaagttctga tagtaaactt ctcttcagac aactatgtat tgcctccatt cattgctaaa   1680
atgggaatgc ttagagtgtt cgtgattata aacaacggga cctctccagc gcatctacat   1740
gacttcccga tccctaccag tttgaccaat ctaaggagtc tctggcttga gagggttcat   1800
gtacctgaac tctctagcag tatgataccc ttgaagaacc tccacaagct atatctgatc   1860
atttgcaaga tcaataacag ttttgatcag acagccatcg acattgccca gatctttcca   1920
aagttgactg atatcacaat agattattgc gatgatcttg cggaactacc ttcgaccatc   1980
tgtggaataa cctctctcaa ttccattagc ataacaaatt gtcccaacat aaaagagtta   2040
ccgaagaaca taagtaagct tcaagccctt caacttttga ggctctacgc ttgcccagag   2100
ctaaaatcta tgcctgtgga aatctgtgaa ttgccaagac tagtttacgt cgacatctct   2160
cactgtctca gcctaagttc tcttccggaa aagataggaa atgtaaggac acttgagaaa   2220
atcgacatga gagaatgtag cttatcgagt atcccaagtt ccgcagtttc tatgacttcc   2280
ttatgctacg taacttgtta tagagaggct ttgtggatgt ggaaggaggt tgagaaggca   2340
gttcccggac ttcgtatcga agccactgaa aaatggttca acatgacttg gcccgacgaa   2400
```

tag 2403

<210> SEQ ID NO 20
<211> LENGTH: 1869
<212> TYPE: DNA
<213> ORGANISM: Artificial Sequence
<220> FEATURE:
<221> NAME/KEY: source
<222> LOCATION: 1..1869
<223> OTHER INFORMATION: /organism="Artificial Sequence"
/note="Nucleotide sequence HCP5, variant 8"
/mol_type="unassigned DNA"

<400> SEQUENCE: 20
atgctgttca acctgaacga cgaggccaga atcatcggca tcagcggcat gatcggcagc 60
ggcaagacca tcctggccaa ggagctggcc agagacgagg aggtgagagg ccacttcgcc 120
aacagagtgc tgttcctgac cgtgagccag agccccaaca tggacgaggg caagagcggc 180
atgaaggact acctgaccgg ccacgaggcc ggcttcgcca ccgccctgcc cgagaccggc 240
ggcagaacca agcacctggt gggcatcgac gaggtgagaa ccagagagac cctggacaac 300
ctgggcttca acctgcccgg caccacctgc ggcgtggtga gccagagcca cgtgatcgac 360
cccagaacca cctacgacgt ggacctgctg aacgagcacg acgccaccag cctgtacagc 420
atcagcgcct tccagcagaa gtgcgtgccc agcatgttca gccacagcat ggtgaagcag 480
ggcgtgggcg acaccaagat cgcccccatg agcatgaaga tgctgggcgc cagcatccag 540
gacaagcccg acacctacta cctgatcgcc gtggagagac tgagcagagg cgagcccgtg 600
gacgagaccc acgagagcaa ggtgttcgcc cagatcgagg ccaccctgga gaacctggac 660
cccaagacca aggagtgctt cctggacatg ggcgccttcc ccgagggcaa gaagatcccc 720
gtggacgtgc tgatcaacat gctggtgaag atccacgacc tggaggacgc cgccgccttc 780
gacgtgctga tggacctggc caacagaaac gccctgaccc tggtgagaga ccccaccttc 840
gtgatgatgg gctgcaccta ctgggacggc tggctgacca accacgacgg cctgagagac 900
gtgatcatga agctgaccca gagaggccac atcagcagaa gagacagagt gctgatgccc 960
agaaaggaga ccctggcccc cagcgagtac gagagatgca acgaggaccc ctaccaggtg 1020
agaatcgtga gcatcagatg catggacatg agcgagatgg actggtacga gatggagttc 1080
cccaaggtgg acatcatcat cctgaacttc agcaccgacc agtacgtgct gccccccttc 1140
atcgtgcaca tggtggtgct gagagtgttc gtggtgatca accaggccac cagccccgtg 1200
cacctgcacg agtaccccat ccccaccagc ctgtgccagg tgagaagcct gtacctggag 1260
agagtgagag tgcccgacgg cagcaccacc atgatcccca tcaagcagct gaagaagctg 1320
ttcctggcca tctgcaaggg ccagaacagc ttcgacaaca ccgccatcga catcgcccag 1380
atctacccca agatgaccga catgagcatc gagtactgcg acgagggcct ggagctgccc 1440
tgcagcatct gcggcgtgag cagcctgcag agcatcagcg ccaccaacac ccccaacgcc 1500
agagacctgc ccaagaacct gagccacctg caggccctga acatgggcaa ggccttcgcc 1560
acccccgagg ccaagagcgg ccccgtggac atctgcgagc tgcccagagc catgtacgtg 1620
gagatctgcc actgcgtgtg cctgagcagc ctgcccgaga agatcggcaa cgtgcactgc 1680
gtggacaaga tcgacatgag agagtgcagc gcctgcagcg gccccagctg cgccgtgagc 1740
ctgagcagcc tgtgctacat caccacctac agagacgccc tgtacatgtg gaaggagatg 1800
gagaaggtgg tgcccatgct gagaatcgag gcctgcgagc actacttcca gatgtgctgg 1860
cccgacgag 1869

<210> SEQ ID NO 21
<211> LENGTH: 623
<212> TYPE: PRT
<213> ORGANISM: Artificial Sequence
<220> FEATURE:
<223> OTHER INFORMATION: Amino acid sequence HCP5, variant 8

<400> SEQUENCE: 21

```
Met Leu Phe Asn Leu Asn Asp Glu Ala Arg Ile Ile Gly Ile Ser Gly
1               5                   10                  15

Met Ile Gly Ser Gly Lys Thr Ile Leu Ala Lys Glu Leu Ala Arg Asp
            20                  25                  30

Glu Glu Val Arg Gly His Phe Ala Asn Arg Val Leu Phe Leu Thr Val
        35                  40                  45

Ser Gln Ser Pro Asn Met Asp Glu Gly Lys Ser Gly Met Lys Asp Tyr
    50                  55                  60

Leu Thr Gly His Glu Ala Gly Phe Ala Thr Ala Leu Pro Glu Thr Gly
65                  70                  75                  80

Gly Arg Thr Lys His Leu Val Gly Ile Asp Glu Val Arg Thr Arg Glu
                85                  90                  95

Thr Leu Asp Asn Leu Gly Phe Asn Leu Pro Gly Thr Thr Cys Gly Val
            100                 105                 110

Val Ser Gln Ser His Val Ile Asp Pro Arg Thr Thr Tyr Asp Val Asp
        115                 120                 125

Leu Leu Asn Glu His Asp Ala Thr Ser Leu Tyr Ser Ile Ser Ala Phe
    130                 135                 140

Gln Gln Lys Cys Val Pro Ser Met Phe Ser His Ser Met Val Lys Gln
145                 150                 155                 160

Gly Val Gly Asp Thr Lys Ile Ala Pro Met Ser Met Lys Met Leu Gly
                165                 170                 175

Ala Ser Ile Gln Asp Lys Pro Asp Thr Tyr Tyr Leu Ile Ala Val Glu
            180                 185                 190

Arg Leu Ser Arg Gly Glu Pro Val Asp Glu Thr His Glu Ser Lys Val
        195                 200                 205

Phe Ala Gln Ile Glu Ala Thr Leu Glu Asn Leu Asp Pro Lys Thr Lys
    210                 215                 220

Glu Cys Phe Leu Asp Met Gly Ala Phe Pro Glu Gly Lys Lys Ile Pro
225                 230                 235                 240

Val Asp Val Leu Ile Asn Met Leu Val Lys Ile His Asp Leu Glu Asp
                245                 250                 255

Ala Ala Ala Phe Asp Val Leu Met Asp Leu Ala Asn Arg Asn Ala Leu
            260                 265                 270

Thr Leu Val Arg Asp Pro Thr Phe Val Met Met Gly Cys Thr Tyr Trp
        275                 280                 285

Asp Gly Trp Leu Thr Asn His Asp Gly Leu Arg Asp Val Ile Met Lys
    290                 295                 300

Leu Thr Gln Arg Gly His Ile Ser Arg Arg Asp Arg Val Leu Met Pro
305                 310                 315                 320

Arg Lys Glu Thr Leu Ala Pro Ser Glu Tyr Glu Arg Cys Asn Glu Asp
                325                 330                 335

Pro Tyr Gln Val Arg Ile Val Ser Ile Arg Cys Met Asp Met Ser Glu
            340                 345                 350

Met Asp Trp Tyr Glu Met Glu Phe Pro Lys Val Asp Ile Ile Ile Leu
        355                 360                 365
```

-continued

```
Asn Phe Ser Thr Asp Gln Tyr Val Leu Pro Pro Phe Ile Val His Met
    370                 375                 380

Val Val Leu Arg Val Phe Val Val Ile Asn Gln Ala Thr Ser Pro Val
385                 390                 395                 400

His Leu His Glu Tyr Pro Ile Pro Thr Ser Leu Cys Gln Val Arg Ser
                405                 410                 415

Leu Tyr Leu Glu Arg Val Arg Val Pro Asp Gly Ser Thr Thr Met Ile
            420                 425                 430

Pro Ile Lys Gln Leu Lys Lys Leu Phe Leu Ala Ile Cys Lys Gly Gln
        435                 440                 445

Asn Ser Phe Asp Asn Thr Ala Ile Asp Ile Ala Gln Ile Tyr Pro Lys
    450                 455                 460

Met Thr Asp Met Ser Ile Glu Tyr Cys Asp Glu Gly Leu Glu Leu Pro
465                 470                 475                 480

Cys Ser Ile Cys Gly Val Ser Ser Leu Gln Ser Ile Ser Ala Thr Asn
                485                 490                 495

Thr Pro Asn Ala Arg Asp Leu Pro Lys Asn Leu Ser His Leu Gln Ala
            500                 505                 510

Leu Asn Met Gly Lys Ala Phe Ala Thr Pro Glu Ala Lys Ser Gly Pro
        515                 520                 525

Val Asp Ile Cys Glu Leu Pro Arg Ala Met Tyr Val Glu Ile Cys His
    530                 535                 540

Cys Val Cys Leu Ser Ser Leu Pro Glu Lys Ile Gly Asn Val His Cys
545                 550                 555                 560

Val Asp Lys Ile Asp Met Arg Glu Cys Ser Ala Cys Ser Gly Pro Ser
                565                 570                 575

Cys Ala Val Ser Leu Ser Ser Leu Cys Tyr Ile Thr Thr Tyr Arg Asp
            580                 585                 590

Ala Leu Tyr Met Trp Lys Glu Met Glu Lys Val Val Pro Met Leu Arg
        595                 600                 605

Ile Glu Ala Cys Glu His Tyr Phe Gln Met Cys Trp Pro Asp Glu
    610                 615                 620


<210> SEQ ID NO 22
<211> LENGTH: 1869
<212> TYPE: DNA
<213> ORGANISM: Artificial Sequence
<220> FEATURE:
<221> NAME/KEY: source
<222> LOCATION: 1..1869
<223> OTHER INFORMATION: /organism="Artificial Sequence"
      /note="Nucleotide sequence HCP5, variant 9"
      /mol_type="unassigned DNA"

<400> SEQUENCE: 22

atgctgttca acctgaacga cgaggccaga atcatcggca tcagcggcat gatcggcagc      60

ggcaagacca tcctggccaa ggagctggcc agagacgagg aggtgagagg ccacttcgcc     120

aacagagtgc tgttcctgac cgtgagccag agcccccaga tggacgagat gaagagcctg     180

atcagagact tcctgaccgg ccacgacgcc ggcttcggca ccgccgcccc cgagaccgtg     240

atccacaccc acaagctggt gatcctggag gaggtgagaa ccaaggagtg cctggaccag     300

ggcatgttcc agatccccgg caccaccacc ctggtgctgt gccagagcaa gctggtggag     360

cccagatgca cctgggacgt ggagctgctg aacgacagag aggtgaccag cctgtggacc     420

ggcagcgcct tcaaccagaa gagcgtgccc tgcggcttct gccacagcat cgtgaagcag     480
```

-continued gtggtgggcg acaccaaggg cctgcccggc tgcctgaagg ccctgggcgc cagcgtgcag 540
gacagacccg agagctactg ggtgatcgcc gtggagagac tgagcagagg cgagcccgtg 600
gacgagaccc acgagagcaa ggtgttcgcc cagatcgagg ccaccctgga gaacctggac 660
cccaagacca aggagtgctt cctggacatg ggcgccttcc ccgagggcaa gaagatcccc 720
gtggacgtgc tgatcaacat gctggtgaag atccacgacc tggaggacgc cgccgccttc 780
gacatgctgg tggaggccct gaaccacaac gtgatctgcc tggtgaagga gcccaccttc 840
gtggccatgg gctgctgcta ctacgacggc ttcctgaccc agaaggacgg cctgagagac 900
gtgggcctga gactgaccaa cagagtgaag gtgtgccaca aggacagaat ggtgatgccc 960
aagagagagt gcatgatccc ctgcgagtgg gagagaagca acgaggagcc ctaccaggcc 1020
agagtggtgt gcatccacac cggcgaggtg accgacatcg actggttcga gatggagttc 1080
cccaaggccg aggtgctgat ggtgaacttc accagcgaca actacgtgct gcccccattc 1140
atcgcccaca tggtggtgct gagactgttc gtgatcgccc agcagggcag ctgccccgcc 1200
aagatgcacg acttcccccct gcccaccagc ggcagcaacc tgcactgcct gtggctggag 1260
cacgcccacg tgcccgagct gtgctgcagc atggtgcccc tgcacaacct gcaccacctg 1320
tacctgatca tcaccaagat caacaacacc tgggaccaga ccgccatcga gatcgcccag 1380
ctgttcccca agctgaccga gatcaccatc gactactgcg acgacctggc cgagctgccc 1440
accaccatct gcggcgcctg cagcctgaac agcatcacca tgaccaactg cccccagatc 1500
aaggacctgc cccacaacat cagcaagatc caggccgccc agctggccag actgtacgcc 1560
acccccgacc tgagaagcct gcccgtggag atctgcgagg tgcccaagct ggtgtacatc 1620
gagctgacca agaccctgag cctgaccagc ctgcccgaga gaatcggcca ggtgagaagc 1680
ctggagaagc tggacatgag agagtgcagc ctgagcagca tccccagcag catggtgagc 1740
ctgacctgcg ccacctacgt gacctgctac agagaggccc tgtgggcctg gaaggaggtg 1800
gagaagatgg cccccggcct gagagtggac ggcaccgaca agtggttcaa catgacctac 1860
cccgaggag 1869

<210> SEQ ID NO 23
<211> LENGTH: 623
<212> TYPE: PRT
<213> ORGANISM: Artificial Sequence
<220> FEATURE:
<223> OTHER INFORMATION: Amino acid sequence HCP5, variant 9

<400> SEQUENCE: 23

Met Leu Phe Asn Leu Asn Asp Glu Ala Arg Ile Ile Gly Ile Ser Gly
1 5 10 15

Met Ile Gly Ser Gly Lys Thr Ile Leu Ala Lys Glu Leu Ala Arg Asp
20 25 30

Glu Glu Val Arg Gly His Phe Ala Asn Arg Val Leu Phe Leu Thr Val
35 40 45

Ser Gln Ser Pro Gln Met Asp Glu Met Lys Ser Leu Ile Arg Asp Phe
50 55 60

Leu Thr Gly His Asp Ala Gly Phe Gly Thr Ala Ala Pro Glu Thr Val
65 70 75 80

Ile His Thr His Lys Leu Val Ile Leu Glu Glu Val Arg Thr Lys Glu
85 90 95

Cys Leu Asp Gln Gly Met Phe Gln Ile Pro Gly Thr Thr Thr Leu Val
100 105 110

-continued

```
Leu Cys Gln Ser Lys Leu Val Glu Pro Arg Cys Thr Trp Asp Val Glu
        115                 120                 125

Leu Leu Asn Asp Arg Glu Val Thr Ser Leu Trp Thr Gly Ser Ala Phe
    130                 135                 140

Asn Gln Lys Ser Val Pro Cys Gly Phe Cys His Ser Ile Val Lys Gln
145                 150                 155                 160

Val Val Gly Asp Thr Lys Gly Leu Pro Gly Cys Leu Lys Ala Leu Gly
                165                 170                 175

Ala Ser Val Gln Asp Arg Pro Glu Ser Tyr Trp Val Ile Ala Val Glu
            180                 185                 190

Arg Leu Ser Arg Gly Glu Pro Val Asp Glu Thr His Glu Ser Lys Val
        195                 200                 205

Phe Ala Gln Ile Glu Ala Thr Leu Glu Asn Leu Asp Pro Lys Thr Lys
    210                 215                 220

Glu Cys Phe Leu Asp Met Gly Ala Phe Pro Glu Gly Lys Lys Ile Pro
225                 230                 235                 240

Val Asp Val Leu Ile Asn Met Leu Val Lys Ile His Asp Leu Glu Asp
                245                 250                 255

Ala Ala Ala Phe Asp Met Leu Val Glu Ala Leu Asn His Asn Val Ile
            260                 265                 270

Cys Leu Val Lys Glu Pro Thr Phe Val Ala Met Gly Cys Cys Tyr Tyr
        275                 280                 285

Asp Gly Phe Leu Thr Gln Lys Asp Gly Leu Arg Asp Val Gly Leu Arg
    290                 295                 300

Leu Thr Asn Arg Val Lys Val Cys His Lys Asp Arg Met Val Met Pro
305                 310                 315                 320

Lys Arg Glu Cys Met Ile Pro Cys Glu Trp Glu Arg Ser Asn Glu Glu
                325                 330                 335

Pro Tyr Gln Ala Arg Val Val Cys Ile His Thr Gly Glu Val Thr Asp
            340                 345                 350

Ile Asp Trp Phe Glu Met Glu Phe Pro Lys Ala Glu Val Leu Met Val
        355                 360                 365

Asn Phe Thr Ser Asp Asn Tyr Val Leu Pro Pro Phe Ile Ala His Met
    370                 375                 380

Val Val Leu Arg Leu Phe Val Ile Ala Gln Gln Gly Ser Cys Pro Ala
385                 390                 395                 400

Lys Met His Asp Phe Pro Leu Pro Thr Ser Gly Ser Asn Leu His Cys
                405                 410                 415

Leu Trp Leu Glu His Ala His Val Pro Glu Leu Cys Cys Ser Met Val
            420                 425                 430

Pro Leu His Asn Leu His His Leu Tyr Leu Ile Ile Thr Lys Ile Asn
        435                 440                 445

Asn Thr Trp Asp Gln Thr Ala Ile Glu Ile Ala Gln Leu Phe Pro Lys
    450                 455                 460

Leu Thr Glu Ile Thr Ile Asp Tyr Cys Asp Asp Leu Ala Glu Leu Pro
465                 470                 475                 480

Thr Thr Ile Cys Gly Ala Cys Ser Leu Asn Ser Ile Thr Met Thr Asn
                485                 490                 495

Cys Pro Gln Ile Lys Asp Leu Pro His Asn Ile Ser Lys Ile Gln Ala
            500                 505                 510

Ala Gln Leu Ala Arg Leu Tyr Ala Thr Pro Asp Leu Arg Ser Leu Pro
        515                 520                 525

Val Glu Ile Cys Glu Val Pro Lys Leu Val Tyr Ile Glu Leu Thr Lys
```

```
    530                 535                 540

Thr Leu Ser Leu Thr Ser Leu Pro Glu Arg Ile Gly Gln Val Arg Ser
545                 550                 555                 560

Leu Glu Lys Leu Asp Met Arg Glu Cys Ser Leu Ser Ser Ile Pro Ser
                565                 570                 575

Ser Met Val Ser Leu Thr Cys Ala Thr Tyr Val Thr Cys Tyr Arg Glu
            580                 585                 590

Ala Leu Trp Ala Trp Lys Glu Val Glu Lys Met Ala Pro Gly Leu Arg
        595                 600                 605

Val Asp Gly Thr Asp Lys Trp Phe Asn Met Thr Tyr Pro Glu Glu
    610                 615                 620


<210> SEQ ID NO 24
<211> LENGTH: 1869
<212> TYPE: DNA
<213> ORGANISM: Artificial Sequence
<220> FEATURE:
<221> NAME/KEY: source
<222> LOCATION: 1..1869
<223> OTHER INFORMATION: /organism="Artificial Sequence"
      /note="Nucleotide sequence HCP5, variant 10"
      /mol_type="unassigned DNA"

<400> SEQUENCE: 24

atgctgttca acctgaacga cgaggccaga atcatcggca tcagcggcat gatcggcagc      60

ggcaagacca tcctggccaa ggagctggcc agagacgagg aggtgagagg ccacttcgcc     120

aacagagtgc tgttcctgac cgtgagccag agccccaacg tggacgagct gagatgcctg     180

atcagagagt tcctgaccgg cagagacgcc ggcttcggca ccgccctgcc cgagagcgtg     240

ggccacacca gaaaggtggt gatcatcgac gacgtgagaa ccagagagag catggagcag     300

gtgatcttcc aggtgcccct gaccaccacc ctggtggtga gccagaccaa gctggtggag     360

cccagaacca ccttcgacgt ggagctgctg aacgagcacg acgccaccag cctgttctgc     420

ctgagcatct tcaacaacaa gagcgtgccc agcggctaca gcagaagcct ggtgagacag     480

atggtgggcg agagcaaggg cctgcccctg agcctgagag tgctggccgc cagcctgaac     540

gacaagcccg agacctactg ggccatcgcc gtggagagac tgagcagagg cgagcccgtg     600

gacgagaccc acgagagcaa ggtgttcgcc cagatcgagg ccaccctgga gaacctggac     660

cccaagacca aggagtgctt cctggacatg ggcgccttcc ccgagggcaa gaagatcccc     720

gtggacgtgc tgatcaacat gctggtgaag atccacgacc tggaggacgc cgccgccttc     780

gacatgctgg tggagctggc caacagaaac ctgctgaccc tggtgaagga ccccaccttc     840

gtggccatga tgaccagcta ctacgacatc ttcgtgacca accacgacct gctgagagag     900

gtggccggcc acatcaccaa cagaggcaga gtgagcagaa gagacagact gctgctgccc     960

agacacgaca ccatgatgcc cagcgagtgg gagaagagca acgaggagcc cttcaacgcc    1020

agagtggtga gcatccacac cggcgacgcc agcgaggccg acttctacga catggacttc    1080

cccaaggccg aggccatcat cgccaactac agcagcgaca actacgtgct gccccccctac    1140

atcgccagac tgggcatgct gaaggtgttc gtgatcatca acaacggcac cacccccgcc    1200

cacctgcacg agttccccat ccccaccagc ctgagcaacc tgagatgcgc ctgggtggag    1260

agagtgcacg tgcccgagct gagcaccagc atggcccccc tgaagcagct gcacaaggtg    1320

tacgccatca tcaccaagat ccagaacagc ttcgaccaga gcgccatcga gatcgcccag    1380

atcttcccca agatgagcga cgccaccatc gactacaccg acgacatggt ggagatcccc    1440
```

-continued

```
agcaccatct gcggcatcac cagcgcccag agcatcagca tcacccagtg ccccaacatg   1500

cacgagctgc ccaagcaggt gagcaagatc caggccgtgc agctgctgag actgtggctg   1560

tgccccgagg tgcactgcct gcccggcgag atctgcgagc tgcccaagct ggtgttcgtg   1620

gacctgagca gatgcctgag cctgagcagc atgcccgaca agatcggcaa cgtgagaacc   1680

atcgagcaca tcgagatgag agagaccagc ggcagcagca tccccagcag cgccctgagc   1740

gccaccagcc tgtgctgggt gaccagctac agagaggccc tgtggatgtt caaggaggtg   1800

gacaaggccg tgcccatcct gagaatcgac gccagcgagc actggttcca gatgacctgg   1860

cccgaggag                                                           1869
```

<210> SEQ ID NO 25
<211> LENGTH: 623
<212> TYPE: PRT
<213> ORGANISM: Artificial Sequence
<220> FEATURE:
<223> OTHER INFORMATION: Amino acid sequence HCP5, variant 10

<400> SEQUENCE: 25

```
Met Leu Phe Asn Leu Asn Asp Glu Ala Arg Ile Ile Gly Ile Ser Gly
1               5                   10                  15

Met Ile Gly Ser Gly Lys Thr Ile Leu Ala Lys Glu Leu Ala Arg Asp
            20                  25                  30

Glu Glu Val Arg Gly His Phe Ala Asn Arg Val Leu Phe Leu Thr Val
        35                  40                  45

Ser Gln Ser Pro Asn Val Asp Glu Leu Arg Cys Leu Ile Arg Glu Phe
    50                  55                  60

Leu Thr Gly Arg Asp Ala Gly Phe Gly Thr Ala Leu Pro Glu Ser Val
65                  70                  75                  80

Gly His Thr Arg Lys Val Val Ile Ile Asp Asp Val Arg Thr Arg Glu
                85                  90                  95

Ser Met Glu Gln Val Ile Phe Gln Val Pro Leu Thr Thr Thr Leu Val
            100                 105                 110

Val Ser Gln Thr Lys Leu Val Glu Pro Arg Thr Thr Phe Asp Val Glu
        115                 120                 125

Leu Leu Asn Glu His Asp Ala Thr Ser Leu Phe Cys Leu Ser Ile Phe
    130                 135                 140

Asn Asn Lys Ser Val Pro Ser Gly Tyr Ser Arg Ser Leu Val Arg Gln
145                 150                 155                 160

Met Val Gly Glu Ser Lys Gly Leu Pro Leu Ser Leu Arg Val Leu Ala
                165                 170                 175

Ala Ser Leu Asn Asp Lys Pro Glu Thr Tyr Trp Ala Ile Ala Val Glu
            180                 185                 190

Arg Leu Ser Arg Gly Glu Pro Val Asp Glu Thr His Glu Ser Lys Val
        195                 200                 205

Phe Ala Gln Ile Glu Ala Thr Leu Glu Asn Leu Asp Pro Lys Thr Lys
    210                 215                 220

Glu Cys Phe Leu Asp Met Gly Ala Phe Pro Glu Gly Lys Lys Ile Pro
225                 230                 235                 240

Val Asp Val Leu Ile Asn Met Leu Val Lys Ile His Asp Leu Glu Asp
                245                 250                 255

Ala Ala Ala Phe Asp Met Leu Val Glu Leu Ala Asn Arg Asn Leu Leu
            260                 265                 270

Thr Leu Val Lys Asp Pro Thr Phe Val Ala Met Met Thr Ser Tyr Tyr
        275                 280                 285
```

```
Asp Ile Phe Val Thr Asn His Asp Leu Leu Arg Glu Val Ala Gly His
    290                 295                 300

Ile Thr Asn Arg Gly Arg Val Ser Arg Arg Asp Arg Leu Leu Leu Pro
305                 310                 315                 320

Arg His Asp Thr Met Met Pro Ser Glu Trp Glu Lys Ser Asn Glu Glu
                325                 330                 335

Pro Phe Asn Ala Arg Val Val Ser Ile His Thr Gly Asp Ala Ser Glu
            340                 345                 350

Ala Asp Phe Tyr Asp Met Asp Phe Pro Lys Ala Glu Ala Ile Ile Ala
        355                 360                 365

Asn Tyr Ser Ser Asp Asn Tyr Val Leu Pro Pro Tyr Ile Ala Arg Leu
    370                 375                 380

Gly Met Leu Lys Val Phe Val Ile Ile Asn Asn Gly Thr Thr Pro Ala
385                 390                 395                 400

His Leu His Glu Phe Pro Ile Pro Thr Ser Leu Ser Asn Leu Arg Cys
                405                 410                 415

Ala Trp Val Glu Arg Val His Val Pro Glu Leu Ser Thr Ser Met Ala
            420                 425                 430

Pro Leu Lys Gln Leu His Lys Val Tyr Ala Ile Ile Thr Lys Ile Gln
        435                 440                 445

Asn Ser Phe Asp Gln Ser Ala Ile Glu Ile Ala Gln Ile Phe Pro Lys
    450                 455                 460

Met Ser Asp Ala Thr Ile Asp Tyr Thr Asp Asp Met Val Glu Ile Pro
465                 470                 475                 480

Ser Thr Ile Cys Gly Ile Thr Ser Ala Gln Ser Ile Ser Ile Thr Gln
                485                 490                 495

Cys Pro Asn Met His Glu Leu Pro Lys Gln Val Ser Lys Ile Gln Ala
            500                 505                 510

Val Gln Leu Leu Arg Leu Trp Leu Cys Pro Glu Val His Cys Leu Pro
        515                 520                 525

Gly Glu Ile Cys Glu Leu Pro Lys Leu Val Phe Val Asp Leu Ser Arg
    530                 535                 540

Cys Leu Ser Leu Ser Ser Met Pro Asp Lys Ile Gly Asn Val Arg Thr
545                 550                 555                 560

Ile Glu His Ile Glu Met Arg Glu Thr Ser Gly Ser Ser Ile Pro Ser
                565                 570                 575

Ser Ala Leu Ser Ala Thr Ser Leu Cys Trp Val Thr Ser Tyr Arg Glu
            580                 585                 590

Ala Leu Trp Met Phe Lys Glu Val Asp Lys Ala Val Pro Ile Leu Arg
        595                 600                 605

Ile Asp Ala Ser Glu His Trp Phe Gln Met Thr Trp Pro Glu Glu
    610                 615                 620
```

<210> SEQ ID NO 26
<211> LENGTH: 1869
<212> TYPE: DNA
<213> ORGANISM: Artificial Sequence
<220> FEATURE:
<221> NAME/KEY: source
<222> LOCATION: 1..1869
<223> OTHER INFORMATION: /organism="Artificial Sequence"
/note="Nucleotide sequence HCP5, variant 11"
/mol_type="unassigned DNA"

<400> SEQUENCE: 26

```
atgctgttca acctgaacga cgaggccaga atcatcggca tcagcggcat gatcggcagc      60
```

```
ggcaagacca tcctggccaa ggagctggcc agagacgagg aggtgagagg ccacttcgcc    120
aacagagtgc tgttcctgac cgtgagccag agccccaacg ccgacgaggc cagaaccctg    180
atcagagact ggctgaccgg caaggacgcc ggctggggca ccgccgtgcc cgagagcggc    240
ggccacacca gaaagctggt gatcctggac gaggtgagat gcagagacag cctggaccag    300
ctgatgttca acatccccgg caccaccacc gccgtggtga gccagagcaa gctggtggac    360
cccagaacct gctacgacgt ggagctgctg aacgagaagg acgccaccag cctgtggtgc    420
ctgtgcgcct tcaaccagaa gagcgtgccc agcggcttca gcaagtgcct ggtgaagcag    480
gtggtgctgg agaccaaggg cctgcccggc agcctgaagg tgctgggcgc cagcctgcag    540
gacagacccg agtgctactg ggccatcgcc gtggagagac tgagcagagg cgagcccgtg    600
gacgagaccc acgagagcaa ggtgttcgcc cagatcgagg ccaccctgga gaacctggac    660
cccaagacca aggagtgctt cctggacatg ggcgccttcc ccgagggcaa gaagatcccc    720
gtggacgtgc tgatcaacat gctggtgaag atccacgacc tggaggacgc cgccgccttc    780
gacgtgctga tggagctggc caacagaaac ctgctgaccc tggtgaagga ccccaccttc    840
gccgccatga tcaccagcta ctgggacatc ttcgtgaccc agaaggacgg cgccagagac    900
gtggccctgc acctgaccca gagaggcaga gtgagcagaa gagacagagt gctggtgccc    960
aagagagaga ccatgctgcc cagcgagtac gagagaagcc aggacgagcc ctacaacgcc   1020
agagtggtga gcatccacac cggcgagatg accgacatgg actggttcga catggacttc   1080
cccaagatgg aggtgctgat cgtgaactgg agcagcgacc agtacgtgct gcccccottc   1140
gccggcaaga tgatgatgct gagagtgttc gtgatcatca acaacggcag cagccccgcc   1200
cacctgcacg actaccccat ccccaccagc ctgaccaacc tgagaagcct gtggatcgac   1260
cacgtgcacg tgcccgagct gagcagcagc ggcatccccc tgagaaacct gcacaagctg   1320
ttcctgatca tcaccaagat caacaacagc ttcgacaaca ccgccatcga catcgcccag   1380
atgttccccc acatcaccga catcaccatc gactacaccg acgacctggc cgagatcccc   1440
agcaccatca gcggcatcac cagcctgaac tgcgccacca tcaccaactg ccccaacatc   1500
aaggagctgc ccaagaacat cagcaagctg aacgccggcc agctgctgag actgttcgcc   1560
tgccccgagc tgaagagcct gcccatggac atctgcgacc tgcccagaat ggtgtacatc   1620
gaggccagcc actgcctgag cctgagcagc atccccgagc acatcggcaa cgtgagaacc   1680
gtggagaaga tcgacatgca cgagtgcagc ctgagcagca tccccagcag cctggtgagc   1740
atcagcagcc tgtgctacat caccagctac aaggaggccc tgtggatgtg gaaggaggtg   1800
gagaaggccg tgcccatcct gagaatcgag gtgaccgagc actggttcaa catgacctgg   1860
cccgaggac                                                           1869
```

<210> SEQ ID NO 27
<211> LENGTH: 623
<212> TYPE: PRT
<213> ORGANISM: Artificial Sequence
<220> FEATURE:
<223> OTHER INFORMATION: Amino acid sequence HCP5, variant 11

<400> SEQUENCE: 27

```
Met Leu Phe Asn Leu Asn Asp Glu Ala Arg Ile Ile Gly Ile Ser Gly
1               5                   10                  15

Met Ile Gly Ser Gly Lys Thr Ile Leu Ala Lys Glu Leu Ala Arg Asp
            20                  25                  30
```

-continued

```
Glu Glu Val Arg Gly His Phe Ala Asn Arg Val Leu Phe Leu Thr Val
        35                  40                  45

Ser Gln Ser Pro Asn Ala Asp Glu Ala Arg Thr Leu Ile Arg Asp Trp
    50                  55                  60

Leu Thr Gly Lys Asp Ala Gly Trp Gly Thr Ala Val Pro Glu Ser Gly
65                  70                  75                  80

Gly His Thr Arg Lys Leu Val Ile Leu Asp Glu Val Arg Cys Arg Asp
                85                  90                  95

Ser Leu Asp Gln Leu Met Phe Asn Ile Pro Gly Thr Thr Thr Ala Val
            100                 105                 110

Val Ser Gln Ser Lys Leu Val Asp Pro Arg Thr Cys Tyr Asp Val Glu
        115                 120                 125

Leu Leu Asn Glu Lys Asp Ala Thr Ser Leu Trp Cys Leu Cys Ala Phe
    130                 135                 140

Asn Gln Lys Ser Val Pro Ser Gly Phe Ser Lys Cys Leu Val Lys Gln
145                 150                 155                 160

Val Val Leu Glu Thr Lys Gly Leu Pro Gly Ser Leu Lys Val Leu Gly
                165                 170                 175

Ala Ser Leu Gln Asp Arg Pro Glu Cys Tyr Trp Ala Ile Ala Val Glu
            180                 185                 190

Arg Leu Ser Arg Gly Glu Pro Val Asp Glu Thr His Glu Ser Lys Val
        195                 200                 205

Phe Ala Gln Ile Glu Ala Thr Leu Glu Asn Leu Asp Pro Lys Thr Lys
    210                 215                 220

Glu Cys Phe Leu Asp Met Gly Ala Phe Pro Glu Gly Lys Lys Ile Pro
225                 230                 235                 240

Val Asp Val Leu Ile Asn Met Leu Val Lys Ile His Asp Leu Glu Asp
                245                 250                 255

Ala Ala Ala Phe Asp Val Leu Met Glu Leu Ala Asn Arg Asn Leu Leu
            260                 265                 270

Thr Leu Val Lys Asp Pro Thr Phe Ala Ala Met Ile Thr Ser Tyr Trp
        275                 280                 285

Asp Ile Phe Val Thr Gln Lys Asp Gly Ala Arg Asp Val Ala Leu His
    290                 295                 300

Leu Thr Gln Arg Gly Arg Val Ser Arg Arg Asp Arg Val Leu Val Pro
305                 310                 315                 320

Lys Arg Glu Thr Met Leu Pro Ser Glu Tyr Glu Arg Ser Gln Asp Glu
                325                 330                 335

Pro Tyr Asn Ala Arg Val Val Ser Ile His Thr Gly Glu Met Thr Asp
            340                 345                 350

Met Asp Trp Phe Asp Met Asp Phe Pro Lys Met Glu Val Leu Ile Val
        355                 360                 365

Asn Trp Ser Ser Asp Gln Tyr Val Leu Pro Pro Phe Ala Gly Lys Met
    370                 375                 380

Met Met Leu Arg Val Phe Val Ile Ile Asn Asn Gly Ser Ser Pro Ala
385                 390                 395                 400

His Leu His Asp Tyr Pro Ile Pro Thr Ser Leu Thr Asn Leu Arg Ser
                405                 410                 415

Leu Trp Ile Asp His Val His Val Pro Glu Leu Ser Ser Ser Gly Ile
            420                 425                 430

Pro Leu Arg Asn Leu His Lys Leu Phe Leu Ile Ile Thr Lys Ile Asn
        435                 440                 445

Asn Ser Phe Asp Asn Thr Ala Ile Asp Ile Ala Gln Met Phe Pro His
```

-continued

```
    450                 455                 460

Ile Thr Asp Ile Thr Ile Asp Tyr Thr Asp Asp Leu Ala Glu Ile Pro
465                 470                 475                 480

Ser Thr Ile Ser Gly Ile Thr Ser Leu Asn Cys Ala Thr Ile Thr Asn
                485                 490                 495

Cys Pro Asn Ile Lys Glu Leu Pro Lys Asn Ile Ser Lys Leu Asn Ala
            500                 505                 510

Gly Gln Leu Leu Arg Leu Phe Ala Cys Pro Glu Leu Lys Ser Leu Pro
        515                 520                 525

Met Asp Ile Cys Asp Leu Pro Arg Met Val Tyr Ile Glu Ala Ser His
    530                 535                 540

Cys Leu Ser Leu Ser Ser Ile Pro Glu His Ile Gly Asn Val Arg Thr
545                 550                 555                 560

Val Glu Lys Ile Asp Met His Glu Cys Ser Leu Ser Ser Ile Pro Ser
                565                 570                 575

Ser Leu Val Ser Ile Ser Ser Leu Cys Tyr Ile Thr Ser Tyr Lys Glu
            580                 585                 590

Ala Leu Trp Met Trp Lys Glu Val Glu Lys Ala Val Pro Ile Leu Arg
        595                 600                 605

Ile Glu Val Thr Glu His Trp Phe Asn Met Thr Trp Pro Glu Asp
    610                 615                 620
```

<210> SEQ ID NO 28
<211> LENGTH: 1869
<212> TYPE: DNA
<213> ORGANISM: Artificial Sequence
<220> FEATURE:
<221> NAME/KEY: source
<222> LOCATION: 1..1869
<223> OTHER INFORMATION: /organism="Artificial Sequence"
/note="Nucleotide sequence HCP5, variant 12"
/mol_type="unassigned DNA"

<400> SEQUENCE: 28

```
atgctgttca acctgaacga cgaggccaga atcatcggca tcagcggcat gatcggcagc     60

ggcaagacca tcctggccaa ggagctggcc agagacgagg aggtgagagg ccacttcgcc    120

aacagagtgc tgttcctgac cgtgagccag agccccaacc tggaggagct gagaagcctg    180

atgagagact tcatcaccgg ccacgagatg ggcttcgcca ccgccctgcc cgagagcatc    240

ggccacacca gaaagctggt gatcctggag gacgtgcaca ccagagagag cctggaccag    300

ctgatgtgga acatccccgg caccaccagc ctggtggtga gccagagcaa gggcatggac    360

cccagaacca cctacgacgt ggagctgctg aacgagcacg acgccaccag cctgttctgc    420

ctgagcgcct tcaaccagaa gagcgtgccc agcggcttca gccacagcct ggtgaagcag    480

gtggtgatgg agaccaaggg cctgcccctg tgcctgaagg tgctgggcgc cagcctgaac    540

gacagacccg agtgctactg ggccatcgcc gtggagagac tgagcagagg cgagcccgtg    600

gacgagaccc acgagagcaa ggtgttcgcc cagatcgagg ccaccctgga gaacctggac    660

cccaagacca aggagtgctt cctggacatg ggcgccttcc ccgagggcaa gaagatcccc    720

gtggacgtgc tgatcaacat gctggtgaag atccacgacc tggaggacgc cgccgccttc    780

gacgtgctgg tggacctggc caacagaaac ctgctgaccc tggtgaagga ccccaccttc    840

gtggccatga tgaccagcta ctacgacatc tgggtgaccc agcacgagct gctgaaggac    900

atggtgctgc acctgaccaa cagaggcaag gtgagcagac acgacagact gctgatgccc    960

aagaaggaga ccatgctgcc cagcgagtgg gagagatgca acgacgaccc ctacaacgcc   1020
```

```
agagtggtga gcatccacac cggcgagatg accgagatgg actggttcga catggacttc   1080

ccccacgccg aggtgctgat cgtgaacttc agctgcgaca actacgtgct gcccccccttc   1140

atcgccaaga tggtgatgct gcacatcttc gtgatcatcc agaacggcac cagccccgcc   1200

cacggccacg acttccccat ccccaccagc ctgaccaacg gcagaagcgg ctggctggag   1260

agaatgcacg tgcccgagct gtgcagcagc atgggcccca tgaagaacct gcacaagctg   1320

tacctggtga tctgcaagat ccagaacagc ttcgaccaga ccgccgccga cgtggcccag   1380

atcttcccca agctgaccga catcaccatc gactactgcg aggacctggc cgagctgccc   1440

agctgcatct gcggcatcac cagcctgaac agcatcagca tgacccagtg ccccaacatc   1500

aaggagctgc ccaagaacat cagcaagctg caggccctga acctgctgag actgtacgcc   1560

tgccccgagc tgaagagcct gcccgtggac atctgcgagc tgcccagact ggtgtacgtg   1620

gacatcagcc actgcctgag cctgagcagc atccccgaca agatcatgaa cgtgagaacc   1680

ggcgagaaga tcgacatgaa ggagtgcagc ctgagcagca tccccagcag cgccgtgagc   1740

ctgaccagcc tgagctgggt gacctgctac agagaggccc tgttcatgtg gaaggaggtg   1800

gagcacgccg tgcccggcct gagaatcgag gccaccgagc actggttcaa catgacctgg   1860

cccgacgag                                                           1869
```

```
<210> SEQ ID NO 29
<211> LENGTH: 623
<212> TYPE: PRT
<213> ORGANISM: Artificial Sequence
<220> FEATURE:
<223> OTHER INFORMATION: Amino acid sequence HCP5, variant 12

<400> SEQUENCE: 29

Met Leu Phe Asn Leu Asn Asp Glu Ala Arg Ile Ile Gly Ile Ser Gly
1               5                   10                  15

Met Ile Gly Ser Gly Lys Thr Ile Leu Ala Lys Glu Leu Ala Arg Asp
            20                  25                  30

Glu Glu Val Arg Gly His Phe Ala Asn Arg Val Leu Phe Leu Thr Val
        35                  40                  45

Ser Gln Ser Pro Asn Leu Glu Glu Leu Arg Ser Leu Met Arg Asp Phe
    50                  55                  60

Ile Thr Gly His Glu Met Gly Phe Ala Thr Ala Leu Pro Glu Ser Ile
65                  70                  75                  80

Gly His Thr Arg Lys Leu Val Ile Leu Glu Asp Val His Thr Arg Glu
                85                  90                  95

Ser Leu Asp Gln Leu Met Trp Asn Ile Pro Gly Thr Thr Ser Leu Val
            100                 105                 110

Val Ser Gln Ser Lys Gly Met Asp Pro Arg Thr Thr Tyr Asp Val Glu
        115                 120                 125

Leu Leu Asn Glu His Asp Ala Thr Ser Leu Phe Cys Leu Ser Ala Phe
    130                 135                 140

Asn Gln Lys Ser Val Pro Ser Gly Phe Ser His Ser Leu Val Lys Gln
145                 150                 155                 160

Val Val Met Glu Thr Lys Gly Leu Pro Leu Cys Leu Lys Val Leu Gly
                165                 170                 175

Ala Ser Leu Asn Asp Arg Pro Glu Cys Tyr Trp Ala Ile Ala Val Glu
            180                 185                 190

Arg Leu Ser Arg Gly Glu Pro Val Asp Glu Thr His Glu Ser Lys Val
        195                 200                 205
```

```
Phe Ala Gln Ile Glu Ala Thr Leu Glu Asn Leu Asp Pro Lys Thr Lys
    210                 215                 220

Glu Cys Phe Leu Asp Met Gly Ala Phe Pro Glu Gly Lys Lys Ile Pro
225                 230                 235                 240

Val Asp Val Leu Ile Asn Met Leu Val Lys Ile His Asp Leu Glu Asp
                245                 250                 255

Ala Ala Ala Phe Asp Val Leu Val Asp Leu Ala Asn Arg Asn Leu Leu
            260                 265                 270

Thr Leu Val Lys Asp Pro Thr Phe Val Ala Met Met Thr Ser Tyr Tyr
        275                 280                 285

Asp Ile Trp Val Thr Gln His Glu Leu Leu Lys Asp Met Val Leu His
    290                 295                 300

Leu Thr Asn Arg Gly Lys Val Ser Arg His Asp Arg Leu Leu Met Pro
305                 310                 315                 320

Lys Lys Glu Thr Met Leu Pro Ser Glu Trp Glu Arg Cys Asn Asp Asp
                325                 330                 335

Pro Tyr Asn Ala Arg Val Val Ser Ile His Thr Gly Glu Met Thr Glu
            340                 345                 350

Met Asp Trp Phe Asp Met Asp Phe Pro His Ala Glu Val Leu Ile Val
        355                 360                 365

Asn Phe Ser Cys Asp Asn Tyr Val Leu Pro Pro Phe Ile Ala Lys Met
    370                 375                 380

Val Met Leu His Ile Phe Val Ile Ile Gln Asn Gly Thr Ser Pro Ala
385                 390                 395                 400

His Gly His Asp Phe Pro Ile Pro Thr Ser Leu Thr Asn Gly Arg Ser
                405                 410                 415

Gly Trp Leu Glu Arg Met His Val Pro Glu Leu Cys Ser Ser Met Gly
            420                 425                 430

Pro Met Lys Asn Leu His Lys Leu Tyr Leu Val Ile Cys Lys Ile Gln
        435                 440                 445

Asn Ser Phe Asp Gln Thr Ala Ala Asp Val Ala Gln Ile Phe Pro Lys
    450                 455                 460

Leu Thr Asp Ile Thr Ile Asp Tyr Cys Glu Asp Leu Ala Glu Leu Pro
465                 470                 475                 480

Ser Cys Ile Cys Gly Ile Thr Ser Leu Asn Ser Ile Ser Met Thr Gln
                485                 490                 495

Cys Pro Asn Ile Lys Glu Leu Pro Lys Asn Ile Ser Lys Leu Gln Ala
            500                 505                 510

Leu Asn Leu Leu Arg Leu Tyr Ala Cys Pro Glu Leu Lys Ser Leu Pro
        515                 520                 525

Val Asp Ile Cys Glu Leu Pro Arg Leu Val Tyr Val Asp Ile Ser His
    530                 535                 540

Cys Leu Ser Leu Ser Ser Ile Pro Asp Lys Ile Met Asn Val Arg Thr
545                 550                 555                 560

Gly Glu Lys Ile Asp Met Lys Glu Cys Ser Leu Ser Ser Ile Pro Ser
                565                 570                 575

Ser Ala Val Ser Leu Thr Ser Leu Ser Trp Val Thr Cys Tyr Arg Glu
            580                 585                 590

Ala Leu Phe Met Trp Lys Glu Val Glu His Ala Val Pro Gly Leu Arg
        595                 600                 605

Ile Glu Ala Thr Glu His Trp Phe Asn Met Thr Trp Pro Asp Glu
    610                 615                 620
```

<210> SEQ ID NO 30
<211> LENGTH: 1869
<212> TYPE: DNA
<213> ORGANISM: Artificial Sequence
<220> FEATURE:
<221> NAME/KEY: source
<222> LOCATION: 1..1869
<223> OTHER INFORMATION: /organism="Artificial Sequence"
/note="Nucleotide sequence HCP5, variant 13"
/mol_type="unassigned DNA"

<400> SEQUENCE: 30
atgctgttca acctgaacga cgaggccaga atcatcggca tcagcggcat gatcggcagc 60
ggcaagacca tcctggccaa ggagctggcc agagacgagg aggtgagagg ccacttcgcc 120
aacagagtgc tgttcctgac cgtgagccag agccccaacc tggaggagct gagaagcctg 180
atcagagact tcctgaccgg ccacgaggcc ggcttcggca ccgccctgcc cgacagcgcc 240
ggccacacca gaagactggt gatcctggac gacgccagaa ccagagagag cctggaccag 300
ctgatgttca acatccccgg caccaccacc ctggtggtga gccagagcaa gctggtggac 360
cccagaacca cctacgacgt ggacatcctg aacgagcacg acgccaccag cctgtactgc 420
ctgagcgcct tcaaccagaa gagcgtgccc agcggctaca gcaagagcct ggtgaagcag 480
gtggtgggcg agaccaaggt gctgcccctg agcctgaagg tgatcggcgc cagcctgaac 540
gacaagcccg agacctactg ggccatcgcc gtggagagac tgagcagagg cgagcccgtg 600
gacgagaccc acgagagcaa ggtgttcgcc cagatcgagg ccaccctgga gaacctggac 660
cccaagacca aggagtgctt cctggacatg ggcgccttcc ccgagggcaa gaagatcccc 720
gtggacgtgc tgatcaacat gctggtgaag atccacgacc tggaggacgc cgccgccttc 780
gacgtgctgg tggacctgct gaacagaaac atgctgaccc tggtgaagga ccccaccttc 840
gtggccatgg gcaccagcta ctacgagatc ttcgtgaccc agcacgaggg cctgcacgac 900
gtggccgcca gactgaccaa caagggcaag gtgagcagaa gagacagagc cctgatgccc 960
aagagagaga ccatgctgcc cagcgagtgg gagagaagca acgacgagcc ctaccaggcc 1020
agagtggtga gcatccacac cggcgagctg accgagatgg actggttcga catggacttc 1080
cccaaggccg aggtgctgat cgtgaactac agcagcgaca acttcgtgct gcccccCttc 1140
atcgccaaga tgggcatgct gagagtgttc ggcatcatca acaacggcac cagccccgcc 1200
cacctgcacg actaccccat ccccaccagc ctgaccaacc tgaagagcct gtggctggag 1260
agagtgcacg tgcccgagct gagcagcagc atgatccccc tgaagaacct gcacaagctg 1320
tggctgatca tctgcaagat caacaacagc tacgaccagt gcgccatcga catcgcccag 1380
atctggccca agctgagcga catcaccatc gactactgcg acgacctggc cgagctgccc 1440
agcaccatct gcatcatcac cagcctgaac agcatcagca tcaccaactg ccccaacatc 1500
aaggagctgc ccaagaacat cagcaagctg caggccctgc agctgctgag actgtgggcc 1560
tgccccgacc tgaagtgcct gcccgtggag atctgcgagc tgcccagact ggtgtacgtg 1620
gacatcagcc actgcgtgtg cctgagcagc ctgcccgaga agatcggcaa cgtgagaacc 1680
ctggagaagc tggacatgca cgactgcacc ctgagcagca tccccagcag cgccgtgagc 1740
atcagcagcc tgtgctacgt gacctgctac agagaggccc tgtggatgtg gaaggaggtg 1800
gagaagctgg tgcccggcct gagaatcgag gccaccgaga agtggttcaa catgacctgg 1860
cccgacgag 1869

<210> SEQ ID NO 31
<211> LENGTH: 623
<212> TYPE: PRT
<213> ORGANISM: Artificial Sequence
<220> FEATURE:
<223> OTHER INFORMATION: Amino acid sequence HCP5, variant 13

<400> SEQUENCE: 31

```
Met Leu Phe Asn Leu Asn Asp Glu Ala Arg Ile Ile Gly Ile Ser Gly
1               5                   10                  15

Met Ile Gly Ser Gly Lys Thr Ile Leu Ala Lys Glu Leu Ala Arg Asp
            20                  25                  30

Glu Glu Val Arg Gly His Phe Ala Asn Arg Val Leu Phe Leu Thr Val
        35                  40                  45

Ser Gln Ser Pro Asn Leu Glu Glu Leu Arg Ser Leu Ile Arg Asp Phe
    50                  55                  60

Leu Thr Gly His Glu Ala Gly Phe Gly Thr Ala Leu Pro Asp Ser Ala
65                  70                  75                  80

Gly His Thr Arg Arg Leu Val Ile Leu Asp Asp Ala Arg Thr Arg Glu
                85                  90                  95

Ser Leu Asp Gln Leu Met Phe Asn Ile Pro Gly Thr Thr Thr Leu Val
            100                 105                 110

Val Ser Gln Ser Lys Leu Val Asp Pro Arg Thr Thr Tyr Asp Val Asp
        115                 120                 125

Ile Leu Asn Glu His Asp Ala Thr Ser Leu Tyr Cys Leu Ser Ala Phe
    130                 135                 140

Asn Gln Lys Ser Val Pro Ser Gly Tyr Ser Lys Ser Leu Val Lys Gln
145                 150                 155                 160

Val Val Gly Glu Thr Lys Val Leu Pro Leu Ser Leu Lys Val Ile Gly
                165                 170                 175

Ala Ser Leu Asn Asp Lys Pro Glu Thr Tyr Trp Ala Ile Ala Val Glu
            180                 185                 190

Arg Leu Ser Arg Gly Glu Pro Val Asp Glu Thr His Glu Ser Lys Val
        195                 200                 205

Phe Ala Gln Ile Glu Ala Thr Leu Glu Asn Leu Asp Pro Lys Thr Lys
    210                 215                 220

Glu Cys Phe Leu Asp Met Gly Ala Phe Pro Glu Gly Lys Lys Ile Pro
225                 230                 235                 240

Val Asp Val Leu Ile Asn Met Leu Val Lys Ile His Asp Leu Glu Asp
                245                 250                 255

Ala Ala Ala Phe Asp Val Leu Val Asp Leu Leu Asn Arg Asn Met Leu
            260                 265                 270

Thr Leu Val Lys Asp Pro Thr Phe Val Ala Met Gly Thr Ser Tyr Tyr
        275                 280                 285

Glu Ile Phe Val Thr Gln His Glu Gly Leu His Asp Val Ala Ala Arg
    290                 295                 300

Leu Thr Asn Lys Gly Lys Val Ser Arg Arg Asp Arg Ala Leu Met Pro
305                 310                 315                 320

Lys Arg Glu Thr Met Leu Pro Ser Glu Trp Glu Arg Ser Asn Asp Glu
                325                 330                 335

Pro Tyr Gln Ala Arg Val Val Ser Ile His Thr Gly Glu Leu Thr Glu
            340                 345                 350

Met Asp Trp Phe Asp Met Asp Phe Pro Lys Ala Glu Val Leu Ile Val
        355                 360                 365

Asn Tyr Ser Ser Asp Asn Phe Val Leu Pro Pro Phe Ile Ala Lys Met
```

```
    370                 375                 380

Gly Met Leu Arg Val Phe Gly Ile Ile Asn Asn Gly Thr Ser Pro Ala
385                 390                 395                 400

His Leu His Asp Tyr Pro Ile Pro Thr Ser Leu Thr Asn Leu Lys Ser
                405                 410                 415

Leu Trp Leu Glu Arg Val His Val Pro Glu Leu Ser Ser Ser Met Ile
            420                 425                 430

Pro Leu Lys Asn Leu His Lys Leu Trp Leu Ile Ile Cys Lys Ile Asn
        435                 440                 445

Asn Ser Tyr Asp Gln Cys Ala Ile Asp Ile Ala Gln Ile Trp Pro Lys
    450                 455                 460

Leu Ser Asp Ile Thr Ile Asp Tyr Cys Asp Asp Leu Ala Glu Leu Pro
465                 470                 475                 480

Ser Thr Ile Cys Ile Ile Thr Ser Leu Asn Ser Ile Ser Ile Thr Asn
                485                 490                 495

Cys Pro Asn Ile Lys Glu Leu Pro Lys Asn Ile Ser Lys Leu Gln Ala
            500                 505                 510

Leu Gln Leu Leu Arg Leu Trp Ala Cys Pro Asp Leu Lys Cys Leu Pro
        515                 520                 525

Val Glu Ile Cys Glu Leu Pro Arg Leu Val Tyr Val Asp Ile Ser His
    530                 535                 540

Cys Val Cys Leu Ser Ser Leu Pro Glu Lys Ile Gly Asn Val Arg Thr
545                 550                 555                 560

Leu Glu Lys Leu Asp Met His Asp Cys Thr Leu Ser Ser Ile Pro Ser
                565                 570                 575

Ser Ala Val Ser Ile Ser Ser Leu Cys Tyr Val Thr Cys Tyr Arg Glu
            580                 585                 590

Ala Leu Trp Met Trp Lys Glu Val Glu Lys Leu Val Pro Gly Leu Arg
        595                 600                 605

Ile Glu Ala Thr Glu Lys Trp Phe Asn Met Thr Trp Pro Asp Glu
    610                 615                 620
```

```
<210> SEQ ID NO 32
<211> LENGTH: 1869
<212> TYPE: DNA
<213> ORGANISM: Artificial Sequence
<220> FEATURE:
<221> NAME/KEY: source
<222> LOCATION: 1..1869
<223> OTHER INFORMATION: /organism="Artificial Sequence"
      /note="Nucleotide sequence HCP5, variant 14"
      /mol_type="unassigned DNA"

<400> SEQUENCE: 32

atgctgttca acctgaacga cgaggccaga atcatcggca tcagcggcat gatcggcagc      60

ggcaagacca tcctggccaa ggagctggcc agagacgagg aggtgagagg ccacttcgcc     120

aacagagtgc tgttcctgac cgtgagccag agccccaacc tggaggagct gagaagcctg     180

atcagagact tcctgaccgg ccacgaggcc ggcttcggca ccgccctgcc cgagagcgtg     240

ggccacacca gaaagctggt gatcctggac gaggtgagaa ccagagagag cctggaccag     300

ctgatgttca acatccccgg caccagcacc ctggtggtga gccagagcaa gctggtggac     360

cccagatgca cctacgacgt ggagctgctg aacgagcacg acgccaccag cctgttctgc     420

ctgagcgcct tcaaccagaa gagcgtgccc agcggcttca gcaagagcct ggtgaagcag     480

gtggtgggcg agagcaaggg cctgcccctg agcctgagag tgctgggcgc cagcctgaac     540
```

-continued gagagacccg agagctactg ggccatcgcc gtggagagac tgagcagagg cgagcccgtg 600
gacgagaccc acgagagcaa ggtgttcgcc cagatcgagg ccaccctgga gaacctggac 660
cccaagacca aggagtgctt cctggacatg ggcgccttcc ccgagggcaa gaagatcccc 720
gtggacgtgc tgatcaacat gctggtgaag atccacgacc tggaggacgc cgccgccttc 780
gacgtgctgg tggacctggg caacagaaac ctgctgaccc tggtgaagga ccccacctgg 840
gtggccatgg gctgcagcta ctacgacatc ttcgtgaccc agaaggacgt gctgagagac 900
gtggccctgc acctgtgcaa cagaggcaag gtgagcagaa gagacagact gctgatgccc 960
aagagagaga ccatgctgcc cagcgagtgg gagagaagca acgacgagcc ctacaacgcc 1020
agaatggtga gcatccacac cggcgagatg accgagatgg actggttcga catggacttc 1080
cccaaggccg aggtgctgat cgtgaacttc agctgcgaga actacgtgct gccccccttc 1140
atcgccaaga tgggcatgct gagagtgttc ggcatcatca acaacggcac cagccccggc 1200
cacctgcacg acttccccat ccccagcagc ctgaccaacc tgagaagcct gtggctggag 1260
agagtgcacg tgcccgagct gtgcagcacc atgatccccc tgaagaacct gcacaagctg 1320
tggctgatca tctgcaagat caaccagagc ttcgaccaga ccgccatcga catcgcccag 1380
atcttcccca agctgaccga catcaccatc gactactgcg acgacctggc cgagctgccc 1440
agcaccatct gcggcatgac cagcatgaac agcatcagca tcaccaactg cccccagctg 1500
aaggagctgc ccaagaacat cagcaagctg cagggcatga acctgctgag actgtacgcc 1560
tgccccgagc tgaagagcat gcccgtggag atctgcgagc tgcccagact ggtgtacgtg 1620
gacatcagcc actgcctgag cctgagcagc ctgcccgaga agatcggcaa cgtgagaacc 1680
ctggagaaga tcgacatgag agagtgcagc ctgagcagca tccccagcag cgccgtgagc 1740
ctgaccagcc tgtgctacat cacctgctac agagaggccc tgtggatgtg gaaggacgtg 1800
gagaaggccg tgcccggcct gagaatcgag gccaccgaga agtggttcaa catgacctgg 1860
cccgacgag 1869

<210> SEQ ID NO 33
<211> LENGTH: 623
<212> TYPE: PRT
<213> ORGANISM: Artificial Sequence
<220> FEATURE:
<223> OTHER INFORMATION: Amino acid sequence HCP5, variant 14

<400> SEQUENCE: 33

Met Leu Phe Asn Leu Asn Asp Glu Ala Arg Ile Ile Gly Ile Ser Gly
1 5 10 15

Met Ile Gly Ser Gly Lys Thr Ile Leu Ala Lys Glu Leu Ala Arg Asp
20 25 30

Glu Glu Val Arg Gly His Phe Ala Asn Arg Val Leu Phe Leu Thr Val
35 40 45

Ser Gln Ser Pro Asn Leu Glu Glu Leu Arg Ser Leu Ile Arg Asp Phe
50 55 60

Leu Thr Gly His Glu Ala Gly Phe Gly Thr Ala Leu Pro Glu Ser Val
65 70 75 80

Gly His Thr Arg Lys Leu Val Ile Leu Asp Glu Val Arg Thr Arg Glu
85 90 95

Ser Leu Asp Gln Leu Met Phe Asn Ile Pro Gly Thr Ser Thr Leu Val
100 105 110

Val Ser Gln Ser Lys Leu Val Asp Pro Arg Cys Thr Tyr Asp Val Glu
115 120 125

-continued

```
Leu Leu Asn Glu His Asp Ala Thr Ser Leu Phe Cys Leu Ser Ala Phe
    130                 135                 140

Asn Gln Lys Ser Val Pro Ser Gly Phe Ser Lys Ser Leu Val Lys Gln
145                 150                 155                 160

Val Val Gly Glu Ser Lys Gly Leu Pro Leu Ser Leu Arg Val Leu Gly
                165                 170                 175

Ala Ser Leu Asn Glu Arg Pro Glu Ser Tyr Trp Ala Ile Ala Val Glu
            180                 185                 190

Arg Leu Ser Arg Gly Glu Pro Val Asp Glu Thr His Glu Ser Lys Val
        195                 200                 205

Phe Ala Gln Ile Glu Ala Thr Leu Glu Asn Leu Asp Pro Lys Thr Lys
    210                 215                 220

Glu Cys Phe Leu Asp Met Gly Ala Phe Pro Glu Gly Lys Lys Ile Pro
225                 230                 235                 240

Val Asp Val Leu Ile Asn Met Leu Val Lys Ile His Asp Leu Glu Asp
                245                 250                 255

Ala Ala Ala Phe Asp Val Leu Val Asp Leu Gly Asn Arg Asn Leu Leu
            260                 265                 270

Thr Leu Val Lys Asp Pro Thr Trp Val Ala Met Gly Cys Ser Tyr Tyr
        275                 280                 285

Asp Ile Phe Val Thr Gln Lys Asp Val Leu Arg Asp Val Ala Leu His
    290                 295                 300

Leu Cys Asn Arg Gly Lys Val Ser Arg Arg Asp Arg Leu Leu Met Pro
305                 310                 315                 320

Lys Arg Glu Thr Met Leu Pro Ser Glu Trp Glu Arg Ser Asn Asp Glu
                325                 330                 335

Pro Tyr Asn Ala Arg Met Val Ser Ile His Thr Gly Glu Met Thr Glu
            340                 345                 350

Met Asp Trp Phe Asp Met Asp Phe Pro Lys Ala Glu Val Leu Ile Val
        355                 360                 365

Asn Phe Ser Cys Glu Asn Tyr Val Leu Pro Pro Phe Ile Ala Lys Met
    370                 375                 380

Gly Met Leu Arg Val Phe Gly Ile Ile Asn Asn Gly Thr Ser Pro Gly
385                 390                 395                 400

His Leu His Asp Phe Pro Ile Pro Ser Ser Leu Thr Asn Leu Arg Ser
                405                 410                 415

Leu Trp Leu Glu Arg Val His Val Pro Glu Leu Cys Ser Thr Met Ile
            420                 425                 430

Pro Leu Lys Asn Leu His Lys Leu Trp Leu Ile Ile Cys Lys Ile Asn
        435                 440                 445

Gln Ser Phe Asp Gln Thr Ala Ile Asp Ile Ala Gln Ile Phe Pro Lys
    450                 455                 460

Leu Thr Asp Ile Thr Ile Asp Tyr Cys Asp Asp Leu Ala Glu Leu Pro
465                 470                 475                 480

Ser Thr Ile Cys Gly Met Thr Ser Met Asn Ser Ile Ser Ile Thr Asn
                485                 490                 495

Cys Pro Gln Leu Lys Glu Leu Pro Lys Asn Ile Ser Lys Leu Gln Gly
            500                 505                 510

Met Asn Leu Leu Arg Leu Tyr Ala Cys Pro Glu Leu Lys Ser Met Pro
        515                 520                 525

Val Glu Ile Cys Glu Leu Pro Arg Leu Val Tyr Val Asp Ile Ser His
    530                 535                 540
```

-continued

Cys Leu Ser Leu Ser Ser Leu Pro Glu Lys Ile Gly Asn Val Arg Thr
545 550 555 560

Leu Glu Lys Ile Asp Met Arg Glu Cys Ser Leu Ser Ser Ile Pro Ser
565 570 575

Ser Ala Val Ser Leu Thr Ser Leu Cys Tyr Ile Thr Cys Tyr Arg Glu
580 585 590

Ala Leu Trp Met Trp Lys Asp Val Glu Lys Ala Val Pro Gly Leu Arg
595 600 605

Ile Glu Ala Thr Glu Lys Trp Phe Asn Met Thr Trp Pro Asp Glu
610 615 620

<210> SEQ ID NO 34
<211> LENGTH: 1869
<212> TYPE: DNA
<213> ORGANISM: Artificial Sequence
<220> FEATURE:
<221> NAME/KEY: source
<222> LOCATION: 1..1869
<223> OTHER INFORMATION: /organism="Artificial Sequence"
/note="Nucleotide sequence HCP5, variant 15"
/mol_type="unassigned DNA"

<400> SEQUENCE: 34
atgctgttca acctgaacga cgaggccaga atcatcggca tcagcggcat gatcggcagc 60
ggcaagacca tcctggccaa ggagctggcc agagacgagg aggtgagagg ccacttcgcc 120
aacagagtgc tgttcctgac cgtgagccag agccccaacc tggaggagct gagaagcctg 180
ggcagagact tcctgaccgg ccacgaggcc ggcttcggca ccgccctgcc cgacagcgtg 240
ggccacacca gaaagctggt gatcctggac gacgtgagaa ccagagagag cctggaccag 300
ctgatgttca acatccccgg caccaccacc ctggtggtga gccagagcaa gctggtggac 360
cccagaacca cctgggacgt ggagctgctg aacgagcacg acgccaccag cctgttctgc 420
ctgagcgcct tcaaccagaa gagcgtgccc accggcttca gcaagagcct ggtgaagcag 480
gtggtgggcg agagcaaggg cctgcccctg agcctgaagg tgctgggcgc cagcctgaac 540
gacagacccg agacctactg ggccatcgcc gtggagagac tgagcagagg cgagcccgtg 600
gacgagaccc acgagagcaa ggtgttcgcc cagatcgagg ccaccctgga gaacctggac 660
cccaagacca aggagtgctt cctggacatg ggcgccttcc ccgagggcaa gaagatcccc 720
gtggacgtgc tgatcaacat gctggtgaag atccacgacc tggaggacgc cgccgccttc 780
gacgtgctgg tggacctggc caacagaaac ctgctgaccc tggtgaagga ccccaccttc 840
gtgggcatgg gcaccagctg gtacgacatc ttcgtgaccc agcacgacgt gctgagagac 900
gtggccctgc acctgaccaa cagaggcaag gtgagcagaa gagacagact gctgatgccc 960
aagagagaga ccatggtgcc cagcgagtgg gagagaagca acgacgagcc ctacaacgcc 1020
agagtggtga gcatccacac cggcgagatg accgaggccg actggttcga catggacttc 1080
cccaaggccg agatcctggc cgtgaacttc agcagcgaca actacgtgct gcccccccttc 1140 atcgccaaga tgggcatgct gagagtgttc gtgatcatca acaacggcac cagccccgcc 1200
cacctgcacg acttccccat ccccaccagc ctgaccaacc tgagaagcct gtggctggag 1260
agagtgcacg tgcccgagct gagcagcagc atgatccccc tgaagaacct gcacaagctg 1320
tacctgatca tctgcaagat caacaacagc ttcgaccaga ccgccatcga catcgcccag 1380
atcttcccca agctgaccga gatcaccatc gactactgcg acgacctggc cgagctgccc 1440
agcaccatct gcggcatcac cagcctgaac agcgtgagca tcaccaactg ccccaacatc 1500

-continued

```
aaggagctgc ccaagaacat cagcaagctg cagggcctgc agctgctgaa gctgtggatc   1560

tgccccgagc tgaagagcct gcccgtggag atctgcgagc tgcccagact ggtgtacgtg   1620

gacatcagcc actgcctgag cctgagcacc ctgcccgaga agatcggcaa cctgagaacc   1680

ctggagaaga tcgacatgag agagtgcagc ctgagcagca tccccagcag cgccgtgagc   1740

ctgaccagcc tgtgctacgt gacctgctac agagaggccc tgtggatgtg gaaggaggtg   1800

gagaaggccg tgcccggcct gagaatcgag gccaccgaga agtggttcaa catgacctgg   1860

cccgacgag                                                            1869


<210> SEQ ID NO 35
<211> LENGTH: 623
<212> TYPE: PRT
<213> ORGANISM: Artificial Sequence
<220> FEATURE:
<223> OTHER INFORMATION: Amino acid sequence HCP5, variant 15

<400> SEQUENCE: 35

Met Leu Phe Asn Leu Asn Asp Glu Ala Arg Ile Ile Gly Ile Ser Gly
1               5                   10                  15

Met Ile Gly Ser Gly Lys Thr Ile Leu Ala Lys Glu Leu Ala Arg Asp
            20                  25                  30

Glu Glu Val Arg Gly His Phe Ala Asn Arg Val Leu Phe Leu Thr Val
        35                  40                  45

Ser Gln Ser Pro Asn Leu Glu Glu Leu Arg Ser Leu Gly Arg Asp Phe
    50                  55                  60

Leu Thr Gly His Glu Ala Gly Phe Gly Thr Ala Leu Pro Asp Ser Val
65                  70                  75                  80

Gly His Thr Arg Lys Leu Val Ile Leu Asp Asp Val Arg Thr Arg Glu
                85                  90                  95

Ser Leu Asp Gln Leu Met Phe Asn Ile Pro Gly Thr Thr Thr Leu Val
            100                 105                 110

Val Ser Gln Ser Lys Leu Val Asp Pro Arg Thr Thr Trp Asp Val Glu
        115                 120                 125

Leu Leu Asn Glu His Asp Ala Thr Ser Leu Phe Cys Leu Ser Ala Phe
    130                 135                 140

Asn Gln Lys Ser Val Pro Thr Gly Phe Ser Lys Ser Leu Val Lys Gln
145                 150                 155                 160

Val Val Gly Glu Ser Lys Gly Leu Pro Leu Ser Leu Lys Val Leu Gly
                165                 170                 175

Ala Ser Leu Asn Asp Arg Pro Glu Thr Tyr Trp Ala Ile Ala Val Glu
            180                 185                 190

Arg Leu Ser Arg Gly Glu Pro Val Asp Glu Thr His Glu Ser Lys Val
        195                 200                 205

Phe Ala Gln Ile Glu Ala Thr Leu Glu Asn Leu Asp Pro Lys Thr Lys
    210                 215                 220

Glu Cys Phe Leu Asp Met Gly Ala Phe Pro Glu Gly Lys Lys Ile Pro
225                 230                 235                 240

Val Asp Val Leu Ile Asn Met Leu Val Lys Ile His Asp Leu Glu Asp
                245                 250                 255

Ala Ala Ala Phe Asp Val Leu Val Asp Leu Ala Asn Arg Asn Leu Leu
            260                 265                 270

Thr Leu Val Lys Asp Pro Thr Phe Val Gly Met Gly Thr Ser Trp Tyr
        275                 280                 285

Asp Ile Phe Val Thr Gln His Asp Val Leu Arg Asp Val Ala Leu His
```

-continued

```
    290                 295                 300

Leu Thr Asn Arg Gly Lys Val Ser Arg Arg Asp Arg Leu Leu Met Pro
305                 310                 315                 320

Lys Arg Glu Thr Met Val Pro Ser Glu Trp Glu Arg Ser Asn Asp Glu
                325                 330                 335

Pro Tyr Asn Ala Arg Val Val Ser Ile His Thr Gly Glu Met Thr Glu
            340                 345                 350

Ala Asp Trp Phe Asp Met Asp Phe Pro Lys Ala Glu Ile Leu Ala Val
        355                 360                 365

Asn Phe Ser Ser Asp Asn Tyr Val Leu Pro Pro Phe Ile Ala Lys Met
    370                 375                 380

Gly Met Leu Arg Val Phe Val Ile Ile Asn Asn Gly Thr Ser Pro Ala
385                 390                 395                 400

His Leu His Asp Phe Pro Ile Pro Thr Ser Leu Thr Asn Leu Arg Ser
                405                 410                 415

Leu Trp Leu Glu Arg Val His Val Pro Glu Leu Ser Ser Ser Met Ile
            420                 425                 430

Pro Leu Lys Asn Leu His Lys Leu Tyr Leu Ile Ile Cys Lys Ile Asn
        435                 440                 445

Asn Ser Phe Asp Gln Thr Ala Ile Asp Ile Ala Gln Ile Phe Pro Lys
    450                 455                 460

Leu Thr Glu Ile Thr Ile Asp Tyr Cys Asp Asp Leu Ala Glu Leu Pro
465                 470                 475                 480

Ser Thr Ile Cys Gly Ile Thr Ser Leu Asn Ser Val Ser Ile Thr Asn
                485                 490                 495

Cys Pro Asn Ile Lys Glu Leu Pro Lys Asn Ile Ser Lys Leu Gln Gly
            500                 505                 510

Leu Gln Leu Leu Lys Leu Trp Ile Cys Pro Glu Leu Lys Ser Leu Pro
        515                 520                 525

Val Glu Ile Cys Glu Leu Pro Arg Leu Val Tyr Val Asp Ile Ser His
    530                 535                 540

Cys Leu Ser Leu Ser Thr Leu Pro Glu Lys Ile Gly Asn Leu Arg Thr
545                 550                 555                 560

Leu Glu Lys Ile Asp Met Arg Glu Cys Ser Leu Ser Ser Ile Pro Ser
                565                 570                 575

Ser Ala Val Ser Leu Thr Ser Leu Cys Tyr Val Thr Cys Tyr Arg Glu
            580                 585                 590

Ala Leu Trp Met Trp Lys Glu Val Glu Lys Ala Val Pro Gly Leu Arg
        595                 600                 605

Ile Glu Ala Thr Glu Lys Trp Phe Asn Met Thr Trp Pro Asp Glu
    610                 615                 620
```

FUNGAL RESISTANT PLANTS EXPRESSING HCP5

This application is a National Stage application of International Application No. PCT/IB2013/056244, filed Jul. 30, 2013, which claims the benefit of U.S. Provisional Application No. 61/681,162, filed Aug. 9, 2012, the entire contents of which are hereby incorporated herein by reference. This application also claims priority under 35 U.S.C. § 119 to European Patent Application No. 12179862.3, filed Aug. 9, 2012, the entire contents of which are incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Sequence_List.txt" created on Nov. 25, 2014, and is 114,688 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the order Pucciniales, for example soybean rust, in plants, plant parts, and/or plant cells. This is achieved by increasing the expression and/or activity of an HCP5 protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the order Pucciniales, for example soybean rust, and to recombinant expression vectors comprising a sequence that is identical or homologous to a sequence encoding an HCP5 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenic organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects).

Another more specific resistance mechanism is based on the presence of so called resistance genes (R-genes). Most R genes belong to the nucleotide-binding site-leucine-rich repeat (NBS-LRR) gene family and function in monitoring the presence of pathogen effector proteins (virulence factors; avirulence factors). After recognizing the pathogen derived proteins a strong defense reaction (mostly accompanied by a programmed cell death) is elicited.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora*. The necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races. Therefore there is a strong need to discover R-genes that are derived from non-hosts plants (e.g. *Arabidopsis*) as they are thought to be more durable.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that fungal pathogens, in particular of the Phakopsoorder Pucciniales, for example soybean rust, can be controlled by increasing the expression of an HCP5 protein.

The present invention therefore provides a method of increasing resistance against fungal pathogens, preferably against rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more HCP5 nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous HCP5 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that resistance against fungal pathogens, in particular of the Phakopsoorder Pucciniales, for example soybean rust, can be enhanced by increasing the expression of a HCP5 protein.

The present invention therefore provides a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more HCP5 nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous HCP5 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 3 shows the full-length-sequence of the HCP5 gene from *Arabidopsis thaliana* having SEQ ID NO: 1.

FIG. 4 shows the sequence of a HCP5 cDNA (accession No NM_124099) having SEQ ID NO: 2 as derived by bioinformatics from the genomic HCP5 full-length sequence.

FIG. 5 shows the sequence of a HCP5 protein (SEQ ID NO: 3).

FIG. 6 shows the sequence of the genomic sequence (part of accession No NC_003076.8) from *Arabidopsis thaliana* around the region which codes for HCP5 and having SEQ ID NO: 4.

In FIG. 7 the genome sequence (SEQ ID NO: 4) is truncated at its 3' and 5' end. The truncated genome sequence is shown in SEQ ID NO: 5.

FIG. 8 shows the result of the scoring of 50 transgenic soy plants (derived from 5 independent events, 10 plants per event) expressing the HCP5 overexpression vector construct. $T_1$ soybean plants expressing HCP5 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 50 soybean $T_1$ plants expressing HCP5 (expression checked by RT-PCR) were evaluated in parallel to non-transgenic control plants. The average of the diseased leaf area is shown in FIG. 8. Overexpression of HCP5 significantly (*: $p<0.05$) reduces the diseased leaf area in comparison to non-transgenic control plants by 25.1%.

FIG. 9 contains a brief description of the sequences of the sequence listing.

DETAILED DESCRIPTION OF THE INVENTION

Figure 1:
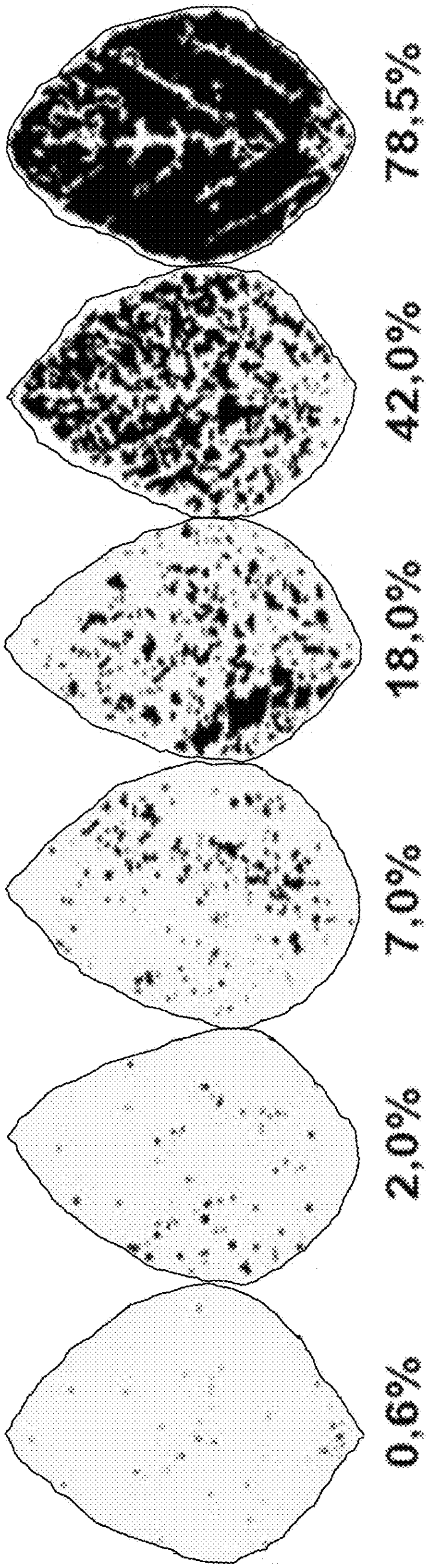
FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular, homologues of a nucleic acid may encompass substitutions on the basis of the degenerative amino acid code.

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides in a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below, or Taylor W. R. (1986) The classification of amino acid conservation J Theor Biol., 119:205-18).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by noncoding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29. MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

As used herein the terms “fungal-resistance”, “resistant to a fungus” and/or “fungal-resistant” mean reducing, preventing, or delaying an infection by fungi. The term “resistance” refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms “soybean rust-resistance”, “resistant to a soybean rust”, “soybean rust-resistant”, “rust-resistance”, “resistant to a rust”, or “rust-resistant” mean reducing or preventing or delaying an infection of a plant, plant part, or plant cell by Phakopsoraceae, in particular *Phakopsora pachyrhizi* and *Phakopsora meibomiae*—also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous HCP5 nucleic acid, functional fragments thereof and/or an exogenous nucleic acid capable of hybridizing with an HCP5 nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term “hybridization” as used herein includes “any process by which a strand of nucleic acid molecule joins with a complementary strand through base pairing” (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term “Tm” is used in reference to the “melting temperature.” The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41 (% G+C), when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term “stringency conditions” refers to conditions, wherein 100 contigous nucleotides or more, 150 contigous nucleotides or more, 200 contigous nucleotides or more or 250 contigous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole HCP5 nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

“Identity” or “homology” or “similarity” between two nucleic acids sequences or amino acid sequences refers in each case over the entire length of the HCP5 nucleic acid sequences or HCP5 amino acid sequences. The terms “identity”, “homology” and “similarity” are used herein interchangeably.

Preferably, “percentage of sequence identity” is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:

Multiple Alignment Parameter:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise Alignment Parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid or protein useful according to the present invention and the HCP5 nucleic acids or HCP5 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous HCP5 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous HCP5 nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more HCP5 nucleic acids, all those constructions brought about by man by genetechnological methods in which either (a) the sequences of the HCP5 nucleic acids or a part thereof, or
(b) genetic control sequence(s) which is operably linked with the HCP5 nucleic acid sequence according to the invention, for example a promoter, or
(c) a) and b)

are not located in their natural genetic environment or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

A recombinant nucleic acid, expression cassette or vector construct preferably comprises a natural gene and a natural promoter, a natural gene and a non-natural promoter, a non-natural gene and a natural promoter, or a non-natural gene and a non-natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation.

The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous HCP5 nucleic acid, recombinant construct, vector or expression cassette including one or more HCP5 nucleic acids is integrated into the genome by means of genetechnology.

Preferably, constructs or vectors or expression cassettes are not present in the genome of the original plant or are present in the genome of the transgenic plant not at their natural locus of the genome of the original plant.

A "wild type" plant, "wild type" plant part, or "wild type" plant cell means that said plant, plant part, or plant cell does not express exogenous HCP5 nucleic acid or exogenous HCP5 protein.

Natural locus means the location on a specific chromosome, preferably the location between certain genes, more preferably the same sequence background as in the original plant which is transformed.

Preferably, the transgenic plant, plant cell or tissue thereof expresses the HCP5 nucleic acids, HCP5 constructs or HCP5 expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid or protein which comprises merely a part of the full length nucleic acid or full length protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the HCP5 nucleic acids has an identity as defined above over a length of at least 20%, at least 30%, at least 50%, at least 75%, at least 90% of the nucleotides of the respective HCP5 nucleic acid.

The term "splice variant" as used herein encompasses variants of a nucleic acid sequence in which selected introns and/or exons or parts thereof have been excised, replaced, displaced or added, or in which introns have been shortened or lengthened. Thus, a splice variant can have one or more or even all introns removed or added or partially removed or partially added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the HCP5 nucleotide sequence as defined by SEQ ID NO: 1 or the HCP5 protein sequence as defined by SEQ ID NO: 3.

The term "increased activity" or "enhanced activity" as used herein means any protein having increased activity and which provides an increased fungal resistance compared with the wildtype plant merely expressing the respective endogenous HCP5 nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

HCP5 Nucleic Acids

The HCP5 nucleic acid to be overexpressed in order to achieve increased resistance to fungal pathogens, e.g., of the family Phakopsoraceae, for example soybean rust, is preferably a nucleic acid coding for an HCP5 protein, and is preferably as defined by SEQ ID NO: 10, 1, 2, 4, 13-19, 20, 22, 24, 26, 28, 30, 32, or 34, or a fragment, homolog, derivative, orthologue or paralogue thereof, or a splice variant thereof. Preferably, the nucleic acid coding for an HCP5 protein of the present invention has at least 60% identity, preferably at least 70% sequence identity, at least 80%, at least 90%, at least 95%, at least 98%, at least 99% sequence identity, or even 100% sequence identity with SEQ ID NO: 10, 1, 2, 4, 13-19, 20, 22, 24, 26, 28, 30, 32, or 34, or is a functional fragment thereof, or a splice variant thereof. Most preferred is at least 95% identity, more preferred is at least 90% identity, at least 98% or at least 99% identity with SEQ ID NO: 10, 1, 2, 4, 13-19, 20, 22, 24, 26, 28, 30, 32, or 34.

Preferably, the HCP5 nucleic acid to be overexpressed in order to achieve increased resistance to fungal pathogens, e.g., of the family Phakopsoraceae, for example soybean rust, is preferably a nucleic acid coding for an HCP5 protein, and is preferably as defined by SEQ ID NO: 4, or a fragment, homolog, derivative, orthologue or paralogue thereof, or a splice variant thereof. Preferably, the nucleic acid coding for an HCP5 protein of the present invention has at least 60% identity, preferably at least 70% sequence identity, at least 80%, at least 90%, at least 95%, at least 98%, at least 99% sequence identity, or even 100% sequence identity with SEQ ID NO: 4 or is a functional fragment thereof, or a splice variant thereof. Most preferred is at least 90% identity, at least 95% identity, more preferred is at least 98% or at least 99% identity with SEQ ID NO: 4.

More preferably, the HCP5 nucleic acid to be overexpressed in order to achieve increased resistance to fungal pathogens, e.g., of the family Phakopsoraceae, for example soybean rust, is preferably a nucleic acid coding for an HCP5 protein, and is preferably as defined by SEQ ID NO: 1, or a fragment, homolog, derivative, orthologue or paralogue thereof, or a splice variant thereof. Preferably, the nucleic acid coding for an HCP5 protein of the present invention has at least 60% identity, preferably at least 70% sequence identity, at least 80%, at least 90%, at least 95%, at least 98%, at least 99% sequence identity, or even 100% sequence identity with SEQ ID NO: 1 or is a functional fragment thereof, or a splice variant thereof. Most preferred is at least 95% identity, more preferred is at least 98% or at least 99% identity with SEQ ID NO: 1.

More preferably, the HCP5 nucleic acid to be overexpressed in order to achieve increased resistance to fungal pathogens, e.g., of the family Phakopsoraceae, for example soybean rust, is preferably a nucleic acid coding for an HCP5 protein, and is preferably as defined by SEQ ID NO: 10, or a fragment, homolog, derivative, orthologue or paralogue thereof, or a splice variant thereof. Preferably, the nucleic acid coding for an HCP5 protein of the present invention has at least 60% identity, preferably at least 70% sequence identity, at least 80%, at least 90%, at least 95%, at least 98%, at least 99% sequence identity, or even 100% sequence identity with SEQ ID NO: 10 or is a functional fragment thereof, or a splice variant thereof. Most preferred is at least 95% identity, more preferred is at least 98% or at least 99% identity with SEQ ID NO: 10.

More preferably, the HCP5 nucleic acid to be overexpressed in order to achieve increased resistance to fungal pathogens, e.g., of the family Phakopsoraceae, for example soybean rust, is preferably a nucleic acid coding for an HCP5 protein, and is preferably as defined by SEQ ID NO: 5, or a fragment, homolog, derivative, orthologue or paralogue thereof, or a splice variant thereof. Preferably, the nucleic acid coding for an HCP5 protein of the present invention has at least 60% identity, preferably at least 70% sequence identity, at least 80%, at least 90%, at least 95%, at least 98%, at least 99% sequence identity, or even 100% sequence identity with SEQ ID NO: 5 or is a functional fragment thereof, or a splice variant thereof. Most preferred is at least 95% identity, more preferred is at least 98% or at least 99% identity with SEQ ID NO: 5.

SEQ ID NO: 10 corresponds to SEQ ID NO: 1, wherein in SEQ ID NO: 10 certain recognition sites for restriction endonucleases have been removed.

Preferably the HCP5 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11, 10, 1, 2, 4, 5, 13-19, 20, 22, 24, 26, 28, 30, 32, or 34, or a functional fragment, derivative, orthologue, or paralogue thereof, or a splice variant thereof;

(ii) a nucleic acid encoding a HCP5 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 12, 3, 21, 23, 25, 27, 29, 31, 33, or 35, or a functional fragment, derivative, orthologue, or paralogue thereof; preferably the HCP5 protein has essentially the same biological activity as an HCP5 protein encoded by SEQ ID NO: 11, 10, 1, 2, 4, 5, 13-19, 20, 22, 24, 26, 28, 30, 32, or 34; preferably the HCP5 protein confers enhanced fungal resistance relative to control plants;

(iii) a nucleic acid molecule which hybridizes with a complementary sequence of anyone of the nucleic acids of (i) or (ii) under high stringency hybridization conditions; preferably encoding a HCP5 protein; preferably wherein the nucleic acid molecule codes for a polypeptide which has essentially identical properties to the polypeptide described in SEQ ID NO: 12, 3, 21, 23, 25, 27, 29, 31, 33, or 35; preferably the encoded protein confers enhanced fungal resistance relative to control plants; and (iv) a nucleic acid encoding the same HCP5 protein as the HCP5 nucleic acids of (i) to (iii) above, but differing from the HCP5 nucleic acids of (i) to (iii) above due to the degeneracy of the genetic code.

Preferably, the nucleic acid coding for an HCP5 protein of the present invention has at least 60% identity, preferably at least 70% sequence identity, at least 80%, at least 90%, at least 95%, at least 98%, at least 99% sequence identity, or even 100% sequence identity with SEQ ID NO: 1. Most preferred is at least 95% identity, more preferred is at least 98% or at least 99% identity with SEQ ID NO: 1.

Preferably, the nucleic acid coding for an HCP5 protein of the present invention has at least 60% identity, preferably at least 70% sequence identity, at least 80%, at least 90%, at least 95%, at least 98%, at least 99% sequence identity, or even 100% sequence identity with SEQ ID NO: 2. Most preferred is at least 95% identity, more preferred is at least 98% or at least 99% identity with SEQ ID NO: 2.

Preferably, the nucleic acid coding for an HCP5 protein of the present invention has at least 60% identity, preferably at least 70% sequence identity, at least 80%, at least 90%, at least 95%, at least 98%, at least 99% sequence identity, or even 100% sequence identity with SEQ ID NO: 10. Most preferred is at least 95% identity, more preferred is at least 98% or at least 99% identity with SEQ ID NO: 10.

Preferably the HCP5 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof;

(ii) a nucleic acid encoding a HCP5 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof; preferably the HCP5 protein has essentially the same biological activity as an HCP5 protein encoded by SEQ ID NO: 1, preferably the HCP5 protein confers enhanced fungal resistance relative to control plants;

(iii) a nucleic acid molecule which hybridizes with a complementary sequence of anyone of the nucleic acids of (i) or (ii) under high stringency hybridization conditions; preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and (iv) a nucleic acid encoding the same HCP5 protein as the HCP5 nucleic acids of (i) to (iii) above, but differing from the HCP5 nucleic acids of (i) to (iii) above due to the degeneracy of the genetic code.

Preferably the HCP5 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 10, or a functional fragment, derivative, orthologue, or paralogue thereof, or a splice variant thereof;

(ii) a nucleic acid encoding a HCP5 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof; preferably the HCP5 protein has essentially the same biological activity as an HCP5 protein encoded by SEQ ID NO: 10, preferably the HCP5 protein confers enhanced fungal resistance relative to control plants;

(iii) a nucleic acid molecule which hybridizes with a complementary sequence of anyone of the nucleic acids of (i) or (ii) under high stringency hybridization conditions; preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and (iv) a nucleic acid encoding the same HCP5 protein as the HCP5 nucleic acids of (i) to (iii) above, but differing from the HCP5 nucleic acids of (i) to (iii) above due to the degeneracy of the genetic code.

Percentages of identity of a nucleic acid are indicated with reference to the entire nucleotide region given in a sequence specifically disclosed herein.

Preferably the portion of the HCP5 nucleic acid is about 1000-1200, about 1200-1400, about 1400-1600, about 1600-1800, about 1800-2000, about 2000-2200, about 2200-2400, about 2400-2600, about 2600-2800, about 2800-3000, or about 3000-3123 nucleotides, preferably consecutive nucleotides, preferably counted from the 5' or 3' end of the nucleic acid, in length, of the nucleic acid sequences given in SEQ ID NO: 10, 1, 2, 4, 5, 13-19, 20, 22, 24, 26, 28, 30, 32, or 34.

Preferably, the HCP5 nucleic acid comprises at least about 1400, at least about 1600, at least about 1800, at least about 2000, at least about 2200, at least about 2400, at least about 2600, at least about 2800, at least about 3000, or at least about 3100 nucleotides, preferably continuous nucleotides, preferably counted from the 5' or 3' end of the nucleic acid or up to the full length of the nucleic acid sequence set out in SEQ ID NO: 10, 1, 2, 4, 5, 13-19, 20, 22, 24, 26, 28, 30, 32, or 34.

Preferably, the HCP5 nucleic acid comprises at least about 1600, at least about 1800, at least about 2000, at least about 2100, at least about 2200, at least about 2300, or at least about 2400 nucleotides, preferably continuous nucleotides, preferably counted from the 5' or 3' end of the nucleic acid or up to the full length of the nucleic acid sequence set out in SEQ ID NO: 1.

Preferably the portion of the HCP5 nucleic acid is about 1000-1100, about 1100-1200, about 1200-1300, about 1300-1400, about 1400-1500, about 1500-1600, about 1600-1700, about 1700-1800, about 1800-1900, about 1900-2000, about 2000-2100, about 2100-2200, about 2200-2300, or about 2300-2403 nucleotides, preferably consecutive nucleotides, preferably counted from the 5' or 3' end of the nucleic acid, in length, of the nucleic acid sequences given in SEQ ID NO: 1.

Preferably, the HCP5 nucleic acid comprises at least about 1600, at least about 1800, at least about 2000, at least about 2100, at least about 2200, at least about 2300, or at least about 2400 nucleotides, preferably continuous nucleotides, preferably counted from the 5' or 3' end of the nucleic acid or up to the full length of the nucleic acid sequence set out in SEQ ID NO: 10 or 13-19.

Preferably the portion of the HCP5 nucleic acid is about 1000-1100, about 1100-1200, about 1200-1300, about 1300-1400, about 1400-1500, about 1500-1600, about 1600-1700, about 1700-1800, about 1800-1900, about 1900-2000, about 2000-2100, about 2100-2200, about 2200-2300, or about 2300-2403 nucleotides, preferably consecutive nucleotides, preferably counted from the 5' or 3' end of the nucleic acid, in length, of the nucleic acid sequences given in SEQ ID NO: 10 or 13-19.

Preferably, the HCP5 nucleic acid comprises at least about 500, at least about 600, at least about 700, at least about 750, or at least about 800 nucleotides, preferably continuous nucleotides, preferably counted from the 5' or 3' end of the nucleic acid or up to the full length of the nucleic acid sequence set out in SEQ ID NO: 11.

Preferably the portion of the HCP5 nucleic acid is about 500-600, about 600-700, about 700-725, about 725-750, about 750-775, about 775-800, or about 800-829 nucleotides, preferably consecutive nucleotides, preferably counted from the 5' or 3' end of the nucleic acid, in length, of the nucleic acid sequences given in SEQ ID NO: 11.

Figure 7:
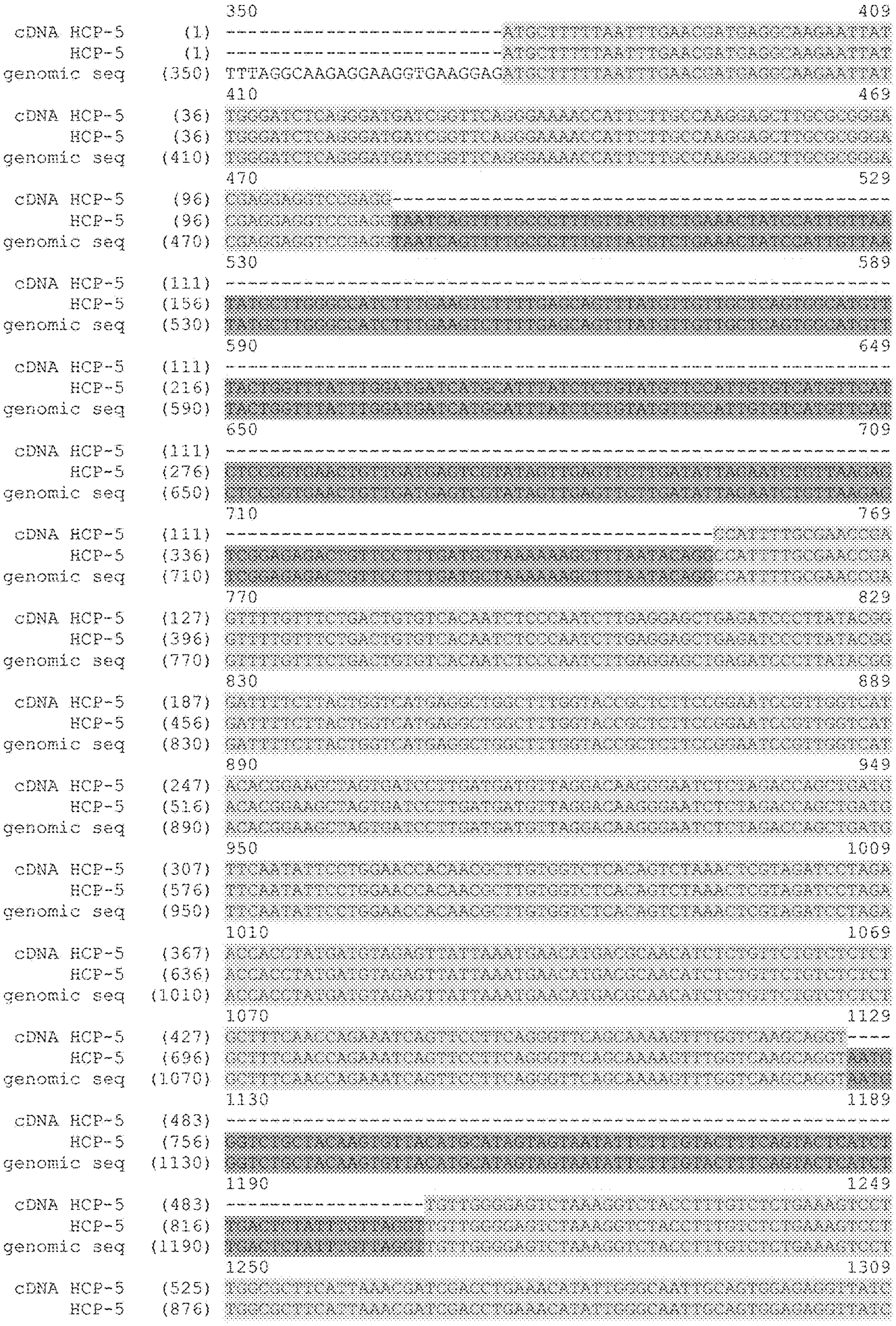
FIG. 7 shows the alignment of the *Arabidopsis* genome sequence (part of accession No NC_003076.8, SEQ ID NO: 4), a HCP5 cDNA (derived by bioinformatics from the genomic sequence; accession No NM_124099, SEQ ID NO: 2), and the sequence of the HCP5 nucleic acid as shown in SEQ ID NO: 1.

Preferably, the HCP5 nucleic acid is a HCP5 nucleic acid splice variant. Preferred splice variants are splice variants of a nucleic acid represented by SEQ ID NO: 4. Preferred HCP5 nucleic acids being a splice variant of SEQ ID NO: 4 are shown in FIG. 7.

Preferably, the HCP5 nucleic acid is an isolated nucleic acid molecule comprising a splice variant of SEQ ID NO: 4, wherein the splice variant is selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 10, 1, or 2, or a functional fragment, derivative, orthologue, or paralogue thereof;

(ii) a nucleic acid encoding a HCP5 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof; preferably the HCP5 protein has essentially the same biological activity as an HCP5 protein encoded by SEQ ID NO: 10, 1, or 2; preferably the HCP5 protein confers enhanced fungal resistance relative to control plants;

(iii) a nucleic acid molecule which hybridizes with a complementary sequence of anyone of the nucleic acids of (i) or (ii) under high stringency hybridization conditions; preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and (iv) a nucleic acid encoding the same HCP5 protein as the HCP5 nucleic acids of (i) to (iii) above, but differing from the HCP5 nucleic acids of (i) to (iii) above due to the degeneracy of the genetic code.

Preferred splice variants of SEQ ID NO: 4 consist of or comprise anyone of the nucleotide sequences shown in SEQ ID NO: 10, 1, or 2. Most preferred is the HCP5 nucleic acid splice variant as shown in SEQ ID NO: 2.

Preferably the HCP5 nucleic acid is an isolated nucleic acid molecule comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, or a splice variant thereof;

(ii) a nucleic acid molecule which hybridizes with a complementary sequence of anyone of the nucleic acids of (i) under high stringency hybridization conditions; preferably encoding a HCP5 protein; preferably wherein the nucleic acid molecule codes for a polypeptide which has essentially identical properties to the polypeptide described in SEQ ID No: 12 or 3; preferably the encoded protein confers enhanced fungal resistance relative to control plants; and (iii) a nucleic acid encoding the same HCP5 protein as the HCP5 nucleic acids of (i) or (ii) above, but differing from the HCP5 nucleic acids of (i) or (ii) above due to the degeneracy of the genetic code;

wherein the splice variant thereof is selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 10, 1, or 2, or a functional fragment, derivative, orthologue, or paralogue thereof;

(ii) a nucleic acid encoding a HCP5 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof; preferably the HCP5 protein has essentially the same biological activity as an HCP5 protein encoded by SEQ ID NO: 10, 1, or 2; preferably the HCP5 protein confers enhanced fungal resistance relative to control plants;

(iii) a nucleic acid molecule which hybridizes with a complementary sequence of anyone of the nucleic acids of (i) or (ii) under high stringency hybridization conditions; preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and (iv) a nucleic acid encoding the same HCP5 protein as the HCP5 nucleic acids of (i) to (iii) above, but differing from the HCP5 nucleic acids of (i) to (iii) above due to the degeneracy of the genetic code.

More preferably the HCP5 nucleic acid is an isolated nucleic acid molecule comprising a nucleic acid selected from the group consisting of:

a nucleic acid having in increasing order of preference least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 4, or a splice variant thereof;

wherein the splice variant thereof is selected from the group consisting of:

a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 10, 1, or 2; preferably SEQ ID NO: 10.

In a preferred embodiment, the HCP5 nucleic acid comprises a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11, or a functional fragment, derivative, orthologue, or paralogue thereof.

In a preferred embodiment, the HCP5 nucleic acid comprises a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 10, 1, 2, or 4, or a functional fragment, derivative, orthologue, or paralogue thereof, wherein the HCP5 nucleic acid comprises a nucleic acid sequence having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11.

In a preferred embodiment, the HCP5 nucleic acid is a splice variant comprising a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11, or a functional fragment, derivative, orthologue, or paralogue thereof.

Preferably, the HCP5 nucleic acid comprises an exon sequence comprising a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11, or a functional fragment, derivative, orthologue, or paralogue thereof.

In a preferred embodiment, the HCP5 nucleic acid comprises a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 10, 1, 2, or 4, or a splice variant thereof, wherein the splice variant comprises a nucleic acid sequence, preferably an exon sequence, having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11.

In a preferred embodiment, the HCP5 nucleic acid encodes a HCP5 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 11, or a functional fragment, derivative, orthologue, or paralogue thereof; preferably the HCP5 protein has essentially the same biological activity as an HCP5 protein encoded by SEQ ID NO: 10, 1, 2, or 4; preferably the HCP5 protein confers enhanced fungal resistance relative to control plants.

In a preferred embodiment, the HCP5 nucleic acid encodes a HCP5 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 3, or a functional fragment, derivative, orthologue, or paralogue thereof, wherein the HCP5 nucleic acid comprises an nucleic acid sequence, preferably an exon sequence, encoding an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 12, or a functional fragment, derivative, orthologue, or paralogue thereof; preferably the HCP5 protein has essentially the same biological activity as an HCP5 protein encoded by SEQ ID NO: 10, 1, 2, or 4; preferably the HCP5 protein confers enhanced fungal resistance relative to control plants.

The HCP5 nucleic acids described herein are useful in the constructs, methods, plants, harvestable parts and products of the invention.

HCP5 Proteins

The HCP5 protein is preferably defined by SEQ ID NO: 3, 21, 23, 25, 27, 29, 31, 33, or 35, or a fragment, homolog, derivative, orthologue or paralogue thereof. Preferably, the HCP5 protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 3, 21, 23, 25, 27, 29, 31, 33, or 35 or a functional fragment thereof.

More preferably, the HCP5 protein of the present invention has at least 60%, preferably at least 70% sequence identity, at least 80%, at least 90%, at least 95%, at least 98%, at least 99% sequence identity, or even 100% sequence identity with SEQ ID NO: 3, 21, 23, 25, 27, 29, 31, 33, or 35, or is a functional fragment thereof, an orthologue or a paralogue thereof. Most preferred is at least 90% identity, at least 95% identity, more preferred is at least 98% or at least 99% identity with SEQ ID NO: 3, 21, 23, 25, 27, 29, 31, 33, or 35.

In another embodiment, the HCP5 protein of the present invention comprises an amino acid sequence that has at least 60%, preferably at least 70% sequence identity, at least 80%, at least 90%, at least 95%, at least 98%, at least 99% sequence identity, or even 100% sequence identity with SEQ ID NO: 12.

More preferably, the HCP5 protein of the present invention has at least 60%, preferably at least 70% sequence identity, at least 80%, at least 90%, at least 95%, at least 98%, at least 99% sequence identity, or even 100% sequence identity with SEQ ID NO: 3, wherein the HCP5 protein comprises an amino acid sequence having at least 80%, at least 90%, at least 95%, at least 98%, at least 99% sequence identity, or even 100% sequence identity with SEQ ID NO: 12; or is a functional fragment thereof, an orthologue or a paralogue thereof.

Preferably, the HCP5 protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 12, 3, 21, 23, 25, 27, 29, 31, 33, or 35, or a functional fragment, derivative, orthologue, or paralogue thereof; preferably the HCP5 protein has essentially the same biological activity as an HCP5 protein encoded by SEQ ID NO: 10, 1, 2, 4, 5, 13-19, 20, 22, 24, 26, 28, 30, 32, or 34; preferably the HCP5 protein confers enhanced fungal resistance relative to control plants; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11, 10, 1, 2, 4, 5, 13-19, 20, 22, 24, 26, 28, 30, 32, or 34, or a functional fragment, derivative, orthologue, or paralogue thereof, or a splice variant thereof; preferably the HCP5 protein confers enhanced fungal resistance relative to control plants.

Preferably, the HCP5 protein is a protein comprising an amino acid sequence selected from the group consisting of:

(i) an amino acid sequence having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 12, 3, 21, 23, 25, 27, 29, 31, 33, or 35, or a functional fragment, derivative, orthologue, or paralogue thereof; preferably the HCP5 protein has essentially the same biological activity as an HCP5 protein encoded by SEQ ID NO: 10, 1, 2, 4, 5, 13-19, 20, 22, 24, 26, 28, 30, 32, or 34; preferably the HCP5 protein confers enhanced fungal resistance relative to control plants; or (ii) an amino acid sequence encoded by a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11, 10, 1, 2, 4, 5, 13-19, 20, 22, 24, 26, 28, 30, 32, or 34, or a functional fragment, derivative, orthologue, or paralogue thereof, or a splice variant thereof; preferably the HCP5 protein confers enhanced fungal resistance relative to control plants.

A preferred derivative of a HCP5 protein is a HCP5 protein consisting of or comprising an amino acid sequence selected from the group consisting of:

an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence represented by SEQ ID NO: 12 or 3, wherein the non-identical amino acid residues are conservative amino acid substitutions, preferably as shown in Table 1, of the corresponding amino acid residue of SEQ ID NO: 12 or 3; preferably the HCP5 protein has essentially the same biological activity as SEQ ID NO: 3 or as a HCP5 protein encoded by SEQ ID NO: 10, 1, 2 or 4; preferably the HCP5 protein confers enhanced fungal resistance relative to control plants.

Preferably, the HCP5 protein consists of or comprises an amino acid sequence represented by SEQ ID NO: 3 with one or more conservative amino acid substitutions, preferably as shown in Table 1, of the corresponding amino acid residues of SEQ ID NO: 3. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 1-10, 10-20, 20-30, 40-50, 50-60, 60-70, 70-80, 80-90, 90-100, 100-110, 110-120, or 120-130 amino acid residues of SEQ ID NO: 12 or 3 are conservative amino acid substitutions, preferably as shown in Table 1, of the corresponding amino acid residue of SEQ ID NO: 12, 3, 21, 23, 25, 27, 29, 31, 33, or 35.

More preferably, the HCP5 protein consists of or comprises an amino acid sequence having at least 80%, at least 85%, at least 90%, at least 95%, at least 98% or at least 99% sequence identity with an amino acid sequence as represented by SEQ ID NO: 12 or 3, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 of the non-identical amino acid residues, or wherein 1-10, 10-20, 20-30, 40-50, 50-60, 60-70, 70-80, 80-90 or 90-100 or even all of the non-identical amino acid residues are conservative amino acid substitutions, preferably as shown in Table 1, of the corresponding amino acid residue of SEQ ID NO: 12, 3, 21, 23, 25, 27, 29, 31, 33, or 35.

Percentages of identity of a polypeptide or protein are indicated with reference to the entire amino acid sequence specifically disclosed herein.

Preferably, the HCP5 protein comprises at least about 300, at least about 400, at least about 450, at least about 500, at least about 520, at least about 540, at least about 560, at least about 580, at least about 590, at least about 600, at least about 610, or at least about 620 amino acid residues, preferably continuous amino acid residues, preferably counted from the N-terminus or the C-terminus of the amino acid sequence, or up to the full length of the amino acid sequence set out in SEQ ID NO: 3, 21, 23, 25, 27, 29, 31, 33, or 35.

Preferably, the HCP5 polypeptide comprises about 300-400, about 400-500, about 500-520, about 520-540, about 540-560, about 560-580, about 580-590, about 590-600, about 600-610, about 610-623 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 3, 21, 23, 25, 27, 29, 31, 33, or 35.

Preferably, the HCP5 protein comprises at least about 100, at least about 125, at least about 150, at least about 175, at least about 200, at least about 225, at least about 250, or at least about 275 amino acid residues, preferably continuous amino acid residues, preferably counted from the N-terminus or the C-terminus of the amino acid sequence, or up to the full length of the amino acid sequence set out in SEQ ID NO: 12.

Preferably, the HCP5 polypeptide comprises about 100-125, about 125-150, about 150-175, about 175-200, about 200-225, about 225-250, or about 250-275 amino acids, preferably consecutive amino acids, preferably counted from the N-terminus or C-terminus of the amino acid sequence, or up to the full length of any of the amino acid sequences encoded by the nucleic acid sequences set out in SEQ ID NO: 12.

The HCP5 proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phakopsoraceae, for example soy bean rust, in a plant, plant part, or plant cell by increasing the expression of an HCP5 protein or a functional fragment, orthologue, paralogue or homologue thereof in comparison to wild-type plants, wild-type plant parts or wild-type plant cells.

The present invention also provides a method for increasing resistance to fungal pathogens, in particular a heminecrotrophic pathogen, in particular to rust pathogens (i.e., fungal pathogens of the order Pucciniales), preferably fungal pathogens of the family Phakopsoraceae, preferably against fungal pathogens of the genus *Phakopsora*, most preferably against *Phakopsora pachyrhizi* and *Phakopsora meibomiae*, also known as soy bean rust in plants or plant cells, wherein in comparison to wild type plants, wild type plant parts, or wild type plant cells an HCP5 protein is overexpressed.

The present invention further provides a method for increasing resistance to fungal pathogens of the genus *Phakopsora*, most preferably against *Phakopsora pachyrhizi* and *Phakopsora meibomiae*, also known as soy bean rust in plants or plant cells by overexpression of an HCP5 protein.

In preferred embodiments, the protein amount and/or function of the HCP5 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the HCP5 nucleic acid.

In one embodiment of the invention, the HCP5 protein is encoded by a nucleic acid comprising (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 11, 10, 1, 2, 4, 5, 13-19, 20, 22, 24, 26, 28, 30, 32, or 34, a functional fragment thereof, or an orthologue or a paralogue thereof, or a splice variant thereof; or by (ii) an exogenous nucleic acid encoding a protein comprising an amino acid sequence having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 12, 3, 21, 23, 25, 27, 29, 31, 33, or 35, a functional fragment thereof, an orthologue or a paralogue thereof, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12, 3, 21, 23, 25, 27, 29, 31, 33, or 35; preferably the encoded protein confers enhanced fungal resistance relative to control plants; or by (iv) an exogenous nucleic acid encoding the same HCP5 protein as any of the nucleic acids of (i) to (iii) above, but differing from the nucleic acids of (i) to (iii) above due to the degeneracy of the genetic code.

In another embodiment of the invention, the HCP5 protein comprises an amino acid sequence (i) having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 12; or (ii) encoded by a nucleic acid sequence having least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 11; preferably the HCP5 protein has essentially the same biological activity as SEQ ID NO: 3 or as a HCP5 protein encoded by SEQ ID NO: 10, 1, 2 or 4; preferably the encoded protein confers enhanced fungal resistance relative to control plants.

A method for increasing fungal resistance, preferably resistance to Phakopsoraceae, for example soy bean rust, in a plant, plant part, or plant cell, by increasing the expression of an HCP5 protein or a functional fragment, orthologue, paralogue or homologue thereof, or a splice variant thereof, wherein the HCP5 protein is encoded by a nucleic acid comprising (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 11, 10, 1, 2, 4, 5, 13-19, 20, 22, 24, 26, 28, 30, 32, or 34, or a functional fragment thereof, an orthologue or a paralogue thereof, or a splice variant thereof;

(ii) an exogenous nucleic acid encoding a protein comprising an amino acid sequence having at least 60%, preferably at least 70% sequence identity, at least 80%, at least 90%, at least 95%, at least 98%, at least 99% sequence identity, or even 100% sequence identity with SEQ ID NO: 12, 3, 21, 23, 25, 27, 29, 31, 33, or 35, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by (iv) an exogenous nucleic acid encoding the same HCP5 protein as any of the nucleic acids of (i) to (iii) above, but differing from the nucleic acids of (i) to (iii) above due to the degeneracy of the genetic code is a further embodiment of the invention.

A method for increasing fungal resistance, preferably resistance to Phakopsoraceae, for example soy bean rust, in a plant, plant part, or plant cell, by increasing the expression of an HCP5 protein or a functional fragment, orthologue, paralogue or homologue thereof, or a splice variant thereof, wherein the HCP5 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by (iv) an exogenous nucleic acid encoding the same HCP5 protein as any of the nucleic acids of (i) to (iii) above, but differing from the nucleic acids of (i) to (iii) above due to the degeneracy of the genetic code is a further embodiment of the invention.

A method for increasing fungal resistance, preferably resistance to Phakopsoraceae, for example soy bean rust, in a plant, plant part, or plant cell, by increasing the expression of an HCP5 protein or a functional fragment, orthologue, paralogue or homologue thereof, or a splice variant thereof, wherein the HCP5 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 10 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by (iv) an exogenous nucleic acid encoding the same HCP5 protein as any of the nucleic acids of (i) to (iii) above, but differing from the nucleic acids of (i) to (iii) above due to the degeneracy of the genetic code is a further embodiment of the invention.

In a further method of the invention, the method comprises the steps of (a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 10, 1, 2, 4, 5, 13-19, 20, 22, 24, 26, 28, 30, 32, or 34, or a functional fragment thereof, or an orthologue or a paralogue thereof, or a splice variant thereof;
   (ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 12, 3, 21, 23, 25, 27, 29, 31, 33, or 35, a functional fragment thereof, an orthologue or a paralogue thereof; preferably the encoded protein confers enhanced fungal resistance relative to control plants;
   (iii) a nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or
   (iv) a nucleic acid encoding the same HCP5 polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for an HCP5 protein is expressed in an amount and for a period sufficient to generate or to increase soybean rust resistance in said plant.

Preferably, the method comprises the steps of (a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, or a functional fragment thereof, or an orthologue or a paralogue thereof, or a splice variant thereof;
   (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;
   (iii) a nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or
   (iv) a nucleic acid encoding the same HCP5 polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for an HCP5 protein is expressed in an amount and for a period sufficient to generate or to increase soybean rust resistance in said plant.

Preferably, the method comprises the steps of (a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 10, or a functional fragment thereof, or an orthologue or a paralogue thereof, or a splice variant thereof;
   (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) a nucleic acid encoding the same HCP5 polypeptide as any of the nucleic acids of (i) to (iii) above, but differing from the nucleic acids of (i) to (iii) above due to the degeneracy of the genetic code, in functional linkage with a promoter;

(b) regenerating the plant from the plant cell; and (c) expressing said nucleic acid, optionally wherein the nucleic acid which codes for an HCP5 protein is expressed in an amount and for a period sufficient to generate or to increase soybean rust resistance in said plant.

Preferably, the method for increasing fungal resistance, preferably resistance to Phakopsoraceae, for example soy bean rust, in a plant, plant part, or plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 10, 1, 2, or 4, or a functional fragment thereof, or an orthologue or a paralogue thereof, or a splice variant thereof;

(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) an exogenous nucleic acid encoding the same HCP5 polypeptide as any of the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of an HCP5 protein, wherein the HCP5 protein is encoded by a nucleic acid comprising (i) an exogenous nucleic acid having at least 80%, at least 90%, at least 95%, at least 98%, at least 99% sequence identity, or even 100% sequence identity with SEQ ID NO: 11, 10, 1, 2, 4, 5, 13-19, 20, 22, 24, 26, 28, 30, 32, or 34;

(ii) an exogenous nucleic acid encoding a protein comprising an amino acid sequence having at least 80%, at least 90%, at least 95%, at least 98%, at least 99% sequence identity, or even 100% sequence identity with SEQ ID NO: 12 or 3; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12, 3, 21, 23, 25, 27, 29, 31, 33, or 35; preferably the encoded protein confers enhanced fungal resistance relative to control plants; and/or by (iv) an exogenous nucleic acid encoding the same HCP5 protein as any of the nucleic acids of (i) to (iii) above, but differing from the nucleic acids of (i) to (iii) above due to the degeneracy of the genetic code, wherein increasing the expression of the HCP5 protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of an HCP5 protein, wherein the HCP5 protein is encoded by a nucleic acid comprising (i) an exogenous nucleic acid having at least 80%, at least 90%, at least 95%, at least 98%, at least 99% sequence identity, or even 100% sequence identity with SEQ ID NO: 11, 10, 1, 2, 4, 5, 13-19, 20, 22, 24, 26, 28, 30, 32, or 34;

(ii) an exogenous nucleic acid encoding a protein comprising an amino acid sequence having at least 80%, at least 90%, at least 95%, at least 98%, at least 99% sequence identity, or even 100% sequence identity with SEQ ID NO: 12, 3, 21, 23, 25, 27, 29, 31, 33, or 35; preferably the encoded protein confers enhanced fungal resistance relative to control plants; or (iii) an exogenous nucleic acid encoding the same HCP5 protein as any of the nucleic acids of (i) to (ii) above, but differing from the nucleic acids of (i) to (ii) above due to the degeneracy of the genetic code, wherein increasing the expression of the HCP5 protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis/Blumeria graminis* |

TABLE 2-continued

| Diseases caused by biotrophic phytopathogenic fungi | |
|---|---|
| Disease | Pathogen |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi*, *P. meibomiae* |
| Rust (tropical corn) | *Physopella pallescens*, *P. zeae* = *Angiopsora zeae* |

TABLE 3

| Diseases caused by necrotrophic and/or hemibiotrophic fungi and Oomycetes | |
|---|---|
| Disease | Pathogen |
| Plume blotch | *Septoria* (*Stagonospora*) *nodorum* |
| Leaf blotch | *Septoria tritici* |
| Ear fusarioses | *Fusarium* spp. |
| Late blight | *Phytophthora infestans* |
| Anthrocnose leaf blight<br>Anthracnose stalk rot | *Colletotrichum graminicola* (teleomorph: *Glomerella graminicola* Politis); *Glomerella tucumanensis* (anamorph: *Glomerella falcatum* Went) |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |
| *Didymella* leaf spot | *Didymella exitalis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (*graminicola* downy mildew) | *Sclerospora graminicola* |
| Leaf spots, minor | *Alternaria alternata*, *Ascochyta maydis*, *A. tritici*, *A. zeicola*, *Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis*, *Leptothyrium zeae*, *Ophiosphaerella herpotricha*, (anamorph: *Scolecosporiella* sp.), *Paraphaeosphaeria michotii*, *Phoma* sp., *Septoria zeae*, *S. zeicola*, *S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot<br>*Helminthosporium* ear rot (race 1) | *Cochliobolus carbonum* (anamorph: *Bipolaris zeicola* = *Helminthosporium carbonum*) |
| *Phaeosphaeria* leaf spot | *Phaeosphaeria maydis* = *Sphaerulina maydis* |
| Rostratum leaf spot (*Helminthosporium* leaf disease, ear and stalk rot) | *Setosphaeria rostrata*, (anamorph: *xserohilum rostratum* = *Helminthosporium rostratum*) |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| *Spontaneum* downy mildew | *Peronosclerospora spontanea* = *Sclerospora spontanea* |
| Sugarcane downy mildew | *Peronosclerospora sacchari* = *Sclerospora sacchari* |
| Sclerotium ear rot (southern blight) | *Sclerotium rolfsii* Sacc. (teleomorph: *Athelia rolfsii*) |
| Seed rot-seedling blight | *Bipolaris sorokiniana*, *B. zeicola* = *Helminthosporium carbonum*, *Diplodia maydis*, *Exserohilum pedicillatum*, *Exserohilum turcicum* = *Helminthosporium turcicum*, *Fusarium avenaceum*, *F. culmorum*, *F. moniliforme*, *Gibberella zeae* (anamorph: *F. graminearum*), *Macrophomina phaseolina*, *Penicillium* spp., *Phomopsis* sp., *Pythium* spp., *Rhizoctonia solani*, *R. zeae*, *Sclerotium rolfsii*, *Spicaria* sp. |
| *Selenophoma* leaf spot | *Selenophoma* sp. |
| Yellow leaf blight | *Ascochyta ischaemi*, *Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea, Polymyxa graminis,*

Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (*rhizoctonia* root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (*verticillium* wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales, preferably the group Uredinales (rusts), among which in particular the Melompsoraceae. Preferred are Phakopsoraceae, more preferably *Phakopsora*. Especially preferred are *Phakopsora pachyrhizi* and/or *Phakopsora meibomiae.*

Also preferred rust fungi are selected from the group of *Puccinia, Gymnosporangium, Juniperus, Cronartium, Hemileia*, and *Uromyces*; preferably *Puccinia sorghi, Gymnosporangium juniperi-virginianae, Juniperus virginiana, Cronartium ribicola, Hemileia vastatrix, Puccinia graminis, Puccinia coronata, Uromyces phaseoli, Puccinia hemerocallidis, Puccinia persistens* subsp. *Triticina, Puccinia striiformis, Puccinia graminis* causes, and/or *Uromyces appendeculatus.*

HCP5 Expression Constructs and Vector Constructs

A recombinant vector construct comprising:

(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 11, 10, 1, 2, 4, 5, 13-19, 20, 22, 24, 26, 28, 30, 32, or 34, or a functional fragment thereof, or an orthologue or a paralogue thereof, or a splice variant thereof;

(ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 12, 3, 21, 23, 25, 27, 29, 31, 33, or 35, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) a nucleic acid encoding the same HCP5 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 11, 10, 1, 2, 4, 5, 13-19, 20, 22, 24, 26, 28, 30, 32, or 34;

(ii) a nucleic acid coding for a protein comprising an amino acid sequence having at least 80%, at least 90%, at least 95%, at least 98%, at least 99% sequence identity, or even 100% sequence identity with SEQ ID NO: 12, 3, 21, 23, 25, 27, 29, 31, 33, or 35; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) a nucleic acid encoding the same HCP5 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 1;

(ii) a nucleic acid coding for a protein having at least 80%, at least 90%, at least 95%, at least 98%, at least 99% sequence identity, or even 100% sequence identity with SEQ ID NO: 3; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) a nucleic acid encoding the same HCP5 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO:
10;

(ii) a nucleic acid coding for a protein having at least 80%, at least 90%, at least 95%, at least 98%, at least 99% sequence identity, or even 100% sequence identity with SEQ ID NO: 3; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) a nucleic acid encoding the same HCP5 protein as any of the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

Especially preferred is a promoter from parsley, preferably, the parsley ubiquitine promoter. A preferred terminator is the terminator of the cathepsin D inhibitor gene from *Solanum tuberosum*.

In preferred embodiments, the increase in the protein amount and/or activity of the HCP5 protein takes place in a constitutive or tissue-specific manner. In especially preferred embodiments, an essentially pathogen-induced increase in the protein amount and/or protein activity takes place, for example by recombinant expression of the HCP5 nucleic acid under the control of a fungal-inducible promoter. In particular, the expression of the HCP5 nucleic acid takes place on fungal infected sites, where, however, preferably the expression of the HCP5 nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the Ipt2 or Ipt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:

WIR5 (=GstA1); acc. X56012; Dudler & Schweizer,

GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998), GLP2a, acc. AJ237942, Schweizer P., Christoffel A. and Dudler R., Plant J. 20, 541 (1999);

Prx7, acc. AJ003141, Kristensen B. K., Ammitzböll H., Rasmussen S. K. and Nielsen K. A., Molecular Plant Pathology, 2(6), 311 (2001);

GerA, acc. AF250933; Wu S., Druka A., Horvath H., Kleinhofs A., Kannangara G. and von Wettstein D., Plant Phys Biochem 38, 685 (2000);

OsROC1, acc. AP004656

RTBV, acc. AAV62708, AAV62707; Klöti A., Henrich C., Bieri S., He X., Chen G., Burkhardt P. K., Wünn J., Lucca P., Hohn T., Potrykus I. and Fütterer J., PMB 40, 249 (1999);

Chitinase ChtC2-Promoter from potato (Ancillo et al., Planta. 217(4), 566, (2003));

AtProT$_3$ Promoter (Grallath et al., Plant Physiology. 137(1), 117 (2005));

SHN-Promoters from *Arabidopsis* (AP2/EREBP transcription factors involved in cutin and wax production) (Aarón et al., Plant Cell. 16(9), 2463 (2004)); and/or GSTA1 from wheat (Dudler et al., WP2005306368 and Altpeter et al., Plant Molecular Biology. 57(2), 271 (2005)).

Mesophyll-specific promoters may be selected from the group consisting of:

PPCZm1 (=PEPC); Kausch A. P., Owen T. P., Zachwieja S. J., Flynn A. R. and Sheen J., Plant Mol. Biol. 45, 1 (2001);

OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);

OsPPDK, acc. AC099041;

TaGF-2.8, acc. M63223; Schweizer P., Christoffel A. and Dudler R., Plant J. 20, 541 (1999);

TaFBPase, acc. X53957;

TaWIS1, acc. AF467542; US 200220115849;

HvBIS1, acc. AF467539; US 200220115849;

ZmMIS1, acc. AF467514; US 200220115849;

HvPR1a, acc. X74939; Bryngelsson et al., Mol. Plant Microbe Interacti. 7 (2), 267 (1994);

HvPR1b, acc. X74940; Bryngelsson et al., Mol. Plant Microbe Interact. 7(2), 267 (1994);

HvB1,3gluc; acc. AF479647;

HvPrx8, acc. AJ276227; Kristensen et al., Molecular Plant Pathology, 2(6), 311 (2001); and/or HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of

PcUbi promoter from parsley (WO 03/102198)

CaMV 35S promoter: Cauliflower Mosaic Virus 35S promoter (Benfey et al. 1989 EMBO J. 8(8): 2195-2202), STPT promoter: *Arabidopsis thaliana* Short Triose phosphate translocator promoter (Accession NM_123979)

Act1 promoter: *Oryza sativa* actin 1 gene promoter (McElroy et al. 1990 PLANT CELL 2(2) 163-171 a) and/or EF1A2 promoter: *Glycine max* translation elongation factor EF1 alpha (US 20090133159).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

In preferred embodiments, the increase in the protein quantity or function of the HCP5 protein takes place in a constitutive or tissue-specific manner. In especially preferred embodiments, an essentially pathogen-induced increase in the protein quantity or protein function takes place, for example by exogenous expression of the HCP5 nucleic acid under the control of a fungal-inducible promoter. In particular, the expression of the HCP5 nucleic acid takes place on fungal infected sites, where, however, preferably the expression of the HCP5 nucleic acid sequence remains essentially unchanged in tissues not infected by fungus. In preferred embodiments, the protein amount of an HCP5 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the HCP5 nucleic acid.

A preferred embodiment is the use of an expression construct or a vector as described herein for the transformation of a plant, plant part, or plant cell to provide a pathogen resistant plant, plant part, or plant cell. Thus, a preferred embodiment is the use of an expression construct or a vector as described herein for increasing pathogen resistance in a plant, plant part, or plant cell compared to a control plant, plant part, or plant cell.

Transgenic Organisms; Transgenic Plants, Plant Parts, and Plant Cells

A preferred embodiment is a transgenic plant, transgenic plant part, or transgenic plant cell overexpressing an exogenous HCP5 protein. Preferably, the HCP5 protein overexpressed in the plant, plant part or plant cell is encoded by a nucleic acid comprising (i) an exogenous nucleic acid having at least 60% identity with SEQ ID NO: 11, 10, 1, 2, 4, 5, 13-19, 20, 22, 24, 26, 28, 30, 32, or 34 or a functional fragment, thereof, an orthologue or a paralogue thereof, or a splice variant thereof; or by (ii) an exogenous nucleic acid encoding a protein comprising an amino acid sequence having at least 60% identity with SEQ ID NO: 12, 3, 21, 23, 25, 27, 29, 31, 33, or 35, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by (iv) an exogenous nucleic acid encoding the same HCP5 protein as any of the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 10, 1, 2, 4, 5, 13-19, 20, 22, 24, 26, 28, 30, 32, or 34; or comprises an exogenous nucleic acid encoding a protein having at least 80%, at least 90%, at least 95%, at least 98%, at least 99% sequence identity, or even 100% sequence identity with SEQ ID NO: 3.

A preferred embodiment is a transgenic plant, transgenic plant part, or transgenic plant cell overexpressing an exogenous HCP5 protein. Preferably, the HCP5 protein overexpressed in the plant, plant part or plant cell is encoded by (i) an exogenous nucleic acid having at least 60% identity with SEQ ID NO: 1 or a functional fragment, thereof, an orthologue or a paralogue thereof, or a splice variant thereof; or by (ii) an exogenous nucleic acid encoding a protein having at least 60% identity with SEQ ID NO: 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by (iv) an exogenous nucleic acid encoding the same HCP5 protein as any of the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous HCP5 protein. Preferably, the HCP5 protein overexpressed in the plant, plant part or plant cell is encoded by (i) an exogenous nucleic acid having at least 60% identity with SEQ ID NO: 10 or a functional fragment, thereof, an orthologue or a paralogue thereof, or a splice variant thereof; or by (ii) an exogenous nucleic acid encoding a protein having at least 60% identity with SEQ ID NO: 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by (iv) an exogenous nucleic acid encoding the same HCP5 protein as any of the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 95%, at least 98%, at least 99% sequence identity, or even 100% sequence identity with SEQ ID NO: 3.

Most preferably, the exogenous nucleic acid has at least 80%, at least 90%, at least 95%, at least 98%, at least 99% sequence identity, or even 100% sequence identity with SEQ ID NO: 10; or comprises an exogenous nucleic acid encoding a protein having at least 95%, at least 98%, at least 99% sequence identity, or even 100% sequence identity with SEQ ID NO: 3.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Höfgen and Willmitzer.

After transformation, plant cells or cell groupings may be selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the HCP5 nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora* meibomiae, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. *medullare* Alef. emend. C.O. Lehm), sugar pea (*Pisum sativum* L. convar. axiphium Alef emend. C.O. Lehm), also called snow pea, edible-podded pea or mangetout, (*Pisum granda sneida* L. convar. *sneidulo* p. *shneiderium*)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis stenocarpa* (Hochst. ex A. Rich.) Harms), Egyptian black bean, dolichos bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus *Phacopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phacosporaceae, for example soybean rust, wherein the recombinant nucleic acid used to generate a transgenic plant comprises a promoter that is functional in the plant cell, operably linked to an HCP5 nucleic acid, which is preferably SEQ ID NO: 1, and a terminator regulatory sequence.

In one embodiment, the present invention refers to a method for the production of a transgenic plant, transgenic plant part, or transgenic plant cell having increased fungal resistance, comprising (a) introducing a recombinant vector construct according to the present invention into a plant, a plant part or a plant cell and
(b) generating a transgenic plant from the plant, plant part or plant cell.

Preferably, the method for the production of the transgenic plant, transgenic plant part, or transgenic plant cell further comprises the step (c) expressing the HCP5 protein, preferably encoded by a nucleic acid comprising
  (i) an exogenous nucleic acid having at least 60% identity with SEQ ID NO: 11, 10, 1, 2, 4, 5, 13-19, 20, 22, 24, 26, 28, 30, 32, or 34, a functional fragment thereof, an orthologue or a paralogue thereof, or a splice variant thereof;
  (ii) an exogenous nucleic acid encoding a protein comprising an amino acid sequence having at least 60% identity with SEQ ID NO: 12, 3, 21, 23, 25, 27, 29, 31, 33, or 35, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by
  (iv) an exogenous nucleic acid encoding the same HCP5 protein as any of the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step (c) expressing the HCP5 protein, preferably encoded by
  (i) an exogenous nucleic acid having at least 60% identity with SEQ ID NO: 1, a functional fragment thereof, an orthologue or a paralogue thereof, or a splice variant thereof;
  (ii) an exogenous nucleic acid encoding a protein having at least 60% identity with SEQ ID NO: 3, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by
  (iv) an exogenous nucleic acid encoding the same HCP5 protein as any of the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step (c) expressing the HCP5 protein, preferably encoded by
  (i) an exogenous nucleic acid having at least 60% identity with SEQ ID NO: 10, a functional fragment thereof, an orthologue or a paralogue thereof, or a splice variant thereof;
  (ii) an exogenous nucleic acid encoding a protein having at least 60% identity with SEQ ID NO: 3, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by (iv) an exogenous nucleic acid encoding the same HCP5 protein as any of the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 10, 1, 2, 4, 5, 13-19, 20, 22, 24, 26, 28, 30, 32, or 34, or a functional fragment thereof, or an orthologue or a paralogue thereof, or a splice variant thereof;

(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 3, 21, 23, 25, 27, 29, 31, 33, or 35, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) an exogenous nucleic acid encoding the same HCP5 polypeptide as any of the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises (i) the exogenous nucleic acid having at least 60% identity with SEQ ID NO: 11, 10, 1, 2, 4, 5, 13-19, 20, 22, 24, 26, 28, 30, 32, or 34, a functional fragment thereof, an orthologue or a paralogue thereof, or a splice variant thereof;

(ii) the exogenous nucleic acid encoding a protein comprising an amino acid sequence having at least 60% identity with SEQ ID NO: 12, 3, 21, 23, 25, 27, 29, 31, 33, or 35, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) the exogenous nucleic acid encoding the same HCP5 protein as any of the nucleic acids of (i) to (iii) above, but differing from the nucleic acids of (i) to (iii) above due to the degeneracy of the genetic code;

preferably the step of harvesting the seeds of the transgenic plant and planting the seeds and growing the seeds to plants, wherein the grown plant(s) comprises (i) the exogenous nucleic acid having at least 60% identity with SEQ ID NO: 11, 10, 1, 2, 4, 5, 13-19, 20, 22, 24, 26, 28, 30, 32, or 34, a functional fragment thereof, an orthologue or a paralogue thereof, or a splice variant thereof;

(ii) the exogenous nucleic acid encoding a protein comprising an amino acid sequence having at least 60% identity with SEQ ID NO: 12, 3, 21, 23, 25, 27, 29, 31, 33, or 35, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or (iv) the exogenous nucleic acid encoding the same HCP5 protein as any of the nucleic acids of (i) to (iii) above, but differing from the nucleic acids of (i) to (iii) above due to the degeneracy of the genetic code;

is repeated more than one time, preferably, 1, 2, 3, 4, 5, 6, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the HCP5 gene or by directly screening for the HCP5 nucleic acid).

Furthermore, the use of the exogenous HCP5 nucleic acid or the recombinant vector construct comprising the HCP5 nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the HCP5 nucleic acid or HCP5 protein. The harvestable parts may be seeds, roots, leaves and/or flowers comprising the HCP5 nucleic acid or HCP5 protein or parts thereof. Preferred parts of soy plants are soy beans comprising the HCP5 nucleic acid or HCP5 protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the HCP5 nucleic acid or HCP5 protein.

Preferably the harvestable parts of the transgenic plant according to the present invention or the products derived from a transgenic plant comprise an exogenous nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11, 10, 1, 2, 4, 5, 13-19, 20, 22, 24, 26, 28, 30, 32, or 34, or a functional fragment, derivative, orthologue, or paralogue thereof, or a splice variant thereof;

(ii) a nucleic acid encoding a HCP5 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 12, 3, 21, 23, 25, 27, 29, 31, 33, or 35, or a functional fragment, derivative, orthologue, or paralogue thereof; preferably the HCP5 protein has essentially the same biological activity as an HCP5 protein encoded by SEQ ID NO: 11, 10, 1, 2, 4, or 5; preferably the HCP5 protein confers enhanced fungal resistance relative to control plants;

(iii) a nucleic acid molecule which hybridizes with a complementary sequence of anyone of the nucleic acids of (i) or (ii) under high stringency hybridization conditions; preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and (iv) a nucleic acid encoding the same HCP5 protein as the HCP5 nucleic acids of (i) to (iii) above, but differing from the HCP5 nucleic acids of (i) to (iii) above due to the degeneracy of the genetic code;

or wherein the harvestable part of the transgenic plant or the product derived from the transgenic plant comprises a HCP5 protein encoded by any one of the HCP5 nucleic acids of (i) to (iv).

Methods for Manufacturing a Product

In one embodiment the method for the production of a product comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably the products obtained by said method comprises an exogenous nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 11, 10, 1, 2, 4, 5, 13-19, 20, 22, 24, 26, 28, 30, 32, or 34, or a functional fragment, derivative, orthologue, or paralogue thereof, or a splice variant thereof;

(ii) a nucleic acid encoding a HCP5 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 12, 3, 21, 23, 25, 27, 29, 31, 33, or 35, or a functional fragment, derivative, orthologue, or paralogue thereof; preferably the HCP5 protein has essentially the same biological activity as an HCP5 protein encoded by SEQ ID NO: 11, 10, 1, 2, 4, or 5; preferably the HCP5 protein confers enhanced fungal resistance relative to control plants;

(iii) a nucleic acid molecule which hybridizes with a complementary sequence of anyone of the nucleic acids of (i) or (ii) under high stringency hybridization conditions; preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and (iv) a nucleic acid encoding the same HCP5 protein as the HCP5 nucleic acids of (i) to (iii) above, but differing from the HCP5 nucleic acids of (i) to (iii) above due to the degeneracy of the genetic code;

or wherein the product obtained by said method comprises a HCP5 protein encoded by any one of the HCP5 nucleic acids of (i) to (iv).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the HCP5 nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of (a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing an HCP5 protein, preferably encoded by a nucleic acid comprising
    (i) an exogenous nucleic acid having at least 60% identity with SEQ ID NO: 11, 10, 1, 2, 4, 5, 13-19, 20, 22, 24, 26, 28, 30, 32, or 34, a functional fragment thereof, an orthologue or a paralogue thereof, or a splice variant thereof;
    (ii) an exogenous nucleic acid encoding a protein comprising an amino acid sequence having at least 60% identity with SEQ ID NO: 12, 3, 21, 23, 25, 27, 29, 31, 33, or 35, or a functional fragment thereof, an orthologue or a paralogue thereof; preferably the encoded protein confers enhanced fungal resistance relative to control plants;
    (iii) an exogenous nucleic acid capable of hybridizing under stringent conditions with a complementary sequence of any of the nucleic acids according to (i) or (ii); preferably encoding a HCP5 protein; preferably wherein the nucleic acid molecule codes for a polypeptide which has essentially identical properties to the polypeptide described in SEQ ID NO: 12 or 3; preferably the encoded protein confers enhanced fungal resistance relative to control plants; and/or by
    (iv) an exogenous nucleic acid encoding the same HCP5 protein as any of the nucleic acids of (i) to (iii) above, but differing from the nucleic acids of (i) to (iii) above due to the degeneracy of the genetic code.

Another preferred embodiment is a method for plant improvement comprising (a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding the HCP5 protein; and optionally
(f) producing propagation material from the plants expressing the nucleic acid encoding the HCP5 protein.

The transgenic plants may be selected by known methods as described above (e.g., by screening for the presence of one or more markers which are encoded by plant-expressible genes co-transferred with the HCP5 gene or screening for the HCP5 nucleic acid itself).

According to the present invention, the introduced HCP5 nucleic acid may be maintained in the plant cell stably if it is incorporated into a non-chromosomal autonomous replicon or integrated into the plant chromosomes. Whether present in an extra-chromosomal nonreplicating or replicating vector construct or a vector construct that is integrated into a chromosome, the exogenous HCP5 nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of *E. coli* cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs

The cDNA was produced from *Arabidopsis thaliana* (ecotype Col-0) RNA by using the Superscript II cDNA synthesis kit (Invitrogen). All steps of cDNA preparation and purification were performed according as described in the manual.

First, the HCP5 sequence from 5' UTR to 3' UTR (including the full-length HCP5) was specifically amplified from the cDNA by PCR as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.2 mM of each dNTP, 100 ng cDNA of *Arabidopsis thaliana* (var Columbia-0), 50 pmol forward primer, 50 pmol reverse primer, 1 u Phusion hot-start, Pfu Ultra, Pfu Turbo or Herculase DNA polymerase.

The amplification cycles were as follows:

1 cycle of 60 seconds at 98° C., followed by 35 cycles of in each case 10 seconds at 98° C., 30 seconds at 60° C. and 90 seconds at 72° C., followed by 1 cycle of 10 minutes at 72° C., then 4° C.

The primers (as shown in SEQ ID 6 and 7) were designed in a way that the specifically bind to sequences in the 5' and 3'UTR upstream of the start ATG an downstream of the stop codon of the HCP5 coding sequence.

```
i) forward primer:
                                (SEQ ID NO: 6)
5'-CTGGATTTAGGCAAGAGGAAG-3'

ii) reverse primer:
                                (SEQ ID NO: 7)
5'-GCTCGGAGGGAGAATTAAGAA-3'
```

The amplified fragment (2458 bp) was eluted and purified from an 1% agarose gel by using the Nucleospin Extract II Kit (Macherey and Nagel, Dueren, Germany). To generate a DNA fragment that contains the restriction sites for cloning a Re-PCR was performed using primers (as shown in SEQ ID NO: 8 and SEQ ID NO: 9) that were designed in a way that an XmaI restriction site is located in front of the start-ATG and a SacII restriction site downstream of the stop-codon.

The HCP5 full-length sequence (SEQ ID NO: 1) was specifically amplified from the eluted PCR fragment (see above) by PCR as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.2 mM of each dNTP, 10-50 ng template DNA derived from the previous PCR of, 50 pmol forward primer, 50 pmol reverse primer, 1 u Phusion hot-start, Pfu Ultra, Pfu Turbo or Herculase DNA polymerase.

The amplification cycles were as follows:

1 cycle of 60 seconds at 98° C., followed by 35 cycles of in each case 10 seconds at 98° C., 30 seconds at 60° C. and 90 seconds at 72° C., followed by 1 cycle of 10 minutes at 72° C., then 4° C.

The following primer sequences were used to specifically amplify the HCP5 full-length DNA for cloning purposes:

```
i) forward primer:
                                (SEQ ID NO: 8)
5'-TACCCGGGATGCTTTTTAATTTGAACGATGAG-3'

ii) reverse primer:
                                (SEQ ID NO: 9)
5'-AACCGCGGCTACTCGTCGGGCCAAGT-3'
```

The primers (as shown in SEQ ID NO: 8 and SEQ ID NO: 9) were designed in a way that an XmaI restriction site is located in front of the start-ATG and a SacII restriction site downstream of the stop-codon.

The amplified fragments were digested using the restriction enzymes XmaI and SacII (NEB Biolabs) and ligated in a XmaI/SacII digested Gateway pENTRY-B vector (Invitrogen, Life Technologies, Carlsbad, Calif., USA) in a way that the full-length HCP5 fragment is located in sense direction between the attL1 and attL2 recombination sites.

It is also possible to generate all DNA fragments mentioned in this invention by DNA synthesis (Geneart, Regensburg, Germany).

Figure 2:
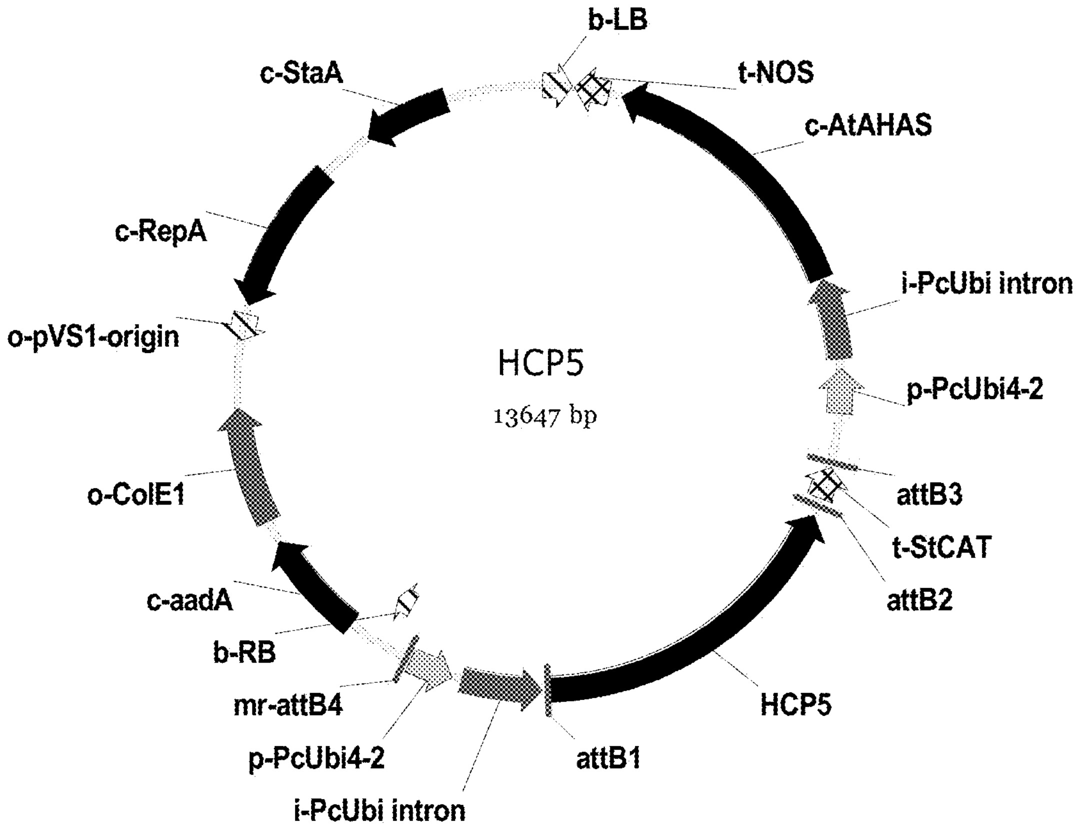
FIG. 2 shows the schematic illustration of the plant transformation vector harboring the HCP5 nucleic acid under control of the parsley ubiquitine promoter.

To obtain the binary plant transformation vector, a triple LR reaction (Gateway system, Invitrogen, Life Technologies, Carlsbad, Calif., USA) was performed according to manufacturer's protocol by using a pENTRY-A vector containing a parsley ubiquitine promoter, the HCP5 full-length gene in a pENTRY-B vector and a pENTRY-C vector containing the terminator of the cathepsin D inhibitor gene from *Solanum tuberosum*. As target a binary pDEST vector was used which is composed of: (1) a Spectinomycin/Streptomycin resistance cassette for bacterial selection, (2) a pVS1 origin for replication in Agrobacteria, (3) a pBR322 origin of replication for stable maintenance in *E. coli*, and (4) between the right and left border an AHAS selection under control of a pcUbi-promoter (see FIG. 2). The recombination reaction was transformed into *E. coli* (DH5alpha), mini-prepped and screened by specific restriction digestions. A positive clone from each vector construct was sequenced and submitted soy transformation.

Example 3: Soy Transformation

The expression vector constructs (see example 2) were transformed into soy.

3.1 Sterilization and Germination of Soy Seeds

Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 μM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 μEinstein/$m^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.

3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 μl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the Agrobacteria were pelleted by centrifugation for 10 min at 5,500×g at 20° C. The pellet was resuspended in liquid CCM to the desired density ($OD_{600}$ 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were sub-cultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soybean plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol.—Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 μE/m$^2$s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

3.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Growth of Plants

10 $T_1$ plants per event were potted and grown for 3-4 weeks in the phytochamber (16 h-day-und 8 h-night-Rhythm at a temperature of 16 and 22° C. and a humidity of 75%) till the first 2 trifoliate leaves were fully expanded.

4.2 Inoculation

The plants were inoculated with spores of *P. pachyrhizi.*

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of $1\text{-}5\times10^5$ spores/ml. For the microscopy, a density of $>5\times10^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1) and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 50 $T_1$ soybean plants (5 independent events, 10 plants each) expressing HCP5 protein were inoculated with spores of *Phakopsora pachyrhizi*. The macroscopic disease symptoms of soy against *P. pachyrhizi* of the inoculated soybean plants were scored 14 days after inoculation.

The average of the percentage of the leaf area showing fungal colonies or strong yellowing/browning on all leaves was considered as diseased leaf area. At all 50 soybean $T_1$ plants expressing HCP5 (expression checked by RT-PCR) were evaluated in parallel to non-transgenic control plants. Non-transgenic soy plants grown in parallel to the transgenic plants were used as control. The average of the diseased leaf area is shown in FIG. 8 for plants exogenously expressing HCP5 compared with wildtype plants. Overexpression of HCP5 reduces the diseased leaf area in comparison to non-transgenic control plants by 25.1% in average over all events generated. This data clearly indicates that the in-planta expression of the HCP5 expression vector construct lead to a lower disease scoring of transgenic plants compared to non-transgenic controls. So, the expression of HCP5 (as shown in SEQ ID NO: 1) in soybean significantly (*: $p<0.05$) increases the resistance of soy against soybean rust.

The invention claimed is:

1. A method for preventing, reducing, or delaying *Phakopsora* infection in a plant, a plant part, or a plant cell, the method comprising:

providing a transgenic plant, transgenic plant part, or transgenic plant cell with an exogenous nucleic acid encoding an HCP5 protein comprising an amino acid sequence having at least 73% identity to SEQ ID NO: 3, wherein the HCP5 protein confers increased resistance against *Phakopsora* thereto in comparison to a wild type plant, wild type plant part or wild type plant cell, wherein the exogenous nucleic acid encoding an HCP5 protein is operably linked to a heterologous promoter; and growing the transgenic plant, transgenic plant part, or transgenic plant cell in the presence of a fungal pathogen of the genus *Phakopsora*, wherein *Phakopsora* infection is prevented, reduced, or delayed in the transgenic plant, transgenic plant part, or transgenic plant cell as compared to a wild type plant, wild type plant part, or wild type plant cell.

2. A recombinant vector construct comprising in operable linkage:

(a) a nucleic acid encoding an HCP5 protein comprising an amino acid sequence having at least 73% identity with SEQ ID NO: 3;

(b) a fungal-inducible promoter; and (c) a transcription termination sequence, wherein expression of said recombinant vector construct in a plant, plant part, or plant cell confers increased resistance against *Phakopsora* thereto in comparison to a wild type plant, wild type plant part or wild type plant cell.

3. The method of claim 1, wherein the promoter is a constitutive promoter, pathogen-inducible promoter, a mesophyll-specific promoter or an epidermis specific-promoter.

4. A transgenic plant, transgenic plant part, or transgenic plant cell comprising a nucleic acid encoding an HCP5 protein comprising an amino acid sequence having at least 73% identity with SEQ ID NO: 3 operably linked to a fungal-inducible promoter.

5. A method for the production of a transgenic plant, transgenic plant part, or transgenic plant cell having increased fungal resistance, comprising:

(a) introducing the recombinant vector construct of claim 2 into a plant, a plant part, or a plant cell; and (b) generating a transgenic plant, transgenic plant part, or transgenic plant cell from the plant, plant part or plant cell.

6. The method of claim 5, further comprising the step of harvesting the seeds of the transgenic plant and planting the seeds and growing the seeds to plants, wherein the grown plants comprise the recombinant vector construct.

7. A harvestable part of the transgenic plant of claim 4, wherein the part comprises the nucleic acid encoding the HCP5 protein operably linked to the fungal-inducible promoter.

8. A product derived from the plant of claim 4, wherein the product comprises the nucleic acid encoding the HCP5 protein operably linked to the fungal-inducible promoter.

9. A method for the production of a product, said method comprising:

a) growing the plant of claim 4; and b) producing said product from the plant and/or a part thereof;

wherein the product obtained by said method comprises the nucleic acid encoding the HCP5 protein operably linked to the fungal-inducible promoter.

10. The method of claim 9, wherein the product is produced from the seeds of the plant.

11. The method of claim 9, wherein the product is meal or oil.

12. The method of claim 1, wherein the plant is selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

13. A method for breeding a fungal resistant plant, said method comprising:

(a) crossing the plant of claim 4 with a second plant;

(b) obtaining seed from the cross of step (a);

(c) planting said seeds and growing the seeds to plants; and (d) selecting from the plants produced in step (c) plants expressing the HCP5 protein.

14. The product of claim 8, wherein the product is soybean meal or soy oil.

* * * * *